US009250211B2

(12) United States Patent  
Caulfield et al.

(10) Patent No.: US 9,250,211 B2  
(45) Date of Patent: *Feb. 2, 2016

(54) MAGNETIC SEPARATION OF LIPOPROTEINS USING DEXTRAN SULFATE

(75) Inventors: Michael P. Caulfield, San Clemente, CA (US); Jackie Liu, Tustin, CA (US); Dawn Shalhout, Trabuco Canyon, CA (US); Zhihong Chen, Aliso Viejo, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/340,547

(22) Filed: Dec. 29, 2011

(65) Prior Publication Data  
US 2012/0285831 A1 Nov. 15, 2012

Related U.S. Application Data

(60) Provisional application No. 61/428,812, filed on Dec. 30, 2010.

(51) Int. Cl.  
*G01N 27/62* (2006.01)  
*C07K 1/22* (2006.01)  
*C07K 1/30* (2006.01)  
*C07K 1/36* (2006.01)

(52) U.S. Cl.  
CPC .............. *G01N 27/622* (2013.01); *C07K 1/22* (2013.01); *C07K 1/30* (2013.01); *C07K 1/36* (2013.01)

(58) Field of Classification Search  
None  
See application file for complete search history.

(56) References Cited

U.S. PATENT DOCUMENTS

| 1,825,661 | A |   | 10/1931 | Gull |
| 4,678,566 | A | * | 7/1987  | Watanabe et al. ............. 210/143 |
| 4,933,844 | A |   | 6/1990  | Otvos |
| 5,076,097 | A |   | 12/1991 | Zarrin et al. |
| 5,247,842 | A |   | 9/1993  | Kaufman et al. |
| 5,343,389 | A |   | 8/1994  | Otvos |

(Continued)

FOREIGN PATENT DOCUMENTS

| EP | 0 546 916      | 6/1993  |
| EP | 0 627 627 A1   | 12/1994 |

(Continued)

OTHER PUBLICATIONS

Warnick, G.R., et al., Dextran sulfate-Mg2+ precipitation procedure for quantitation of high-density-lipoprotein cholesterol. Clin. Chem., 28, 1379-1388 (1982).*

(Continued)

*Primary Examiner* — Alexander Kim  
(74) *Attorney, Agent, or Firm* — Foley & Lardner LLP

(57) ABSTRACT

The invention provides apparatus and methods of preparation of lipoproteins from a biological sample, including HDL, LDL, Lp(a), IDL, and VLDL, for diagnostic purposes utilizing differential charged-particle mobility analysis methods. Further provided are methods for analyzing the size distribution of lipoproteins by differential charged-particle mobility, which lipoproteins are prepared by methods of the invention. Further provided are methods for assessing lipid-related health risk, cardiovascular condition, risk of cardiovascular disease, and responsiveness to a therapeutic intervention, which methods utilize lipoprotein size distributions determined by methods of the invention.

29 Claims, 30 Drawing Sheets

(56) References Cited

U.S. PATENT DOCUMENTS

| | | | |
|---|---|---|---|
| 5,460,974 A * | 10/1995 | Kozak et al. ............... | 436/71 |
| 5,561,515 A | 10/1996 | Hairston et al. | |
| 5,595,913 A | 1/1997 | Lawlor et al. | |
| 5,701,012 A | 12/1997 | Ho | |
| 5,756,291 A | 5/1998 | Griffin et al. | |
| 5,788,166 A | 8/1998 | Valaskovic et al. | |
| 5,856,196 A | 1/1999 | Alvarez et al. | |
| 5,895,922 A | 4/1999 | Ho | |
| 5,925,229 A | 7/1999 | Krauss et al. | |
| 5,932,080 A | 8/1999 | Likuski | |
| 5,999,250 A | 12/1999 | Hairston et al. | |
| 6,020,208 A | 2/2000 | Hutchens et al. | |
| 6,107,045 A | 8/2000 | Koren et al. | |
| 6,126,835 A | 10/2000 | Barbera-Guillem et al. | |
| 6,145,391 A | 11/2000 | Pui et al. | |
| 6,248,545 B1 | 6/2001 | Kondo et al. | |
| 6,267,579 B1 | 7/2001 | Li et al. | |
| 6,469,297 B1 | 10/2002 | Kato et al. | |
| 6,485,686 B1 | 11/2002 | Wick | |
| 6,491,872 B1 | 12/2002 | Wick | |
| 6,716,994 B1 | 4/2004 | Menchen et al. | |
| 6,753,185 B2 | 6/2004 | MacFarlane et al. | |
| 7,075,066 B2 | 7/2006 | Bailey et al. | |
| 7,259,018 B2 | 8/2007 | Benner et al. | |
| 8,247,235 B2 * | 8/2012 | Caulfield et al. ............... | 436/71 |
| 2002/0098597 A1 | 7/2002 | Koren et al. | |
| 2003/0066969 A1 | 4/2003 | De La Mora | |
| 2003/0124743 A1 | 7/2003 | Kundu | |
| 2003/0136680 A1 | 7/2003 | Benner et al. | |
| 2003/0234356 A1 | 12/2003 | Konermann et al. | |
| 2004/0029293 A1 | 2/2004 | Nugent et al. | |
| 2004/0119009 A1 | 6/2004 | Hanold et al. | |
| 2004/0137542 A1 | 7/2004 | Petyaev | |
| 2005/0023455 A1 | 2/2005 | Bailey et al. | |
| 2005/0042695 A1 | 2/2005 | Meares et al. | |
| 2005/0061722 A1 | 3/2005 | Takao et al. | |
| 2007/0048795 A1 | 3/2007 | Fang et al. | |
| 2007/0090026 A1 | 4/2007 | Han et al. | |
| 2008/0302666 A1 | 12/2008 | Benner et al. | |
| 2008/0305549 A1 | 12/2008 | Caulfield et al. | |
| 2009/0132443 A1 | 5/2009 | Mueller et al. | |
| 2009/0136937 A1 | 5/2009 | Coleman et al. | |
| 2013/0136680 A1 | 5/2013 | Nagayasu et al. | |

FOREIGN PATENT DOCUMENTS

| | | |
|---|---|---|
| EP | 1 045 247 | 10/2000 |
| JP | 09-072891 | 3/1997 |
| JP | 2001-124780 | 5/2001 |
| JP | 2001-527090 | 12/2001 |
| JP | 2005-509860 | 4/2005 |
| WO | WO 93/17776 * | 9/1993 |
| WO | WO-99/17096 | 4/1999 |
| WO | WO 99/33860 A1 | 7/1999 |
| WO | WO-00/51054 | 8/2000 |
| WO | WO-00/65366 | 11/2000 |
| WO | WO-03/042704 | 5/2003 |
| WO | WO-2004/014942 | 2/2004 |
| WO | WO-2007/004687 A1 | 1/2007 |
| WO | WO 2008/154422 * | 12/2008 |

OTHER PUBLICATIONS

Gibson et al., Precipitation of apo E-containing lipoproteins by precipitation reagents for apolipoprotein B. Clin Chem. (1984) vol. 30(11), pp. 1784-1788.*
Goldbio.com (last viewed on Jul. 1, 2014).*
Nierman et al., Enhanced Conversion of Triglyceride-Rich Lipoproteins and Increased Low-Density Lipoprotein Removal in LPLS447X Carriers., Arteriosclerosis, Thrombosis, and Vascular Biology (2005), vol. 25, pp. 2410-2415.*
Merki et al., Antisense Oligonucleotide Directed to human Apolipoprottein B-100 Reduces Lipoprotein(a) Levels and Oxidized Phospholipids on Human Apolipoprotein B-100 Particles in Lipoprotein(a) Transgenic Mice., Circulation (2008), vol. 11825, pp. 743-753.*
Zhou et al., Preparation of uniform-sized agarose beads by microporous membrane emulsification technique., Journal of Colloid and Interface Science (2007), vol. 311, pp. 117-127.*
Nauck et al., New immunoseparation-based homogeneous assay for HDL-cholesterol compared with three homogeneous and two heterogenous method fo HDL-cholesterol., Clin Chem. (1998) vol. 44(7), pp. 1443-1451.*
Sera-Mag® Magnetic Carboxylate-Modified Microparticles (Nov. 2000).*
Sera-Mag SpeedBeads Magnetic Microparticles (Oct. 2006).*
Finley et al., Cholesterol in high-density lipoprotein: use of Mg2+/dextran sulfate in its enzymic measurement. Clinical Chemistry (1978), vol. 24, pp. 931-933.*
Esteban-Salan et al., Analytical and Clinical Evaluation of Two Homogeneous Assays for LDL-Cholesterol in Hyperlipidemic Patients., Clinical Chemistry (2000), vol. 46 No. 8 1121-1131.*
Rudel et al., Characterization of Plasma Lipoproteins Separated and Purified by Agarose-Column Chromatography, Biochem. J. (1974), vol. 139, pp. 89-95.*
Janado et al., Sedimentation Properties of Dextran Sulfate-Low Density Lipoprotein Complexes., Agricultural and Biological Chemistry (1967), vol. 31, pp. 802-808.*
Fowkes et al., Inter-relationships of plasma fibrinogen, low-density lipoprotein cholesterol, cigarette smoking and the prevalence of cardiovascular disease., J Cardiovasc Risk. (1996), vol. 3(3), pp. 307-311.*
Stec et al., Association of Fibrinogen With Cardiovascular Risk Factors and Cardiovascular Disease in the Framingham Offspring Population Circulation (2000), vol. 102, pp. 1634-1638.*
Bairaktari et al., Evaluation of Methods for the Measurement of Low-Density Lipoprotein Cholesterol, J Cardiovasc Pharmacol Therapeut (2005), vol. 10, pp. 45-54).*
Jeyarajah et al., Lipoprotein particle analysis by nuclear magnetic resonance spectroscopy. Clin. Lab. Med., 26:847-870, 2006.
Kulkarni et al., Quantification of cholesterol in all lipoprotein classes by the VAP-II method. J. Lip. Res., 35:159-168, 1994.
"Reactive Dye Affinity Chromatography Matrices" Sigma Product Information, Jan. 10, 2000, XP055050205, 6 pages.
Altintas, et al, Efficient removal of albumin from human serum by monosize dye-affinity beads, (2006), J Chromatography B, 832(2):216-223.
Amthauer, et al, Interaction of cibacron blue and anilinonaphthalenesulphonate with lipoproteins provides a new mean for simple isolation of these plasma proteins, (1988), Biochem Biophys Res Comm, 154(2):752-757.
Atherotech, Inc., Test Benefits—VAP/CAD Lipoprotein Risk Assessment Test, http://home.socal.rr.com/asylem/test_ben.htm, Atherotech, Inc., USA, p. 1-3, 2001.
Axis-Shield PoC AS: Optiprep—product description, (2003), XP002598992, retrieved from URL:http://www.freewebs.com/eldril123/packageinsert/optiprep.pdf, retrieved on Oct. 31, 2010.
Bacher et al, Charge-reduced nano electrospray ionization combined with differential mobility analysis of peptides, proteins, glycoproteins, noncovalent protein complexes and viruses, Journal of Mass Spectrometry, 36(9):1038-1052, Sep. 2001.
Barbagallo et al, Influence of ApoE content on receptor binding of large buoyant LDL in subjects with different DLD subclass phenotypes, Arterioscler Thromb Vasc Biol, (18)466-472, 1998.
Bell et al, [LJ.09] The dynamics of a steady Taylor cone electrospray, BAPSDFD98—Abstracts, American Physical Society, USA, Nov. 24, 1998.
Benner et al, Investigating Intact Viruses with Charge-Detection MS and Ion Mobility, Proc. 49th ASMS Conf. on Mass Spectrometry and Allied Topics, ASMS, Chicago IL, May 27, 2001.
Berneis et al., Analysis and quantitation of biotinylated apoB-containing lipoproteins with streptavidin-Cy3, J. Lipid Res., 43:1155-1159, 2002.
Berneis et al., Metabolic origins and clinical significance of LDL heterogeneity, J. Lipid Res., 43:1363-1379, 2002.

(56) References Cited

OTHER PUBLICATIONS

Bundy et al, A novel Method for the Analysis of Complex Biological Protein Mixtures Using Electrospray Ionization Mass Spectrometry Combined with Ion/Ion Chemistry, Proc. 49th ASMS Conf. on Mass Spectrometry and Allied Topics, ASMS, Chicago IL, May 27,2001.
Burstein, et al., "Rapid Method for the Isolation of Two Purified Subfractions of High Density Lipoproteins by Differential Dextran Sulfate-Magnesium Chloride Precipitation," Biochimie, Masson, Paris, FR, vol. 71, No. 6, 1989, pp. 741-746.
Campos et al, Predominance of large LDL and reduced HDL2 cholesterol in normolipidemic men with coronary artery disease, Arteriosclerosis, Thrombosis & Vascular Biology, 15(8):1043-1048, Aug. 1995.
Caulfield, et al, Direct determination of lipoprotein particle sizes and concentrations by ion mobility analysis, (2008), Clin Chem, 54(8):1307-1316.
Communication in EP application No. 08770383.1 dtd Jul. 6, 2010.
Communication pursuant to Article 94(3) EPC dated Apr. 11, 2012 in EP application 08770383.1.
Davies, et al., Rapid separation of LDL subclasses by iodixanol gradient ultracentrifugation, (2003), Clin Chem, 49(11):1865-1872.
Dreon et al, Diet-gene interactions in human lipoprotein metabolism, J. Amer. College of Nutrition, 16(4):313-324,1997.
Dreon et al, LDL subclass patterns and lipoprotein response to a low-fat, high-carbohydrate diet in women, Arteriosclerosis, Thrombosis & Vascular Biology, 17(4):707-714, Apr. 1997.
Dreon et al, Low-density lipoprotein subclass patterns and lipoprotein response to a reduced-fat diet in men, FASEB Journal, 8(1):121-126, Jan. 1994.
Dreon et al, Reduced LDL particle size in children consuming a very-low-fat diet is related to parental LDL-subclass patterns, Am. J. Clin. Nutr., 71:1611-1616, 2000.
Dreon et al., A very low-fat diet is not associated with improved lipoprotein profiles in men with a predominance of large, low-density lipoproteins, Am. J. Clin. Nutr., 69: 411-418, 1999.
Dreon et al., Change in dietary saturated fat intake is correlated with change in mass of large low-density-lipoprotein particles in men, Am. J. Clin. Nutr., 67:828-836, 1998.
Edmonds et al, Capillary Electrophoresis-Electrospray Ionization-Mass Spectrometry, J. Chromatogr., PNL, USA, (474):21-37, 1989.
EPO Communication issued in application EP 08770383.1 dated Jan. 28, 2013.
Extended European Search Report dated Sep. 20, 2010 in EP application 08770383.1.
Feingold et al., The hypertriglyceridemia of acquired immunodeficiency syndrome is associated with an increased prevalence of low density lipoprotein subclass pattern B, Journal of Clinical Endocrinology & Metabolism, 76(6):1423-1427, Jun. 1993.
Final Office Action in U.S. Appl. No. 12/537,191 dated Sep. 8, 2011 (14 pages).
Final Office Action issued for U.S. Appl. No. 13/589,404 dated Apr. 25, 2013.
Friedewald et al., Estimation of the concentration of low-density lipoprotein cholesterol in plasma, without use of the preparative ultracentrifuge, Clin. Chem., 1972, 18:499-502.
Gardner et al, Association of small low-density lipoprotein particles with the incidence of coronary artery disease in men and women, Comment in: JAMA, vol. 276(11):875-881, Sep. 18, 1996.
Gardner, et al, Separation of bovine plasma lipoproteins by a rapid ultracentrifugation method, (2003), J Comp Path, 128(1):15-23.
Graham, et al., A novel method for the rapid separation of plasma lipoproteins using self-generating gradient of iodixanol, (1996), Atherosclerosis, 124(1):125-135.
Gray et al, Relation of LDL size to the insulin resistance syndrome and coronary heart disease in American Indians, Arteriosclerosis, Thrombosis & Vascular Biology, 17(11):2713-2720, Nov. 1997.
Griffin, et al, Rapid isolation of low density lipoprotein LDL subfractions from plasma by density gradient ultracentrifugation, (1990), Atherosclerosis, 83(1):59-68.
Gross, et al., "Isolation of Lipoprotein (a) Using the Regenerate of a Dextran Sulfate Cellulose LDL Apheresis System," Protein Expression and Purification, Academic Press, San Diego, CA, vol. 5, No. 2, 1994, pp. 112-117.
Hallberg, et al., Lipoprotein fractionation in deuterium oxide gradients, (1994), J Lipid Research, 35(1):1-9.
Haskell et al, Effects of intensive multiple risk factor reduction on coronary atherosclerosis and clinical cardiac events in men and women with coronary artery disease. The Stanford Coronary Risk Intervention Project (SCRIP), Circulation, 89(3):975•990, Mar. 1994.
Havel et al, Genetic underpinnings of LDL size and density: a role for hepatic lipase?, Am. J. Clin. Nutr., 71:1390-1391, 2000.
Henderson et al, Intrinsic Size Parameters for Val, Ile, Leu, Gln, Thr, Phe, and Trp Residues from Ion Mobility Measurements of Polyamino Acid Ions, J. Phys. Chem. B, 103:8780•8785, 1999.
Hennessy, et al., "Isolation of Subpopulations of High Density Lipoproteins: Three Particle Species Containing apoE and Two Species Devoid of apoE that Have Affinity for Heparin," Journal of Lipid Research, vol. 38, No. 9, 1997, pp. 1859-1868.
Hildebrandt et al., "Superparamagnetic Iron Oxide Nanoparticles Functionalized with Peptides by Electrostatic Interactions", ARKIVOC, 2007, pp. 79-90.
Hodis et al, Intermediate-density lipoproteins and progression of carotid arterial wall intima-media thickness, Circulation, 95(8):2022-2026, Apr. 15, 1997.
International Preliminary Report on Patentability dated Dec. 11, 2009 in international application PCT/US2008/066178.
International Search Report dated Aug. 20, 2008 in international application PCT/US2008/66178 (3 pages).
Jeyarajah et al, Radio signals give new spectrum for cholesterol lipoprotein readings, American Heart Association Journal Report—News Release, American Heart Association, USA, p. 1-3, Jul. 9, 1998.
Kaddis, et al., "Sizing Large Proteins and Protein Complexes by Electrospray Ionization Mass Spectrometry and Ion Mobility," Journal of the American Society for Mass Spectrometry, Elsevier Science Inc, US, vol. 18, No. 7, 2007, pp. 1206-1216.
Katzel et al, Persistence of low HDL levels after weight reduction in older men with small LDL particles, Arteriosclerosis, Thrombosis & Vascular Biology, 15(3):299-305, Mar. 1995.
Krauss et al, Detection and quantitation of LDL subfractions, Current Opinion in Lipidology, Current Science Ltd., 3:377-383, 1992.
Krauss et al, Lipoprotein subclasses in genetic studies: the Berkeley data set, Genetic Epidemiology, 10(6):523-528, 1993.
Krauss et al, Low-density-lipoprotein subclasses and response to a low-fat diet in healthy men, American Journal of Clinical Nutrition, 62(2):4785-4875, Aug. 1995.
Krauss et al., Atherogenic lipoprotein phenotype and diet-gene interactions, American Society for Nutritional Science Symposium: Nutritional and Metabolic Diversity: Understanding the Basis of Biologic Variance in the Obesity/Diabetes/Cardiovascular Disease Connection, p. 340S-343S, 2001.
Krauss, R.M., Dietary and genetic effects on low-density lipoprotein heterogeneity, Annu. Rev. Nutr. 21:283-295, 2001.
Krauss, R.M., Is the size of low-density lipoprotein particles related to the risk of coronary heart disease?, JAMA, 287(6): 712-713, Feb. 13, 2002.
Krauss, R.M., Triglyceride-Rich Lipoproteins, LDL Particle Size, and Atherogenesis, American Assoc. of Clinical Endocrinologists Ninth Annual Meeting and Clinical Congress, Amer. Assoc. Clinical Endocrinologists, May 3, 2000.
Kulkarni et al., Quantification of cholesterol in all lipoprotein classes by the VAP-II method, J. Lip. Res., 1994, 35:159-168.
Legro et al., Alterations in low-density lipoprotein and high-density lipoprotein subclasses among Hispanic women with polycystic ovary syndrome: influence of insulin and genetic factors, Fertility and Sterility, 72(6):990-995, Dec. 1999.
Lindgren et al, Chapter 5—The Isolation and Quantitative Analysis of Serum Lipoproteins, Blood Lipids and Lipoproteins: Quantitation Composition and Metabolism, 1992, p. 181-274.
Mack et al, Lipoprotein subclasses in the Monitored Atherosclerosis Regression Study (MARS), Treatment effects and relation to coro-

(56) References Cited

OTHER PUBLICATIONS nary angiographic progression, Arteriosclerosis, Thrombosis & Vascular Biology, 16(5):697-704, 1996.
Mulholland, et al., "Measurement of 100 nm and 60 nm Particle Standards by Differential Mobility Analysis," Journal of Research of the National Institute of Standards and Technology, vol. 111, No. 4, 2006, pp. 257-312.
Muniz et al, A New Tool for the Automated Analysis of LDL Subfraction Patterns Generated by the Lipoprint LDL System, www.4qc.com, Quantimetrix Corporation, USA, p. 1-11, 2001.
New Objective, Inc., Bring Electrospray Into Focus, LC-MS Nano-ESI Proteomics, New Objective, Inc. (www.newobjective.com), USA, 2001.
New Objective, Inc., Product Catalog: Fused Silica Pico Tips, Products (www.newobjective.com), New Objective, Inc., USA, 2001.
New Objective, Inc., What is Electrospray?, Products (www.newobjective.com), New Objective, Inc., USA, 2001.
Non-Final Office Action for U.S. Appl. No. 13/589,404 dated Nov. 29, 2012.
Notice of Allowance dated Apr. 5, 2012 for U.S. Appl. No. 11/760,672.
Notice of Allowance in U.S. Appl. No. 13/589,404 dtd Dec. 12, 2013.
Notice of Allowance in U.S. Appl. No. 13/589,404 dtd Sep. 4, 2013.
Office Action in CN application No. 200880101850.3 dtd Nov. 28, 2013 (English translation).
Office Action in U.S. Appl. No. 11/760,672 dtd Jun. 29, 2010 (12 pages).
Office Action in U.S. Appl. No. 11/760,700 dtd May 19, 2010 (10 pages).
Office Action in U.S. Appl. No. 11/760,700 dtd Sep. 1, 2009 (13 pages).
Office Action in U.S. Appl. No. 12/537,191 dtd Apr. 29, 2011 (13 pages).
Office Action issued in Chinese Patent Application No. 200880101850.3 dated Jul. 3, 2012.
Office Action issued in Chinese Patent Application No. 200880101850.3 dated Mar. 14, 2013.
Office Action issued in Japanese Patent Application No. 2010-511380 dated Mar. 12, 2013.
Partial European Search Report in EP application No. 13169486.1 dtd Aug. 14, 2013.
Partial European Search Report in EP application No. 13169517.3 dtd Aug. 16, 2013.
Patent Examination Report No. 1 Issued in Australian Patent Application No. 2008261868 dated Mar. 8, 2013.
Quantimetrix Corporation, Lipoprint System for LDL Subfraction, Lipoprint Technical—What's New (www.4qc.com), Quantimetrix Corporation, USA, p. 1, 2001.
Roche, Quick spin protein columns: G-25 sephadex (fine) columns for protein desalting and buffer exchange, Version Jan. 2, 2002.
Sjoblom, et al., "Determination of HDL2 Cholesterol by Precipitation with Dextran Sulfate and Magnesium Chloride: Establishing Optimal Conditions for Rat Plasma," Lipids, Springer-Verlag, Berlin/Heidelberg, vol. 24, No. 6, 1989, pp. 532-534.
Stampfer et al, A prospective study of triglyceride level, low-density lipoprotein particle diameter, and risk of myocardial infarction, Comment in: JAMA, 276(11):882-888, Sep. 18, 1996.
Superko et al, Association of lipoprotein subclass distribution with use of selective and non-selective beta-blocker medications in patients with coronary heart disease, Atherosclerosis, 101(1):1-8, Jun. 1993.
Superko et al, Effect of Fluvastatin on Low-density lipoprotein peak particle diameter, Amer. J. of Cardiology, 80:78-81, Jul. 1, 1997.
Superko et al, Garlic powder, effect on plasma lipids, postprandial lipemia, low-density lipoprotein particle size, high-density lipoprotein subclass distribution and lipoprotein(a), J. Am. College of Cardiology, 35(2):321-326, 2000.

Talameh, et al., "Measurement of Total HDL, HDL2 and HDL3 by Dextran Sulfate—MgCl2 Precipitation Technique in Human Serum," Clinica Chimica Acta, Elsevier BV, Amsterdam, NL, vol. 158, No. 1, 1986, pp. 33-41.
Tribble et al., Enhanced oxidative susceptibility and reduced antioxidant content of metabolic precursors of small, dense low-density lipoproteins, Amer. J. of Medicine, 110:103-110, 2001.
TSI Incorporated, Correlation of EM Diameter with Molecular Weight, GEMMA Example—EM Diameter vs. Molecular Weight (www.tsi.com), TSI Incorporated, Particle Instrumentation Division, USA, 1999.
TSI Incorporated, Gemma Method for Macromolecule/Nanoparticle Analysis, GEMMA Method Product Page (www.tsi.com), TSI Incorporated, Particle Instrument Division, USA, 1999.
TSI Incorporated, Model 3080-Series Electrostatic Classifiers, TSI Product Info. Sheets (www. tsi.com),TSI Incorporated, USA, 1999.
TSI Incorporated, Model 3312 Ultraviolet Aerodynamic Particle Sizer Spectrometer, Preliminary Product Information (www.tsi.com), TSI Incorporated, USA, 1997.
TSI Incorporated, Model 3313 Fluorescence Aerodynamic Particle Sizer Sensor, 2002, 4 pgs.
TSI Incorporated, Model 3480 Electrospray Aerosol Generator, 3480 Advance Product Information (www. tsi.com), TSI Incorporated, Particle Instrument Division, USA, 1999.
TSI Incorporated, Model 3980 GEMMA Macromolecule Analyzer; TSI Advance Product Information (www.tsi.com), TSI Incorporated, USA, 2000.
TSI Incorporated, Protein Mixture, GEMMA Example—Protein Mixture (www.tsi.com), TSI Incorporated, Particle Instrument Division, USA, 1999.
US Office Action dated Dec. 7, 2011 in U.S. Appl. No. 11/760,672.
US Office Action dated Jul. 11, 2011 in U.S. Appl. No. 11/760,672.
US Office Action dated Sep. 22, 2010 in U.S. Appl. No. 11/760,672.
US Office Action dated Oct. 8, 2010 in U.S. Appl. No. 11/760,700.
Vallance, et al., "Precipitation Procedures Used to Isolate High Density Lipoprotein with Particular Reference to Effects on Apo A-I-Only Particles and Lipoprotein(a)," Clinica Chimica Acta, Elsevier BV, Amsterdam, NL, vol. 229, No. 1-2, 1994, pp. 77-85.
Waugh et al, Rapid method for determining cholesteryl ester transitions of apoB-containing lipoproteins, Journal of Lipid Research, 23:201-204, 1982.
Williams et al, Associations of age, adiposity, alcohol intake, menstrual status, and estrogen therapy with high-density lipoprotein subclasses, Arteriosclerosis and Thrombosis, 13(11):1654-1661, Nov. 1993.
Williams et al, Effects of dietary fat on high-density-lipoprotein subclasses are influenced by both apolipoprotein E isoforms and low-density-lipoprotein subclass patterns, American Journal of Clinical Nutrition, 61(6):1234-1240, Jun. 1995.
Williams et al, The associations of high-density lipoprotein subclasses with insulin and glucose levels, physical activity, resting heart rate, and regional adiposity in men with coronary artery disease, Metabolism: Clinical & Experimental, 44(1):106-114, Jan. 1995.
Williams et al, Variability of plasma HDL subclass concentrations in men and women over time, Arteriosclerosis, Thrombosis & Vascular Biology, 17(4):702-706, Apr. 1997.
Williams et al., Low-fat diets, lipoprotein subclasses, and heat disease risk, Am. J. Clin. Nutr., 70:949-950, 1999.
Yang et al., Multilectin affinity chromatography for characterization of multiple glycoprotein biomarker candidates in serum from breast cancer patients, Clinical Chemistry, 52(2):1-9, 2006.
Notice of Reasons for Rejection issued in Japanese Application No. 2010-511380 dtd Jan. 7, 2014 (includes English translation—5 pages).
Angal, et al., "The Effect of Matrix on the Binding of Albumin to Immobilized Cibacron Blue," Biochem. J. (1977) 167, pp. 301-303.
Communication Pursuant to Article 94(3) EPC in European Application No. 13169486.1 dtd Nov. 10, 2014 (5 pages).
Communication under Rule 71(3) EPC in European Application No. 08770383.1 dtd Oct. 29, 2014 (7 pages).
Notice of Reasons for Rejection in Japanese Application No. 2010-511380 dtd Nov. 18, 2014 (English translation included—3 pages).
Sigma-Aldrich, "Reactive Blue 4-Agarose," 2012, 2 pages.

(56) References Cited

OTHER PUBLICATIONS

Sigma-Aldrich, "Reactive Brown 10-Agarose," 2012, 2 pages.
Sigma-Aldrich, "Reactive Green 5-Agarose," 2012, 1 page.
Sigma-Aldrich, "Reactive Yellow 86-Agarose," 2012, 1 page.
Final Office Action in U.S. Appl. No. 14/226,089 dtd Oct. 8, 2014 (13 pages).
Non-Final Office Action in U.S. Appl. No. 14/226,089 dtd Jun. 26, 2014 (14 pages).
Non-final Office Action in U.S. Appl. No. 12/537,191 dtd Apr. 14, 2014 (10 pages).
Final Office Action in U.S. Appl. No. 12/537,191 dtd Aug. 22, 2014 (15 pages).
Sigma, R2882 Reactive Green 19-Agarose, Saline suspension, 2007.
Notice of Allowance in U.S. Appl. No. 14/226,089 dtd Jan. 26, 2015 (9 pages).
US Office Action in U.S. Appl. No. 12/537,191 dated Aug. 7, 2015 (8 pages).

* cited by examiner

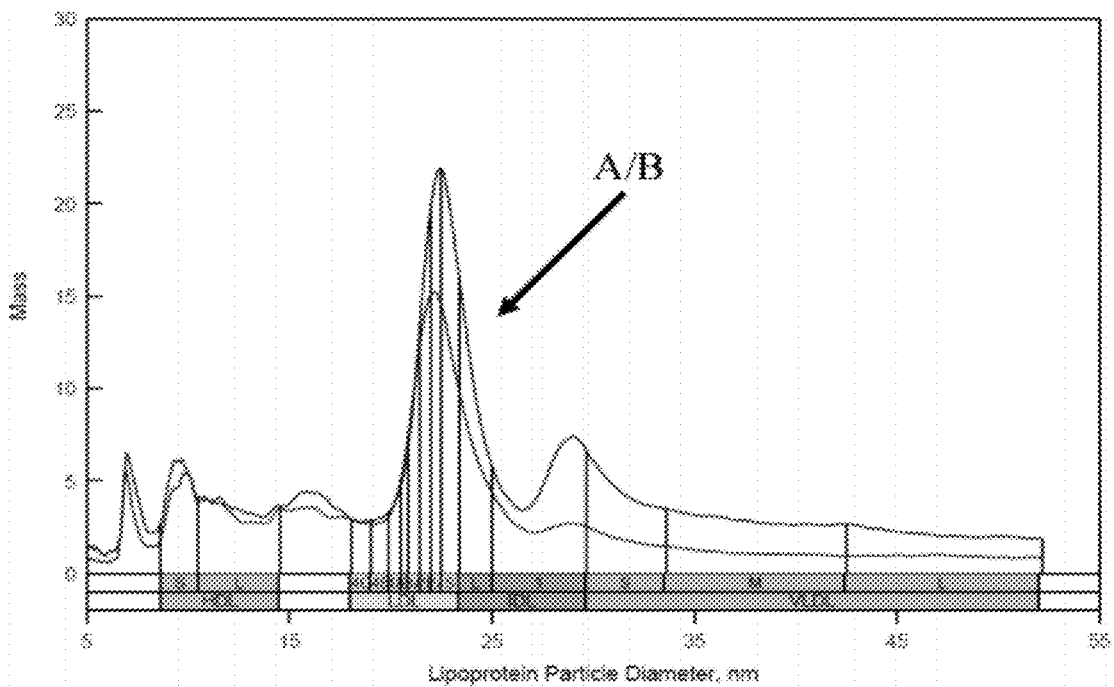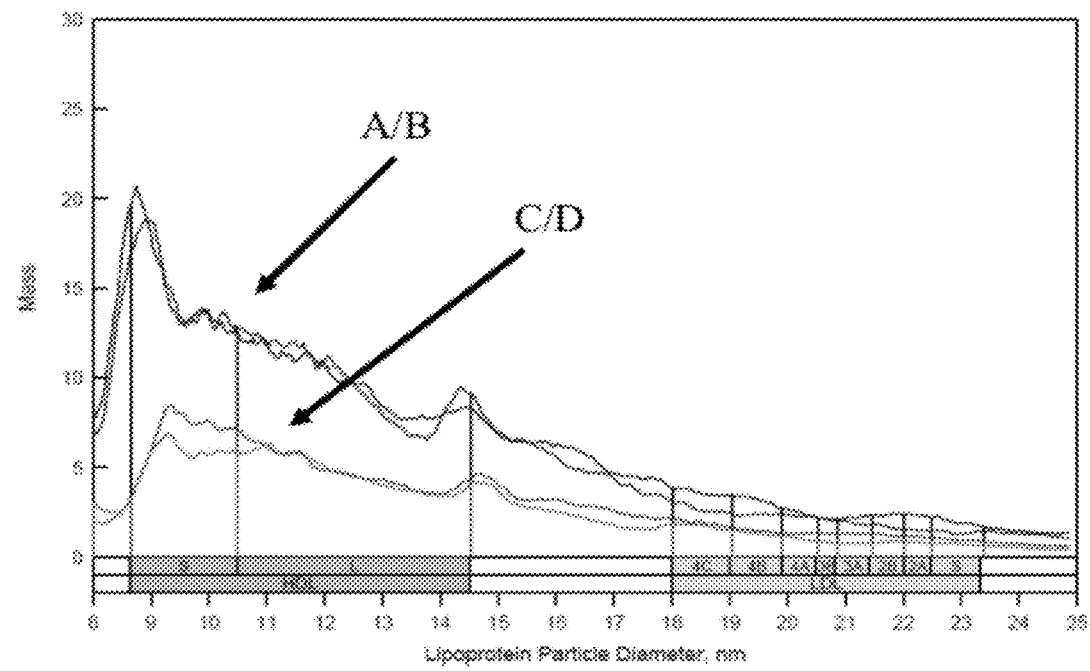

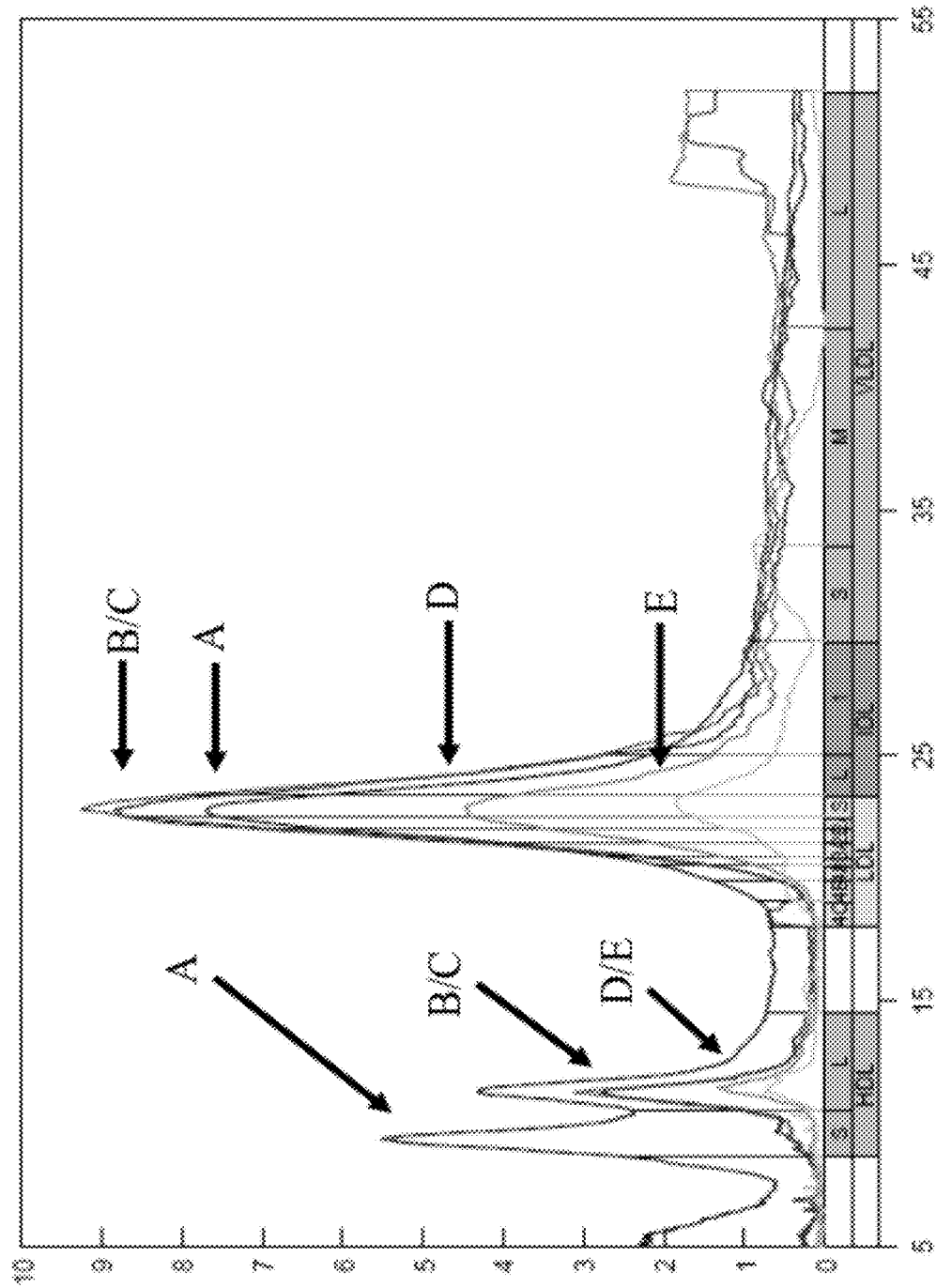

FIG. 20A

| (n = 10) | | Peak Diam. | LDL Very Small nmol/L | LDL Small nmol/L | LDL Medium nmol/L | LDL Large nmol/L | HDL Total nmol/L | HDL Large nmol/L | IDL Total nmol/L | VLDL Total nmol/L |
|---|---|---|---|---|---|---|---|---|---|---|
| Sample 1 | Mean | 216 | 210 | 204 | 230 | 395 | 20722 | 6193 | 355 | 182 |
| | Stdv | 1.5 | 23 | 23 | 24 | 40 | 2265 | 671 | 41 | 21 |
| | %CV | 0.7 | 10.9 | 11.3 | 10.3 | 10.1 | 10.9 | 10.8 | 11.5 | 11.8 |
| Sample 2 | Mean | 221 | 157 | 189 | 375 | 752 | 18967 | 6333 | 388 | 86 |
| | Stdv | 1.4 | 6.9 | 17.8 | 35.2 | 73.3 | 1221.1 | 397.1 | 28.4 | 5.7 |
| | %CV | 0.6 | 4.4 | 9.4 | 9.4 | 9.7 | 6.4 | 6.3 | 7.3 | 6.6 |
| Sample 3 | Mean | 227 | 162 | 127 | 163 | 452 | 20304 | 6733 | 373 | 71 |
| | Stdv | 2.9 | 18.4 | 15.4 | 16.3 | 42.3 | 1720.6 | 624.5 | 34.7 | 8.6 |
| | %CV | 1.3 | 11.4 | 12.2 | 10.0 | 9.4 | 8.5 | 9.3 | 9.3 | 12.0 |

FIG. 21A

| (n = 10) | | LDL Very Small nmol/L | LDL Small nmol/L | LDL Medium nmol/L | LDL Large nmol/L | HDL Total nmol/L | HDL Large nmol/L | IDL Total nmol/L | VLDL Total nmol/L |
|---|---|---|---|---|---|---|---|---|---|
| Sample 1 | Mean | 283 | 267 | 310 | 479 | 22065 | 6188 | 362 | 160 |
|  | Stdv | 42 | 34 | 34 | 76 | 2860 | 980 | 50 | 14 |
|  | %CV | 15 | 13 | 11 | 16 | 13 | 16 | 14 | 9 |
| Sample 2 | Mean | 208 | 261 | 460 | 829 | 18374 | 5704 | 415 | 92 |
|  | Stdv | 20 | 18 | 29 | 81 | 1330 | 381 | 36 | 7 |
|  | %CV | 10 | 7 | 6 | 10 | 7 | 7 | 9 | 7 |
| Sample 3 | Mean | 205 | 153 | 177 | 477 | 19152 | 5926 | 350 | 72 |
|  | Stdv | 18 | 18 | 28 | 82 | 648 | 262 | 53 | 9 |
|  | %CV | 9 | 12 | 16 | 17 | 3 | 4 | 15 | 12 |
| Sample 4 | Mean | 214 | 171 | 208 | 482 | 18268 | 5414 | 283 | 64 |
|  | Stdv | 25 | 21 | 20 | 44 | 1886 | 400 | 25 | 6 |
|  | %CV | 12 | 12 | 10 | 9 | 10 | 7 | 9 | 10 |
| Sample 5 | Mean | 327 | 489 | 557 | 981 | 21586 | 5778 | 618 | 132 |
|  | Stdv | 39 | 38 | 36 | 80 | 2012 | 628 | 25 | 10 |
|  | %CV | 12 | 8 | 6 | 8 | 9 | 11 | 4 | 7 |
| Sample 6 | Mean | 186 | 152 | 196 | 535 | 25201 | 9157 | 495 | 92 |
|  | Stdv | 6 | 11 | 9 | 25 | 2689 | 690 | 34 | 8 |
|  | %CV | 3 | 7 | 5 | 5 | 11 | 8 | 7 | 9 |

FIG. 22A

|  | HDL S | HDL L | HDL Total | HDL Large | Inter Zone | Peak Diam | IDL Total |
|---|---|---|---|---|---|---|---|
| AVE n=20 | 0.033 | 0.019 | 0.051 | 0.019 | 0.007 | 0.173 | 0.003 |
| SD | 0.027 | 0.013 | 0.032 | 0.013 | 0.008 | 0.012 | 0.005 |
| LOB mean+2SD | 0.087 | 0.046 | 0.115 | 0.046 | 0.023 | 0.197 | 0.013 |
| LOQ mean+10SD | 0.302 | 0.153 | 0.370 | 0.153 | 0.088 | 0.293 | 0.052 |
| LOD mean+4SD | 0.141 | 0.072 | 0.179 | 0.072 | 0.039 | 0.221 | 0.022 |

|  | Non-HDL Total | LDL Very Small | LDL Small | LDL Medium | LDL Large | LDL Med + SM | LDL Total |
|---|---|---|---|---|---|---|---|
| AVE n=20 | 0.021 | 0.003 | 0.002 | 0.000 | 0.002 | 0.002 | 0.008 |
| SD | 0.014 | 0.006 | 0.006 | 0.000 | 0.006 | 0.006 | 0.011 |
| LOB mean+2SD | 0.048 | 0.016 | 0.013 | 0.001 | 0.015 | 0.013 | 0.029 |
| LOQ mean+10SD | 0.159 | 0.066 | 0.059 | 0.002 | 0.064 | 0.059 | 0.114 |
| LOD mean+4SD | 0.076 | 0.028 | 0.025 | 0.001 | 0.027 | 0.025 | 0.050 |

|  | LDL 4C | LDL 4B | LDL 4A | LDL 3B | LDL 3A | LDL 2B | LDL 2A | LDL 1 |
|---|---|---|---|---|---|---|---|---|
| AVE | 0.000 | 0.001 | 0.001 | 0.001 | 0.002 | 0.000 | 0.001 | 0.002 |
| SD | 0.000 | 0.003 | 0.004 | 0.002 | 0.006 | 0.000 | 0.002 | 0.005 |
| LOB | 0.001 | 0.007 | 0.010 | 0.005 | 0.013 | 0.001 | 0.005 | 0.012 |
| LOQ | 0.003 | 0.029 | 0.045 | 0.022 | 0.059 | 0.002 | 0.020 | 0.054 |
| LOD | 0.001 | 0.012 | 0.019 | 0.009 | 0.025 | 0.001 | 0.008 | 0.023 |

FIG. 22B

|  | IDL 2 | IDL 1 | VLDL S | VLDL M | VLDL L | VLDL Total |
|---|---|---|---|---|---|---|
| AVE | 0.001 | 0.001 | 0.001 | 0.006 | 0.003 | 0.010 |
| SD | 0.005 | 0.003 | 0.003 | 0.009 | 0.006 | 0.011 |
| LOB | 0.010 | 0.007 | 0.007 | 0.025 | 0.015 | 0.032 |
| LOQ | 0.046 | 0.028 | 0.031 | 0.101 | 0.063 | 0.118 |
| LOD | 0.019 | 0.012 | 0.013 | 0.044 | 0.027 | 0.053 |

FIG. 24

| Sample Type | Original | Extract | % Remains | Sample Type | Original | Extract | % Remains | Sample Type | Original | Extract | % Remains |
|---|---|---|---|---|---|---|---|---|---|---|---|
| serum1 | 107 | 4.99 | 4.7 | EDTA1 | 870 | 35.94 | 4.1 | heparin1 | 533 | 18.64 | 3.5 |
| serum2 | 788 | 5.71 | 0.7 | EDTA2 | 1949 | 29.36 | 1.5 | heparin2 | 509 | 21.80 | 4.3 |
| serum3 | 177 | 4.95 | 2.8 | EDTA3 | 4148 | 37.13 | 0.9 | heparin3 | 495 | 31.38 | 6.3 |
| serum4 | 246 | 4.66 | 1.9 | EDTA4 | 910 | 19.55 | 2.1 | heparin4 | 462 | 19.18 | 4.2 |
| serum5 | 707 | 6.29 | 0.9 | EDTA5 | 1488 | 37.02 | 2.5 | heparin5 | 2593 | 35.02 | 1.4 |
| serum6 | 737 | 7.27 | 1.0 | EDTA6 | 1727 | 24.68 | 1.4 | heparin6 | 1782 | 18.06 | 1.0 |
|  | Avg. |  | 2.0 |  | Avg. |  | 2.1 |  | Avg. |  | 3.4 |

MAGNETIC SEPARATION OF LIPOPROTEINS USING DEXTRAN SULFATE

CROSS-REFERENCE TO RELATED APPLICATIONS

This application claims priority to U.S. Application Ser. No. 61/428,812, filed Dec. 30, 2010, incorporated by reference herein in its entirety.

FIELD OF THE INVENTION

The present invention generally relates to the fields of particle size analysis and analyses of biological particles including lipoproteins for diagnostic purposes utilizing ion mobility measurement devices and methods. The present invention further provides methods and apparatus for purification and isolation of biomolecules including, without limitation, lipoproteins and biological complexes containing lipoproteins.

BACKGROUND OF THE INVENTION

The following description is provided solely to assist the understanding of the present invention. None of the references cited or information provided is admitted to be prior art to the present invention.

Cardiovascular disease is the leading cause of death in the United States. The most commonly used and accepted methods for determining risk of future heart disease include determining serum levels of cholesterol and lipoproteins, in addition to patient demographics and current health. There are well established recommendations for cut-off values for biochemical markers, including, for example without limitation, cholesterol and lipoprotein levels, for determining risk. However, cholesterol and lipoprotein cannot be the only risk factors because as many as 50% of people who are at risk for premature heart disease are currently not encompassed by the ATP III guidelines (i.e., Adult Treatment Panel III guidelines issued by the National Cholesterol Education Program and the National Heart, Lung and Blood Institute).

Methods to measure lipoprotein and other lipids in the blood include, for example, evaluating fasting total cholesterol, triglyceride, HDL (high density lipoprotein), and/or LDL (low density lipoprotein) cholesterol concentrations. Currently, the most widely used method for measuring LDL cholesterol is the indirect Friedewald method (Friedewald, et al., *Clin. Chem.*, 1972, 18:499-502). The Friedewald assay method requires three steps: 1) determination of plasma triglyceride (TG) and total cholesterol (TC), 2) precipitation of VLDL (very low density lipoprotein) and LDL (low density lipoprotein), and 3) quantitation of HDL cholesterol (HDLC). Using an estimate for VLDLC as one-fifth of plasma triglycerides, the LDL cholesterol concentration (LDLC) is calculated by the formula: LDLC=TC−(HDLC+VLDLC). While generally useful, the Friedewald method is of limited accuracy in certain cases. For example, errors can occur in any of the three steps, in part because this method requires that different procedures be used in each step. Furthermore, the Friedewald method is to a degree indirect, as it presumes that VLDLC concentration is one-fifth that of plasma triglycerides. Accordingly, when the VLDL of some patients deviates from this ratio, further inaccuracies occur.

Another method for evaluating blood lipoproteins contemplates measurement of lipoprotein size and density. The size distribution of lipoproteins varies among individuals due to both genetic and non-genetic influences. The diameters of lipoproteins typically range from about 7 nm to about 120 nm. In this diameter size range, there exist subfractions of the particles that are important predictors of cardiovascular disease. For example, VLDL transports triglycerides in the blood stream; thus, high VLDL levels in the blood stream are indicative of hypertriglyceridemia. These subfractions can be identified by analytical techniques that display the quantity of material as a function of lipoprotein size or density.

Regarding lipoprotein density analysis, ultracentrifugally isolated lipoproteins can be analyzed for flotation properties by analytic ultracentrifugation in different salt density backgrounds, allowing for the determination of hydrated LDL density, as shown in Lindgren, et al, *Blood Lipids and Lipoproteins: Quantitation Composition and Metabolism*, Ed. G. L. Nelson, Wiley, 1992, p. 181-274, which is incorporated herein by reference. For example, the LDL class can be further divided into seven subclasses based on density or diameter by using a preparative separation technique known as equilibrium density gradient ultracentrifugation. It is known that elevated levels of specific LDL subclasses, LDL-IIIa, IIIb, IVa and IVb, correlates closely with increased risk for CHD (i.e., coronary heart disease), including atherosclerosis. Furthermore, determination of the total serum cholesterol level and the levels of cholesterol in the LDL and HDL fractions are routinely used as diagnostic tests for coronary heart disease risk. Lipoprotein class and subclass distribution is a more predictive test, however, since it is expensive and time-consuming, it is typically ordered by physicians only for a limited number of patients.

With respect to measurement of the sizes of lipoproteins, currently there is no single accepted method. Known methods for measuring the sizes of lipoproteins within a clinical setting include the vertical auto profile (VAP) (see e.g. Kulkarni, et al., *J. Lip. Res.*, 1994, 35:159-168) whereby a flow analyzer is used for the enzymatic analysis of cholesterol in lipoprotein classes separated by a short spin single vertical ultracentrifugation, with subsequent spectrophotometry and analysis of the resulting data.

Another method (see e.g. Jeyarajah, E. J. et al., *Clin Lab Med.*, 2006, 26:847-70) employs nuclear magnetic resonance (NMR) for determining the concentrations of lipoprotein subclasses. In this method, the NMR chemical shift spectrum of a blood plasma or serum sample is obtained. The observed spectrum of the entire plasma sample is then matched by computer means with known weighted sums of previously obtained NMR spectra of lipoprotein subclasses. The weight factors that give the best fit between the sample spectrum and the calculated spectrum are then used to estimate the concentrations of constituent lipoprotein subclasses in the blood sample.

Another method, electrophoretic gradient gel separation (see e.g. U.S. Pat. No. 5,925,229; incorporated by reference herein) is a gradient gel electrophoresis procedure for the separation of LDL subclasses. The LDL fractions are separated by gradient gel electrophoresis, producing results that are comparable to those obtained by ultracentrifugation. This method generates a fine resolution of LDL subclasses, and is used principally by research laboratories. However, the gel separation method, which depends on uniform staining of all components that are subsequently optically measured, suffers from nonuniform chromogenicity. That is, not all lipoproteins stain equally well. Accordingly, the differential stain uptake can produce erroneous quantitative results. Additionally, the nonuniform chromogenicity can result in erroneous qualitative results, in that measured peaks may be skewed to a sufficient degree as to cause confusion of one class or subclass of lipoprotein with another. Furthermore, gradient gel electrophoresis can take many hours to complete.

Indeed, more recent methods for the quantitative and qualitative determination of lipoproteins from a biological sample have been described by Benner et al. (U.S. Pat. No. 7,259, 018; incorporated by reference herein) which methods employ particulate size and/or ion mobility devices.

SUMMARY OF THE INVENTION

The present invention provides apparati and methods for the preparation and analysis of differential charged-particle mobility analysis (also referred to herein as "ion mobility analysis") of lipoproteins utilizing a gas-phase electrophoretic-mobility molecular analyzer.

In one aspect, the invention provides methods for purifying lipoproteins for differential charged-particle mobility analysis, which methods do not include an immunoaffinity reagent (e.g., antibody), which methods include the following steps: a) admixing a solution containing lipoproteins and non-lipoproteins with one or more polyanionic compounds and one or more cations; b) allowing a precipitate containing lipoproteins to form in the admixed solution; and c) after step b), collecting the precipitated lipoproteins and subjecting the precipitated lipoproteins to differential charged-particle analysis after resolubilization. In some embodiments, the cations are divalent cations. In some embodiments, the lipoproteins are selected from the group consisting of HDL, LDL, Lp(a), IDL and VLDL.

In one aspect, the invention provides a method for purifying lipoproteins suitable for differential charged-particle mobility analysis of lipoprotein class and subclass, said method comprising: (a) adding one or more cations and dextran sulfate to the sample to form a precipitation mixture; (b) contacting the precipitation mixture with an insoluble solid support, wherein one or more classes or subclasses of lipoproteins from said sample precipitate from said mixture onto said solid support; (c) separating the precipitated lipoproteins on the solid support from said mixture; and (d) removing the precipitated lipoproteins from the solid support; wherein the dextran sulfate is not biotinylated and the precipitated lipoproteins are not bound to the solid support by streptavidin.

In some embodiments of the foregoing aspects, the method comprises adding glycine to the sample. In some embodiments, the sample is exposed to ethanol prior to step (a) under conditions suitable to precipitate fibrinogen in the sample. In some embodiments, the sample is plasma or serum.

In some embodiments, the cations are divalent cations. In some embodiments, the cations may be selected from the group consisting of $Mg^{2+}$, $Ca^{2+}$, $Mn^{2+}$, and $Sr^{2+}$. In some embodiments, one or more cations comprise $Ca^{2+}$; such as at a concentration within the range of about 24 mM to about 200 mM; such as at a concentration of about 150 mM. In some embodiments, the one or more cations comprise $Mg^{2+}$; such as at a concentration within the range of about 24 mM to about 200 mM; such as at a concentration of about 100 mM.

In some embodiments, the one or more cations comprise $Ca^{2+}$ and $Mg^{2+}$; such as $Ca^{2+}$ at a concentration within the range of about 24 mM to about 200 mM, and $Mg^{2+}$ at a concentration within the range of about 24 mM to about 200 mM; such as $Ca^{2+}$ at a concentration of about 25 mM, and $Mg^{2+}$ at a concentration of about 100 mM.

In some embodiments, the dextran sulfate is in the size range of about 10 to about 500 kDa. In some embodiments, the dextran sulfate is in the size range of about 50 to about 100 kDa. In some embodiments, the dextran sulfate has a size of about 50 kDa.

In some embodiments, the insoluble solid support comprises microbeads. In some embodiments, the microbeads are in the size range of about 0.2 µm to about 150 µm. In some embodiments, the microbeads comprise a magnetic or paramagnetic core. In some embodiments, the microbeads comprise an inert outer layer.

In some embodiments, the lipoproteins are selected from the group consisting of HDL, LDL, IDL, Lp(a), and VLDL. In some embodiments, the lipoproteins comprise HDL and LDL.

In another aspect, the resulting purified lipoproteins from any of the purification methods presented herein may be used for analysis of size distribution of lipoproteins as follows: (i) providing one or more lipoproteins in accordance with the purification methods described herein; and (ii) subjecting the one or more purified lipoproteins to differential charged-particle mobility analysis, thereby determining the size distribution of said lipoproteins. In some embodiments, the one or more lipoproteins are selected from the group consisting of HDL, LDL, Lp(a), IDL and VLDL. In some embodiments, the one or more lipoproteins are from a plasma sample obtained from an individual. In related embodiments, the methods further comprise: (iii) using the determined lipoproteins size distribution to conduct an assessment of said individual, said assessment selected from the group consisting of lipid-related health risk, cardiovascular condition, risk of cardiovascular disease, and responsiveness to a therapeutic intervention.

As used herein, "centrifugation" refers to separation or analysis of substances in a solution as a function of density and density-related molecular weight by subjecting the solution to a centrifugal force generated by high-speed rotation in an appropriate instrument.

As used herein, "purify" and like terms refer to an increase in the relative concentration of a specified component with respect to other components. For example without limitation, removal of lipid from a lipoprotein solution constitutes purification of the lipoprotein fraction, at e.g. the expense of the lipid fraction. It is understood that "purifying" and like terms in the context of centrifugation refers to sufficient separation in a centrifuge tube following centrifugation to allow extraction of the separated components by methods well known in the art including, without limitation, aspiration and/or fractionation. Surprisingly, it has been found that reducing the density of lipoprotein-containing solutions prior to centrifugation for example, without limitation, by reducing the salt concentration thereof, results in enhanced recovery of certain fractions of lipoprotein, including LDL and HDL fractions.

The terms "lipoprotein" and "lipoprotein particle" as used herein refer to particles obtained from mammalian blood which include apolipoproteins biologically assembled with noncovalent bonds to package for example, without limitation, cholesterol and other lipids. Lipoproteins preferably refer to biological particles having a size range of about 7 to 120 nm, and include VLDL (very low density lipoproteins), IDL (intermediate density lipoproteins), LDL (low density lipoproteins), Lp(a) [lipoprotein (a)], HDL (high density lipoproteins) and chylomicrons as defined herein.

The term "apolipoprotein" as used herein refers to lipid-binding proteins which constitute lipoproteins. Apolipoproteins are classified in five major classes: Apo A, Apo B, Apo C, Apo D, and Apo E, as known in the art.

The term "biological particle" as used herein refers to a material having a non-covalently bound assembly of molecules derived from a living source. Examples without limitation of biological particles include lipoproteins assembled for example from apolipoproteins and lipids; viral components assembled from non-covalently bound coat proteins and glycoproteins; immune complexes assembled from antibodies and their cognate antigens, and the like.

The terms "marker," "biochemical marker" and like terms as used herein refer to naturally occurring biomolecules (or derivatives thereof) with known correlations to a disease or condition.

The term "about" as used herein in the context of a numerical value represents the value +/−10% thereof.

In certain embodiments of the aspects contemplating isolation and/or purifying of lipoproteins described herein, the invention provides methods for analyzing the size distribution of lipoproteins, which methods include the following steps: (a) providing one or more lipoproteins in accordance with any of the methods described herein; and (b) subjecting one or more lipoproteins to charged-particle mobility analysis, thereby determining the size distribution of the lipoproteins. In some embodiments of the above aspects, methods are used to determine in a patient sample the concentration of HDL, LDL, IDL, and VLDL and more preferably HDL, LDL, IDL, VLDL and Lp(a). The patient sample is preferably plasma or serum. The methods as described herein may also include the use of an internal standard such as one or more labeled lipoproteins (e.g. fluorescent label) to monitor sample loss during processing so as to obtain more accurate determinations of lipoprotein concentration in the starting sample to be evaluated.

In another aspect, the invention provides methods for analyzing the size distribution of lipoproteins, which methods include the following steps: (a) determining a differential mobility particle size distribution in one or more regions of particle sizes for one or more lipoproteins subjected to differential charged-particle mobility analysis; (b) subtracting contribution to the particle size distribution of a non-lipoprotein reagent or a non-lipoprotein sample material to obtain a lipoprotein particle size distribution; and (c) outputting the lipoprotein particle size distribution to a display, a printer or a memory.

In another aspect, the invention provides a computer-readable medium including a computer code stored thereon, the computer code for analyzing the size distribution of lipoproteins includes (a) determining a differential mobility particle size distribution in one or more regions of particle sizes for one or more lipoproteins subjected to differential charged-particle mobility analysis; (b) subtracting contribution to the particle size distribution of a non-lipoprotein reagent or a non-lipoprotein sample material to obtain a lipoprotein particle size distribution; and (c) outputting the lipoprotein size distribution to a display, a printer or a memory.

In another aspect, the invention provides apparatus for differential charged-particle mobility analysis including (a) one or more pumps adapted to transport sample through a capillary, (b) an ionizer adapted to charge particles of the sample as the sample flows within the capillary, and (c) an ion mobility analyzer adapted to perform a differential charged-particle mobility analysis on the sample of charged particles. The ionizer may include a conductive union around a part of the capillary. In one embodiment, the conductive union forms a microtite region in a part of the capillary and applies a charge to the sample flowing therethrough, thereby charging particles of the sample.

Certain embodiments of the apparatus further comprise an autosampler adapted to provide a sample for differential charged-particle mobility analysis to one or more pumps.

In some embodiments, one or more pumps may include a high-flow pump adapted to provide the sample to a nanoflow pump, the nanoflow pump being adapted to provide the sample to the capillary. The high-flow pump may pump sample at a rate of approximately 5-20 microliters per minute, and the nanoflow pump may pump the sample at a rate of approximately 100-250 nanoliters per minute.

BRIEF DESCRIPTION OF THE DRAWINGS

FIG. 11A shows ion mobility profiles of LDL recovered from two serum samples. Lipoprotein was recovered using biotinylated dextran sulfate and streptavidin-coated magnetic beads. FIG. 11B shows ion mobility profiles of HDL recovered from four samples, using either dextran sulfate and low speed centrifugation or biotinylated dextran sulfate and streptavidin-coated magnetic beads. Details are described in Example 9

FIGS. 15A and 15B show ion mobility profiles of lipoprotein recovered from serum using different sizes of dextran sulfate and magnetic beads. FIG. 15A shows the ion mobility profiles of samples processed using 10 kD and 20 kD dextran sulfate. FIG. 15B shows the ion mobility profiles of samples processed using 100 kD and 500 kD dextran sulfate. Details are described in Example 13.

FIG. 20A shows a table of summary data for a study of intra-assay precision of lipoprotein separation and analysis using ion mobility.

FIG. 21A shows a summary table for statistical measures of inter-assay variation of lipoprotein separation and analysis using ion mobility.

FIGS. 22A and B shows a table summarizing data on detection limits of lipoprotein separation and analysis using ion mobility. Details are described in Example 27.

FIG. 24 shows a table summarizing data on fibrinogen removal from serum samples using dextran sulfate and magnetic beads. Details are described in Example 29.

DETAILED DESCRIPTION OF THE INVENTION

Figure 1:
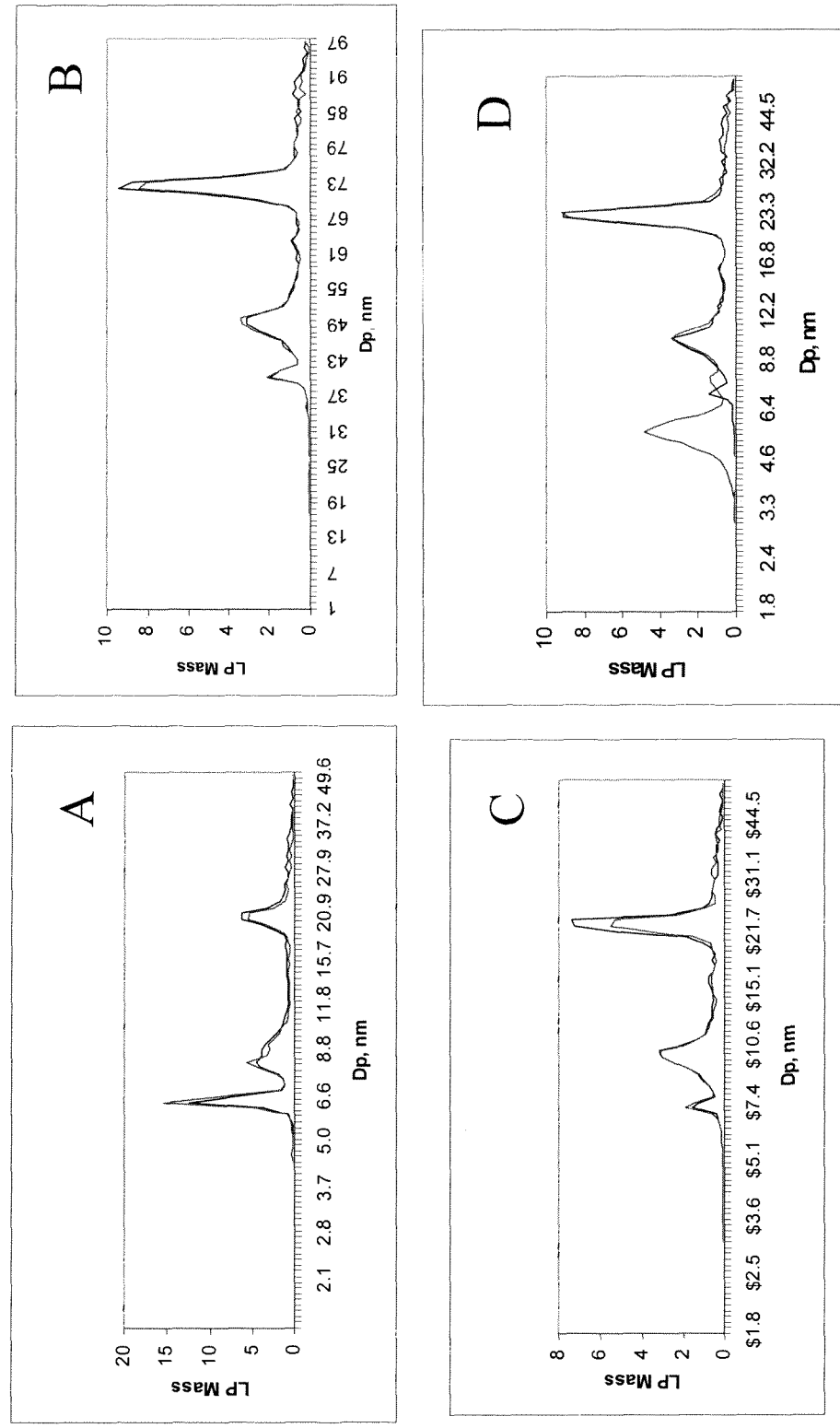
FIG. 1 shows the effect of density on lipoprotein recovery from a plasma sample during a 3.7 hr ultracentrifugation. Samples were prepared in duplicate using different density solutions and centrifugation for 3.7 hr. After collecting the lipoprotein fraction, it was dialyzed before analysis by differential charged-particle mobility. Each panel shows the profile of each replicate. Solution densities: A=1.23 g/mL; B=1.181 g/mL; C=1.170 g/mL; D=1.165 g/mL The abscissa is lipoprotein diameter (nm), and the ordinate is an arbitrarily scaled mass coordinate, which mass coordinate is linearly related to the actual number of particles counted as a function of size (i.e., diameter).

"VLDL, IDL, LDL, and HDL" refer to classifications of lipoproteins as shown in Table 1. It is understood that the values used in Table 1 for sizes are determined by gel electrophoresis methods, as known in the art. With the differential charged-particle mobility analysis methods disclosed here, it has been observed that all measurements of lipoprotein diameter obtained with differential charged-particle mobility analysis are shifted to smaller diameters compared to the data obtained with gel electrophoresis. Without wishing to be bound by any theory, it is believed that this difference is due to calibration of the gels. The shift appears to be linearly related and approximated by the following formula:

$$0.86 * \text{gel diameter} = IM \text{ diameter}$$

Table 1 describes the standard classes and subclass designations assigned to various lipoprotein fractions using traditional gel electrophoresis measurements: very low density lipoproteins (VLDLs) with subclasses VLDL I and II; intermediate density lipoproteins (IDLs) with subclasses IDL I and II; low density lipoproteins (LDLs) with subclasses I, IIa, IIb, IIIa, IIIb, IVa and IVb; and high density lipoproteins (HDLs), which typically includes several subclasses, such as HDL IIa, IIb, IIIa, IIIb, and IIIc.

TABLE 1

| Major Lipoprotein Class, Subclass, Density and Particle Size | | |
|---|---|---|
| Class Acronym Subclass | Name Density (g/mL) | Particle Diameter (Å) |
| VLDL | Very Low Density Lipoprotein | |
| I | <1.006 | 330-370 |
| II | 1.006-1.010 | 300-330 |
| IDL | Intermediate Density Lipoprotein | |
| I | 1.006-1.022 | 285-300 |
| II | 1.013-1.019 | 272-285 |
| LDL | Low Density Lipoprotein | |
| I | 1.019-1.023 | 272-285 |
| IIa | 1.023-1.028 | 265-272 |
| IIb | 1.028-1.034 | 256-265 |

TABLE 1-continued

Major Lipoprotein Class, Subclass, Density and Particle Size

| Class Acronym Subclass | Name Density (g/mL) | Particle Diameter (Å) |
|---|---|---|
| IIIa | 1.034-1.041 | 247-256 |
| IIIb | 1.041-1.044 | 242-247 |
| IVa | 1.044-1.051 | 233-242 |
| IVb | 1.051-1.063 | 220-233 |
| HDL | High Density Lipoprotein | |
| IIa | 1.063-1.100 | 98-130 |
| IIb | 1.100-1.125 | 88-98 |
| IIIa | 1.125-1.147 | 82-88 |
| IIIb | 1.147-1.154 | 77-82 |
| IIIc | 1.154-1.203 | 72-77 |

Without wishing to be bound by any theory, it is believed that the observed differences between differential charged-particle mobility analysis diameters and gel electrophoresis diameters may also be due to distortion of lipoproteins interacting with the gel matrix under the influence of the intrinsic impressed electric field of the electrophoresis gel. The size difference may also be due to historical data used to convert particle density (obtained from analytic ultracentrifuge separations) to particle size obtained from electron microscopy.

As used herein, "chylomicrons" means biological particles of size 70-120 nm, with corresponding densities of less than 1.006 g/mL. Chylomicrons have not been found to have any clinical significance in the prediction of heart disease, for example, coronary heart disease (CHD).

"Apo A" as known in the art is a protein component of HDL. "Apo B" is a protein component of LDL, IDL, Lp(a), and VLDL, and indeed is the primary apolipoprotein of lower density lipoproteins, having human genetic locus 2p24-p23, as known in the art.

"Lp(a)," and "lipoprotein (a)" refer to a type of lipoprotein found in serum having a molecular composition distinct from IDL and LDL, which is found in complex with apolipoprotein a [apo(a)]. Lp(a) has a particle size that overlaps with LDL and IDL and therefore can interfere with particle size analysis when Lp(a) particles are present in the sample. Although some patients have naturally occurring low Lp(a) concentrations, it is believed to be good practice to remove the Lp(a) prior to LDL size measurements. Alternatively, LDL and IDL are measured with the Lp(a) still present in the sample, and any Lp(a) contributes to the particles detected in these size ranges.

The present invention contemplates apparatus and methods for use in differential charged-particle mobility, and preparation of samples for differential charged-particle mobility. Differential charged-particle mobility utilizes the principle that particles of a given size and charge state behave in a predictable manner when carried in a laminar-air flow passed through an electric field. Accordingly, differential charged-particle mobility analysis is a technique to determine the size of a charged particle undergoing analysis when the charged particle is exposed to an electric field.

Electrical mobility is a physical property of an ion and is related to the velocity an ion acquires when it is subjected to an electrical field. Electrical mobility, Z, is defined as $$Z = \frac{V}{E} \qquad (1)$$

where V=terminal velocity and E=electrical field causing particle motion. Particle diameter can be obtained from $$Z = \frac{neC_c}{3\pi\eta d} \qquad (2)$$

where n=number of charges on the particle (in this case a single charge), $e=1.6. \times .10^{-19}$ coulombs/charge, $C_c$=particle size dependent slip correction factor, $\eta$=gas viscosity, and d=particle diameter. Accordingly, solving for d, provides the following relationship:

$$d = \frac{neC_c}{3\pi\eta}\frac{E}{V}. \qquad (3)$$

Thus, an explicit relationship for particle diameter as a function of known parameters results. By setting the parameters to different values, different particle diameters of the charged particles may be selected as further described below and known in the art. In preferred methods of differential charged-particle mobility analysis, the electric field strength E acting upon the charged particle is varied during analysis.

In differential charged-particle mobility analysis, particles (e.g., lipoproteins and the like) are carried through the system using a series of laminar airflows. The lipoproteins in a volatile solution are introduced to an electrospray chamber containing approximately 5% to 15% $CO_2$ (such as about 12% $CO_2$) wherein the lipoproteins desolvate. In the electrospray chamber the desolvated, charged lipoproteins are neutralized by ionized air, introduced for example without limitation by an alpha particle emitter in the chamber. Based on Fuch's formula, a predictable proportion of particles emerge from the chamber carrying a single charge and are transported from the chamber to the Differential Mobility Analyzer (DMA). For details on Fuch's formula, reference is made to Fuchs, N. A.: *The Mechanics of Aerosols*, Macmillan, 1964. "Differential Mobility Analyzer," "DMA" and like terms refer to devices for classifying charged particles on the basis of ion electrical mobility, as known in the art and described herein. In differential charged-particle mobility analysis, when particles have a known uniform charge, the size of the particles classified may be determined from the mobility thereof. In the DMA the particles enter at the top outer surface of the chamber and are carried in a fast flowing laminar-air flow, (i.e., "the sheath flow"). The sheath flow is filtered (to remove particles) air that constantly recirculates through the DMA at a constant velocity in the range of about 15 L/min to about 20 L/min. As the particles pass through the DMA (carried in the sheath flow) the electric potential across the chamber is ramped up at a known rate. As the electrical potential changes, particles of different diameter are collected via a slit at the bottom inner surface of the chamber. Particles follow a non-linear path through the DMA depending on their charge and diameter. At any given electrical potential, particles of known size will follow a path that will allow them to pass through the collecting slit. Particles passing through the collecting slit are picked up by another, separate laminar-flow air stream and are carried to a particle counter. The particle counter enlarges the particles by condensation to a size that can be detected and counted for example by a laser detection system. Knowing the electrical potential being applied to the DMA when the particle was collected permits the accurate determination of the particle diameter and the number of particles present at that size. This data is collected and stored in bins as a function of time for different particle size. In this way the number of particles of any given size range can be determined and converted to a concentration of particles based on the time required to collect the data, the flow rate of sample being introduced into the electrospray device, and the number of charged particles at that size.

In methods of the present invention contemplating isolation and/or purification of lipoproteins, initial sample collection and preparation may be conducted by methods well known in the art. Typically, a 2-5 ml fasting blood specimen is initially taken. Chylomicrons are not typically present in subjects who have been fasting for a period of at least 12 hours; thus, overlap of VLDL sizes and chylomicron sizes is eliminated by fasting. The specimen is then initially spun in a centrifuge (e.g., clinical centrifuge) preferably for approximately 10 minutes at approximately 2000×G, which centrifugation is sufficient to remove the cellular components from the specimen. During this process, the more dense cellular components stratify at the bottom of the sample. A remaining less dense plasma specimen containing lipoproteins on top is then drawn off using methods well known in the art, e.g., aspiration.

Historically, in preparation for centrifugation, a plasma specimen could be density-adjusted to a specific density using high purity solutions or solids of inorganic salts, e.g., sodium chloride (NaCl), sodium bromide (NaBr) and the like. In some previous protocols, the specific density would be chosen to be greater than or equal to the highest density of the lipoprotein material to be analyzed, so that the lipoprotein material would float when density stratified. "Density stratified" and like terms refer to the layering of components in a solution subjected to centrifugation. These densities are tabulated in Table 1. The density-adjusted sample could then be ultracentrifuged for example for approximately 18 hours at 100,000×G to separate the non-lipoprotein proteins from the lipoproteins. Non-lipoprotein proteins, particularly albumin, could be removed from the plasma specimen, preferably by ultracentrifugation. The lipoproteins would float to the top of the sample during ultracentrifugation. Accordingly, by sequentially centrifuging from lowest density to highest density of the density adjustment, the various classes and subclasses of lipoproteins could be sequentially extracted. Typically, a dialysis step would be required following extraction of a centrifuged sample to remove salts introduced for adjustment of density, which dialysis step would typically require 4-12 hrs under conditions well known in the art.

Conditions for centrifugation for lipoprotein-containing samples described herein are well known in the art of biochemical separation. For example without limitation, samples are typically centrifuged at 10° C. for 1-4 hrs at 223,000×G. In some embodiments, centrifugation employs centrifugal force of 50,000-100,000, 100,000-120,000, 120,000-150,000, 150,000-200,000, 200,000-230,000, 230,000-250,000×G, or even higher force. In some embodiments, the time of centrifugation is 1, 2, 2.2, 2.4, 2.6, 2.8, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18 hr, or even longer. Prior to analysis by differential charged-particle mobility, an aliquot of the lipid fraction is removed (e.g., 10-200 μL) from the top of the centrifuge tube and diluted (e.g., 1:800) in 25 mM ammonium acetate (AA), 0.5 mM ammonium hydroxide, pH 7.4. Advantageously, in some embodiments described herein, a dialysis step is not necessary in conjunction with methods of the invention, resulting in less time required for analysis.

In embodiments of the invention which contemplate lipoproteins, the lipoproteins are selected from the group consisting of HDL, LDL, IDL, Lp(a), and VLDL. In some embodiments, the lipoproteins are HDL.

In some embodiments of aspects provided herein which contemplate lipoproteins, the lipoproteins may derive from a plasma specimen, obtained by methods well known in the art or as described herein. The terms "biological specimen," "biological sample" and like terms refer to explanted, withdrawn or otherwise collected biological tissue or fluid including, for example without limitation, whole blood, serum and plasma. The term "plasma" in the context of blood refers to the fluid obtained upon separating whole blood into solid and liquid components. The term "serum" in the context of blood refers to the fluid obtained upon separating whole blood into solid and liquid components after it has been allowed to clot. In some embodiments of any of the aspects of the present invention, the biological specimen is of human origin. In some embodiments of any of aspects provided herein, the biological specimen is serum. In some embodiments of any of the aspects provided herein, the biological specimen is plasma.

In some embodiments of the invention which contemplate centrifugation, the centrifugation does not reach equilibrium. "Centrifugation equilibrium" and like terms refers to centrifugation conducted for sufficient time and at sufficient centrifugal force such that the components of the solution being centrifuged have reached neutral density buoyancy, as well known in the art. Surprisingly, it has been found that foreshortened centrifugation protocols, as described herein wherein centrifugal equilibrium is not reached, can nonetheless provide significant purification of lipoproteins.

In some embodiments of the invention which contemplate centrifugation of sample containing lipoproteins and non-lipoprotein components, purified lipoprotein is collected from the top portion of the centrifuge tube following centrifugation. "Top portion of the centrifuge tube" and like terms refer to the liquid in the upper portion of a centrifuge tube when viewed outside of the centrifuge rotor which may, but does not necessarily, include liquid at the very top.

Further any of the methods of the present invention directed to purifying lipoproteins, it has been surprisingly found that reduction of the density of the solution to a value less or equal to about 1.21 g/mL while centrifuging to less than equilibrium actually results in improved recovery, hence purification, of LDL and HDL.

Lipoprotein density can be determined directly by a variety of physical biochemical methods well known in the art, including without limitation equilibrium density ultracentrifugation and analytic ultracentrifugation. Lipoprotein density may also be determined indirectly based on particle size and a known relationship between particle size and density. Lipoprotein size may be determined by a variety of biochemical methods well known in the art including, without limitation, methods described herein.

Ion mobility, also known as ion electrical mobility or charged-particle mobility, analysis offers an advantage over the other methods described herein in that it not only measures the particle size accurately based on physical principles but also directly counts the number of particles present at each size, thereby offering a direct measurement of lipoprotein size and concentration for each lipoprotein. Ion mobility analysis has been used routinely in analyzing particles in aerosols, and analyzers suitable for ion mobility analysis have been adapted to analyze large biological macromolecules. Ion mobility analysis is a very sensitive and accurate methodology with, nonetheless, a drawback that ion mobility analysis measures all particles introduced into the system. Accordingly, it is of prime importance to isolate and/or purify the compounds of interest prior to analysis. Lipoproteins are candidates for this method because lipoproteins can be isolated from other serum proteins based on density and other features described herein.

Exemplary differential charged-particle mobility results for lipoproteins from plasma samples purified by centrifugation with varying densities of solution are shown in FIG. 1. In these experiments, serum samples (25 µL) were overlaid on a cushion (200 µL) of four different density salt (KBr) solutions. The densities of the solutions were 1.165, 1.170, 1.181, and 1.23 g/mL. Each sample was ultracentrifuged for a period of 3.7 hr at 223,000×G. The top 100 µL after the centrifugation was removed. Fractionated lipoprotein samples from each density were dialyzed overnight against ammonium acetate (25 mM), ammonium hydroxide (0.5 mM), pH 7.4. Following dialysis each sample was analyzed by differential charged-particle mobility with the resulting profiles shown in FIG. 1. A reduction is apparent in the lipoprotein profiles in the protein peak prior to the HDL region seen at the lower densities compared to 1.23 g/mL. Without wishing to be bound by any theory, this observation is believed due to more efficient removal of plasma proteins with lower salt solutions.

With further reference to FIG. 1, the abscissa is the particle size (i.e., diameter), and the ordinate is an arbitrarily scaled mass. The area under the curves, in a particle mass versus independent variable (such as size, density, mobility, etc.) distribution, is directly representative of the lipoprotein particle mass. The measurement technique relies on counting individual particles as a function of size (diameter). It is therefore possible to convert the number of particles at a specific size into a mass value using the volume and density of the particles. The density of lipoproteins is a well-known function of particle size and is obtainable for example from the literature. The mass values associated with the figure are simply scaled to indicate relative values but can be converted to actual mass of lipoproteins in plasma using dilution factors along with flow rates of sample and air passing through the ion mobility spectrometer. Accordingly, in some embodiments adjusting the density of a lipoprotein-containing solution prior to non-equilibrium centrifugation to a value lower than expected to separate the higher density lipoproteins (e.g., HDL) actually results in separation of HDL and LDL. Advantageously, the method of reducing the density of the lipoprotein-containing sample also results in increased separation from albumin.

In some embodiments of aspects provided herein contemplating centrifugation of a sample containing lipoproteins and non-lipoprotein components, the first solution comprises $D_2O$. In some embodiments, the density of the first solution is determined substantially by the content of $D_2O$, wherein the first solution has a density of 1.00 to about 1.10 g/mL. The density of $D_2O$ is approximately 1.107 gm/mL at 25° C. Accordingly, in some embodiments of the invention, the aqueous component includes 0-99% $D_2O$, or even higher. In some embodiments, the amount of $D_2O$ is in the range, for example without limitation, 10-99, 20-99, 30-99, 40-99, 50-99, 10-90, 20-90, 30-90, 40-90, 50-90%, and the like. In some embodiments, the content of $D_2O$ is a specific value, for example without limitation, about 1, 2, 5, 10, 20, 30, 40, 50, 60, 70, 80, 90, 95, 96, 97, 98, 99, or even 100% $D_2O$. In some embodiments, the first solution is substantially $D_2O$. The term "essentially $D_2O$" refers to $D_2O$ comprising the aqueous component with no additionally added $H_2O$. The terms "substantially $D_2O$" and like terms refer to $D_2O$ content in a range greater than 50%, for example without limitation, 55%, 60%, 65%, 70%, 75%, 80%, 85%, 90%, 95%, 99% or even 100% $D_2O$.

Figure 2:
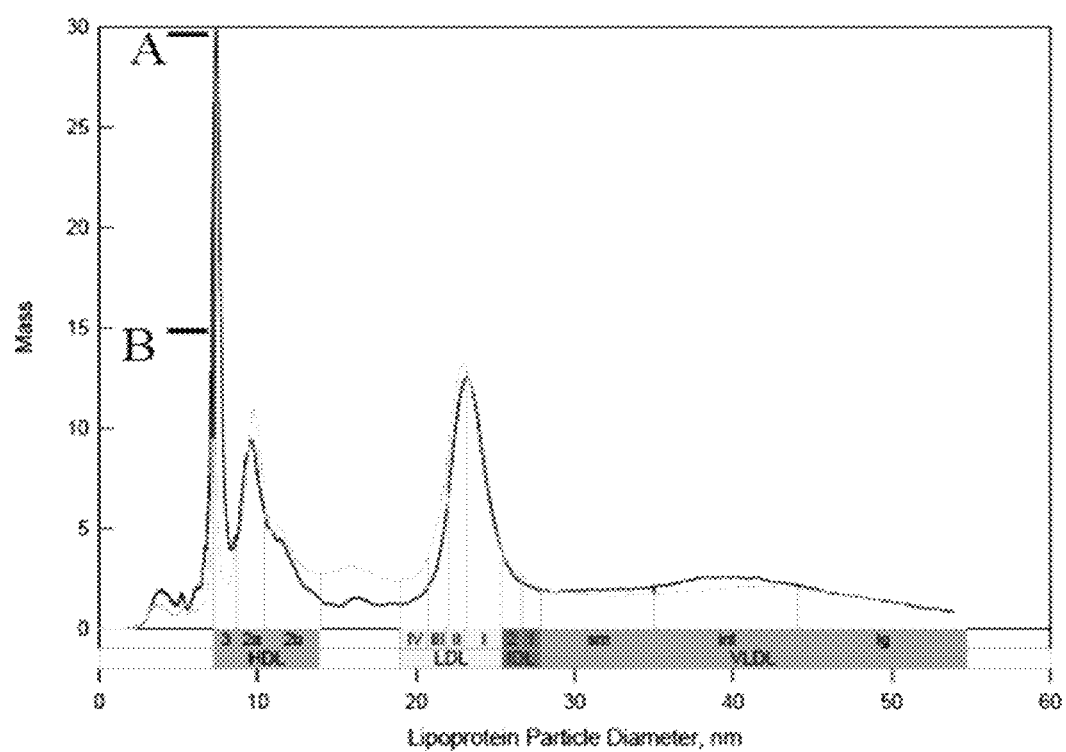
FIG. 2 shows a comparison of lipoprotein recovery from plasma using either a $D_2O$ or a low salt protocol (without $D_2O$) in a centrifugation separation experiment. Dark profile reflects a 2 hr centrifugation using $D_2O$ as the dense solution (1.107 g/mL). Light profile reflects a 3.7 hr centrifugation using KBr as the dense solution (1.151 g/mL). A—indicates peak height of albumin for 2 hr centrifugation; B—indicates the albumin peak height for 3.7 hr centrifugation. The abscissa is lipoprotein diameter (nm), and the ordinate is an arbitrarily scaled mass coordinate, as discussed in the legend for FIG. 1.

In some embodiments of this aspect, the lipoprotein-containing sample includes little if any added salt. With reference to FIG. 2 (experimental conditions provided in Example 1), which shows the result of a centrifugation procedure conducted using $D_2O$ and no additional salts for density adjustment, and a low-density salt solution without $D_2O$, approximately equivalent recovery of LDL and certain HDL fractions (e.g., HDL-IIb and HDL-IIa) was observed after 2 hrs ($D_2O$) and 3.7 hrs (low-density salt solution). With further reference to FIG. 2, the profiles for $D_2O$ and low-density salt centrifugation procedures result in similar profiles, with nonetheless increased albumin (peak at start of HDL 3 region) judged due to decreased centrifugation time with the $D_2O$ sample. Without wishing to be bound by any theory, it appears that reduction of salt content with concomitant increase in density using $D_2O$ results in shorter time required for centrifugation and purification of lipoprotein from a lipoprotein-containing sample.

Figure 3:
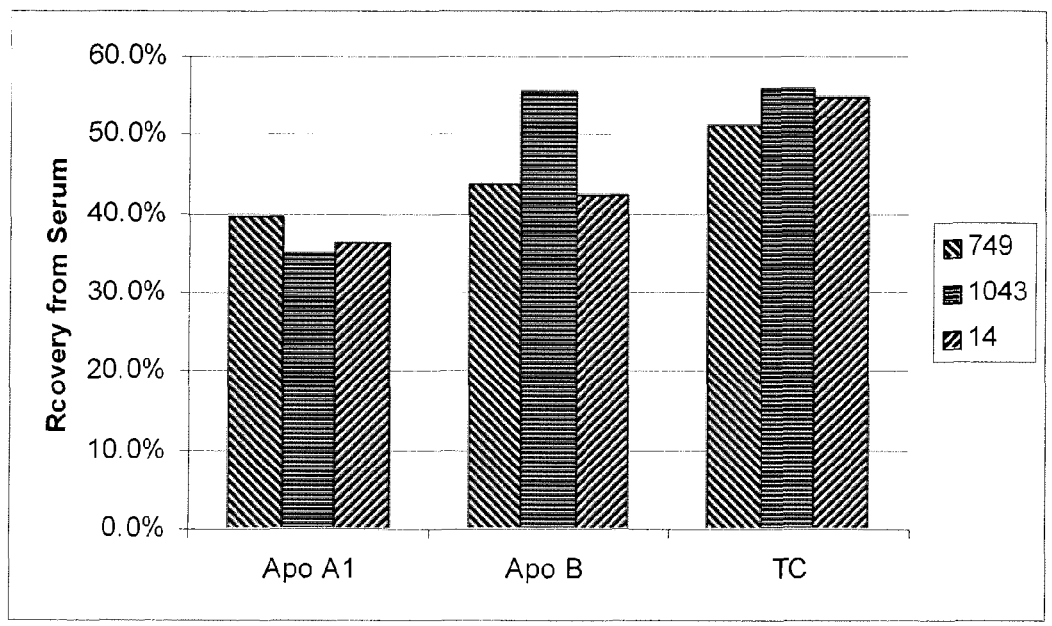
FIG. 3 shows the result of Apo A1, Apo B and total cholesterol (TC) recovery from plasma using $D_2O$ in combination with RGD/DS [RGD: Reactive Green 19 (RG 19) conjugated with dextran sulfate; RGD/DS: RGD in combination with DS] in a centrifugation separation experiment. Abscissa indicates analyte measured. Numbers associated with each box refer to a unique patient identification numbering system.

With reference to FIG. 3, under the conditions employed for FIG. 3 (experimental conditions of Example 2) approximately equal recovery of Apo A1 and Apo B after centrifugation are observed, indicating that lower density obtained with $D_2O$ does not result in selective recovery of larger less dense particles.

In some embodiments of the method of the present invention directed to purifying lipoproteins by the placement of a less dense solution above and adjacent to a lipoprotein-containing sample solution prior to centrifugation, a single density adjustment of the lipoprotein-containing solution is conducted using inorganic salts, preferably NaCl and/or NaBr. For example, over this sample in a centrifuge tube can be layered a second solution having density less than the density of the lipoprotein-containing sample solution. Alternatively, the lipoprotein-containing sample solution can be introduced under the second solution in the centrifuge tube. The lipoprotein-containing sample density adjustment can be selected within the range of 1.00 to about 1.21 g/mL according to the densities in Table 1 to separate a class of lipoproteins having equal or lesser density. The density of the second solution can be selected within the range 1.00 g/mL up to just less than the density of the lipoprotein-containing sample solution, preferably in the range 1.00 to about 1.15 g/mL, more preferably 1.00 g/mL. In this manner, the HDL, IDL, LDL, Lp(a) and VLDL lipoproteins having densities less than the density of the lipoprotein-containing sample solution can be simultaneously extracted. Surprisingly, it has been found that providing a lipoprotein-containing solution in a centrifuge tube with a solution having lower density above and adjacent the lipoprotein-containing solution results in enhanced recovery of lipoprotein employing centrifugal separation. In preferred embodiments, lipoprotein containing fractions are withdrawn from the very top of the tube, at the meniscus, downward to the appropriate desired volume.

Further to these methods, it has been found that the time required for centrifugal separation of a lipoprotein-containing sample is reduced in lower density samples when compared to a corresponding period of time required for higher density samples. The terms "corresponding period of time" and the like in the context of centrifugal separation refer to the length of time of centrifugation required to achieve a specified level of separation, given equivalent centrifugal force during the centrifugation. For example without limitation, it has been found that at least 2 hrs centrifugation (at e.g., 230,000×G) is required to remove sufficient albumin from a typical lipoprotein-containing sample, with less centrifugation time resulting in less removal of albumin. Without wishing to be bound by any theory, it appears that by lowering the density of the sample, albumin, and indeed other non-lipoprotein plasma proteins, are more readily stratified and thus separated from lipoprotein. Accordingly, a key factor in optimizing purification of lipoprotein is shortening the time of centrifugation to maximize the loss of albumin and other plasma proteins while retaining HDL.

In some embodiments of aspects provided herein which contemplate centrifugation of sample containing lipoproteins and non-lipoprotein components, the sample further comprises a compound which can act as a precipitant for selected lipoprotein components therein, as known in the art. "Precipitant" refers to a compound which may cause or promote precipitation of a biomolecule upon addition to a solution of such biomolecule. A precipitant may require an additional agent to afford precipitation. "Additional agent to afford precipitation" and like terms refer to compounds which act with a precipitant and may be required to afford precipitation by the precipitant. Exemplary precipitants include, without limitation, salts of charged inorganic ions, preferably ammonium sulfate, antibodies, charged polymers (e.g., DS and the like) optionally in the presence of ionic species (e.g., divalent cations), lectins, and the like. In some embodiments, the precipitant is present albeit under conditions (e.g., pH, concentration, lack of necessary additional agents, and the like) wherein lipoproteins are not precipitated. In some embodiments, the precipitant is DS. In some embodiments, the precipitant is DS, and the necessary additional agent is a divalent cation. In some embodiments, the lipoprotein-containing sample comprises DS but lacks divalent cations. Without wishing to be bound by any theory, it is believed that DS binds to particles which contain lipids in the presence of divalent cations, and that DS binding may interfere with non-specific binding interactions with resulting enhancement of recovery of certain lipoproteins. For example without limitation, it is observed that inclusion of DS significantly improved recovery of LDL from some preparations described herein.

In some embodiments of aspects provided herein which contemplate centrifugation of sample containing lipoproteins and non-lipoprotein components, the sample further comprises an albumin-binding compound under conditions suitable to allow formation of a complex comprising albumin and albumin-binding compound. Representative albumin-binding compounds include, without limitation, aromatic albumin-binding dyes. The aromatic albumin-binding dye may comprise a diazo dye; an alkali metal salt, alkaline earth metal salt, or amine salt of said diazo dye; a sulfonic acid dye; a physiologically-acceptable alkali metal salt, alkaline earth metal salt, or amine salt of said sulfonic acid dye; or mixtures thereof. Aromatic albumin-binding dyes particularly useful in the present invention include Reactive Blue 2, Evans Blue, Trypan Blue, Bromcresol Green, Bromcresol Purple, Methyl Orange, Procion red HE 3B, and the like. In certain embodiments, the albumin-binding compound is an analog of nicotinamide adenine dinucleotide (NAD). Representative NAD analogs suitable for use as albumin-binding compounds include, without limitation, RG 19, and Cibacrom Blue 3GA (CB 3GA).

In embodiments of the method contemplating the use of albumin-binding compounds, after mixture of the albumin-binding compound with a lipoprotein-containing sample, the sample is centrifuged as described herein. In some embodiments, the albumin-binding compound is conjugated with a chromatographic medium, which conjugate promotes facile removal of albumin complexed with albumin-binding compound for example, without limitation, by filtration. In some embodiments, the conjugated albumin-binding compound is observed to stratify at the bottom of the centrifuge tube, thereby facilitating removal (e.g., by aspiration, etc.) of the lipoprotein-containing fraction. In some embodiments wherein the albumin-binding compound is conjugated with a chromatographic medium, the chromatographic medium may be paramagnetic particles, agarose, dextran sulfate, or Sephadex®.

The term "microbead" as used herein refers to particles between 0.02 μm and 1000 μm in diameter comprising an inert material or comprising a core covered with an inert outer layer that can allow other molecules to be bound to the particle. Inert materials or outer layers can be made of, for example, silica, cellulose, polystyrene, polyacrylates, agarose, polyvinyl alcohols, or polyacrylamide, or combinations thereof. The core and the inert outer layer can be made of the same material or different materials. Microbeads can have a variety of molecules attached to the inert outer layer, including streptavidin, antibodies, oligonucleotides, or any ligand that specifically binds another molecule and can be covalently attached to the inert outer layer. Alternatively, the inert outer layer can have carboxylate, $NH_2$, or some other molecule attached which is normally used to covalently attach another molecule (such as a ligand) via a chemical reaction. As used in some embodiments presented herein, some microbeads are capable of binding to dextran sulfate via their inert outer layer, and do not require the presence of a specific ligand for binding.

The terms "paramagnetic particle" or "paramagnetic bead" (also referred to herein as "magnetic particle" or "magnetic bead") refers to particles or beads having a core made of magnetite or some other paramagnetic material and an inert outer layer that can allow other molecules to be bound to the particle. As used in some embodiments presented herein, some paramagnetic particles are capable of binding to dextran sulfate via their inert outer layer, and do not require the presence of a specific ligand for binding.

In further embodiments of the method contemplating the use of albumin-binding compounds, the albumin-binding compound is present during centrifugation at a concentration of up to 50 mg/mL, or even higher, without significant change in the quantity and relative proportion of the lipoproteins recovered from a plasma sample. For example, referring to FIG. 4, differential charged-particle mobility analyses of a lipoprotein-containing sample in which varying amounts of RG 19 were included prior to centrifugation show that inclusion of RG 19 conjugated with dextran sulfate (RGD) results in recovery of lipoprotein with little, if any, effect on the distribution of lipoproteins; compare FIG. 1 with FIG. 4. With reference to Example 3 and FIG. 4, while the differential charged-particle mobility profiles of HDL and LDL are similar, there is a decrease in the size of the peak (albumin) at the onset of the HDL 3 peak with increasing RGD concentration. Furthermore, the height of the peak at the higher concentrations is similar to that seen in preparations from lower density salt and 3.7 hr spins. In other embodiments, the concentration of albumin-binding compound is for example, without limitation, 1, 2, 5, 10, 15, 20, 25, 30, 35, 40, 45 or even 50 mg/mL.

Figure 5:
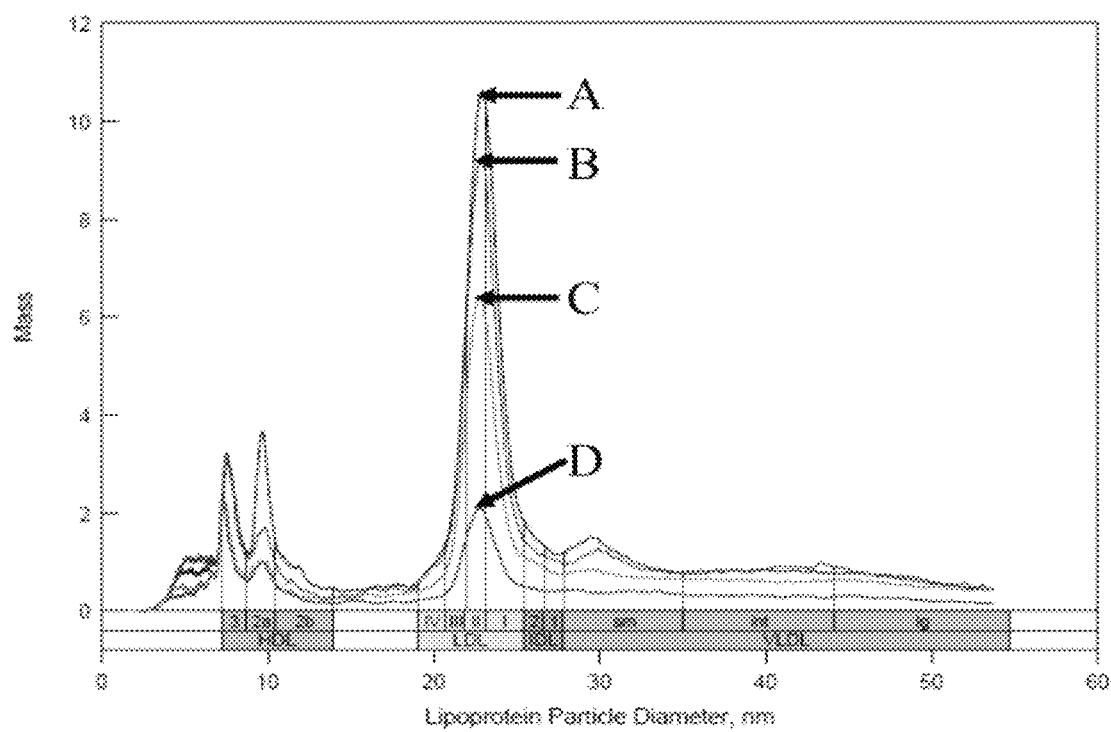
FIG. 5 shows the result of lipoprotein recovery from plasma after centrifugal purification with RGD and ethylenediaminetetracidic acid (EDTA), or with RGD/DS and EDTA, and optionally ammonium acetate (AA). Legend: (A) extraction with 7.5 mg/mL RGD and 2.5 mg/mL DS, dilution with 25 mM ammonium acetate with 5 µg/mL DS; (B) extraction with 7.5 mg/mL RGD and 2.5 mg/mL DS, dilution with 25 mM ammonium acetate; (C) extraction with 7.5 mg/mL RGD, dilution with 25 mM ammonium acetate with 5 µg/mL DS; (D) extraction with 7.5 mg/mL RGD, dilution with 25 mM ammonium acetate. The abscissa is lipoprotein diameter (nm), and the ordinate is an arbitrarily scaled mass coordinate, as discussed in the legend for FIG. 1.

In certain embodiments, the invention provides for the use of an albumin-binding compound in combination with DS. Referring to FIG. 5, use of RGD, optionally DS, and optionally ammonium acetate (AA), resulted in modulation of the recovery of LDL and HDL fractions as judged by differential charged-particle mobility analysis. With reference to Example 4 and FIG. 5, there are similarities in the HDL region of the profiles shown in FIG. 5 with increased recovery of HDL when DS is present in the extraction. Additionally, low albumin peak height is observed. It is believed that the increased peak in one preparation in HDL 2a (FIG. 5) is not typical of the reproducibility. Also of significance is the increased recovery of LDL. Without wishing to be bound by any theory, results herein suggest that DS present in the extraction and diluent affords the best recovery and reproducibility.

Figure 6:
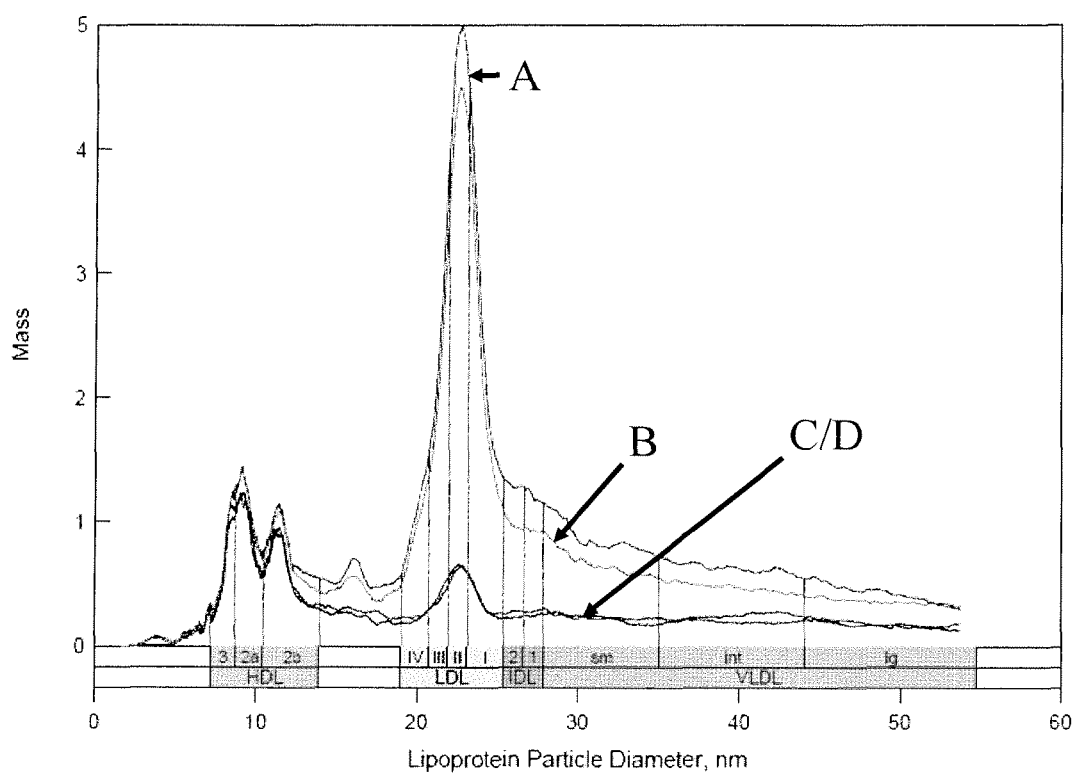
FIG. 6 shows the result of inclusion of DS in the dilution buffer following traditional density separation and dialysis. A and B: 5 µg/mL DS included in the ammonium acetate dilution buffer. C and D: no DS in the ammonium acetate dilution buffer. The abscissa is lipoprotein diameter (nm), and the ordinate is an arbitrarily scaled mass coordinate, as discussed in the legend for FIG. 1.

In certain embodiments, purified lipoprotein-containing sample obtained by methods of the invention are further diluted prior to differential charged-particle mobility analysis. Referring to FIG. 6 and Example 5, the effect of presence or absence of DS (+/−5 μg/mL) in a 1:200 dilution step with 25 mM ammonium acetate prior to differential charged-particle mobility analysis was assessed. As shown in FIG. 6, there is a significant increase in the LDL peak height in the presence of DS, whereas HDL peak profile are relatively unaffected.

In certain aspects and embodiments, the invention contemplates methods employing an albumin-binding compound conjugated with chromatographic media in combination with DS, and further in combination with a $D_2O$ solution under and adjacent a lipoprotein-containing sample in a centrifuge tube. A typical procedure employing this protocol is provided in Example 6.

In some embodiments of aspects provided herein which contemplate centrifugation of sample containing lipoproteins and non-lipoprotein components, the sample further comprises a non-lipoprotein capture ligand capable of binding non-lipoprotein component to form a non-lipoprotein/non-lipoprotein capture ligand complex, further wherein the centrifugation causes the non-lipoprotein/non-lipoprotein capture ligand complex to be separated from the lipoprotein components. "Non-lipoprotein capture ligand" and like terms refer to compounds which bind plasma components which are not lipoproteins. Exemplary non-lipoprotein capture ligands include, without limitation, antibodies and aptamers as understood in the art. For example without limitation, separation of antibody (i.e., as non-lipoprotein capture ligand) from antigen (i.e., non-lipoprotein) can be realized with a variety of methods including modulation of temperature, pH, salt concentration and the like. For further example without limitation, separation of aptamer (i.e., as non-lipoprotein capture ligand) from aptamer target (i.e., non-lipoprotein) can be realized with a variety of methods including modulation of temperature, pH, salt concentration, DNase or RNase and the like.

In some embodiments of aspects provided herein which contemplate centrifugation of sample containing lipoproteins and non-lipoprotein components, the sample further comprises a lipoprotein-capture ligand capable of binding lipoprotein component to form a lipoprotein/lipoprotein-capture ligand complex, further wherein the centrifugation causes the lipoprotein/lipoprotein-capture ligand complex to be separated from the non-lipoprotein components. "Lipoprotein-capture ligand" and like terms refer to compounds which bind lipoproteins. Exemplary lipoprotein-capture ligands include, without limitation, antibodies and aptamers as understood in the art. In preferred embodiments, the lipoprotein-capture ligand is an antibody.

In some embodiments of aspects provided herein which do not contemplate centrifugation of sample containing lipoproteins and non-lipoprotein components, the method contemplates a lipoprotein-capture ligand capable of binding lipoprotein component to form a lipoprotein/lipoprotein-capture ligand complex.

The term "aptamer" refers to macromolecules composed of nucleic acid, such as RNA or DNA, that bind tightly to a specific molecular target. The terms "bind," "binding" and the like refer to an interaction or complexation resulting in a complex sufficiently stable so as to permit separation. In some embodiments, the aptamer specifically bind Apo A1, Apo B, or Apo(a). Methods for the production and screening of aptamers useful for the present invention are well known in the art; see e.g., Griffin et al., U.S. Pat. No. 5,756,291, incorporated herein by reference in its entirety and for all purposes.

As practiced in the art, the method of selection (i.e., training) of aptamer requires a pool of single stranded random DNA oligomers comprising both random sequences and flanking regions of known sequence to serve as primer binding sites for subsequent polymerase chain reaction (PCR) amplification. Such DNA oligomers are generated using conventional synthetic methods well known in the art. As an initial and optional step, PCR amplification is conducted by conventional methods, and the amplified pool is left as duplex DNA, or used as single stranded DNA after strand separation. Optionally, transcription into RNA can be conducted. The term "oligomer pool" in this context refers to such single stranded or duplex DNA, or RNA transcribed therefrom. The term "refined oligomer pool" refers to an oligomer pool which has been subjected to at least one round of selection as described herein.

Further the aforementioned aptamer training, a "selection" step is conducted employing a column or other support matrix (i.e., target-coupled support) having target molecule attached thereon. Attachment, well known in the art, may be by covalent or non-covalent means. The oligomer pool, or refined oligomer pool, and target-coupled support are incubated in order to permit formation of oligonucleotide-target complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for target relative to a predecessor oligomer pool or refined oligomer pool.

Alternatively, the aforementioned aptamer training can employ a "reverse selection" step wherein aptamer is selected to bind to other constituents of the biological sample. In this case, a column or other support matrix is employed (i.e., constituent-coupled support) having other constituents of the biological sample attached thereon. The oligomer pool, or refined oligomer pool, and constituent-coupled support are incubated in order to permit formation of oligonucleotide-constituent complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for other constituents of the biological sample relative to a predecessor oligomer pool or refined oligomer pool. Examples of other constituents of the biological sample used in the reverse selection step include, without limitation, immunoglobulins and albumins.

In a typical production training scheme, oligonucleotide recovered after complexation with target or other constituent of the biological sample is subjected to PCR amplification. The selection/amplification steps are then repeated, typically three to six times, in order to provide refined oligomer pools with enhanced binding and specificity to target or other constituent of the biological sample. Amplified sequences so obtained can be cloned and sequenced. Optionally, when a plurality of individual aptamer sequence specific for a target having been obtained and sequenced, pairwise and multiple alignment examination, well known in the art, can result in the elucidation of "consensus sequences" wherein a nucleotide sequence or region of optionally contiguous nucleotides are identified, the presence of which correlates with aptamer binding to target. When a consensus sequence is identified, oligonucleotides that contain the consensus sequence may be made by conventional synthetic or recombinant means.

The term "antibody" refers to an immunoglobulin which binds antigen (e.g., lipoprotein or other component of the sample) with high affinity and high specificity. In this context "high affinity" refers to a dissociation constant of, for example without limitation, 1 µM, 100 nM, 10 nM, 1 nM, 100 pM, or even more affine, characterizing the binding reaction of antibody with antigen to which the antibody has been raised. The term "raised" refers to the production of high affinity antibody by methods long known in the art. Further in this context, the term "high specificity" refers to a preference of binding of a target antigen by a test antibody relative to non-target antigen characterized by a ratio of dissociation constants of, for example without limitation, 1, 2, 5, 10, 20, 50, 100, 200, 500, 1000, 10000, or more, in favor of binding of the target antigen to which the test antibody has been raised.

Methods of derivatization of antibodies and aptamers contemplated by the present invention include, for example without limitation, biotinylation. In some embodiments, the antibody or aptamer is biotinylated such that subsequent isolation on an avidin conjugated matrix, for example without limitation, an avidin chromatography column, affords facile separation by methods well known in the art of biochemical purification. In some embodiments, the biotinylated antibody or aptamer in complex with a lipoprotein is further subjected to streptavidin-conjugated magnetic beads. The ternary lipoprotein-biotinylated affinity reagent-streptavidin conjugated magnetic bead complex is then isolated by immunomagnetic methods well known in the art.

In some embodiments of this aspect, the lipoprotein-capture ligand is linked to a solid support by use of appropriate linkers well known in the art. The term "solid support" as used herein refers to a column, well, tube, gel, capsule, particle or the like. Exemplary solid supports include, without limitation, paramagnetic particles, microbeads, gel matrix material (e.g., agarose, Sephadex®), and the like.

Further to this aspect, in some embodiments the present invention provides methods for removing Lp(a) from the sample prior to centrifugation, which method includes the following steps: (a) forming a precipitate of Lp(a) by admixing the sample with a precipitant for Apo B-containing lipoproteins under conditions sufficient to cause precipitation of Lp(a); and (b) isolating the Lp(a) containing precipitate from the first solution. "Precipitant for Apo B-containing lipoproteins" and like terms refer to compounds known to precipitate Apo B, as well known in the art.

In some embodiments of the present invention contemplating purification of lipoproteins collected by centrifugation methods provided herein, the present invention provides methods for removing Lp(a) from collected lipoproteins, which methods include the following steps: (a) forming a precipitate of Lp(a) by admixing the collected lipoproteins with a precipitant for Apo B-containing lipoproteins under conditions sufficient to cause precipitation of Lp(a); and (b) isolating the Lp(a) containing precipitate from the collected lipoproteins.

Further to methods provided herein for removing Lp(a) from a solution containing lipoprotein, an exemplary precipitant for Apo B is, without limitation, DS in the presence of divalent cation. In some embodiments, the divalent cation is $Mg^{2+}$. It has been observed that inclusion of DS results in a significantly enhanced recovery of LDL with little effect on recovery of HDL. DS can be mixed with lipoprotein-containing sample at a concentration in the range of about 0.1 to 50 mg/mL. In some embodiments, the DS concentration is about 0.1, 0.2, 0.5, 1.0, 1.5, 2.0, 2.5, 3.0, 4.0, 5.0, 10.0, 15.0, 20.0, 25.0, 30.0, 40.0 or even 50.0 mg/mL.

In further embodiments, the invention provides methods for obtaining purified Lp(a), which methods include the following steps: (a) solubilizing the Lp(a) containing precipitate obtained according to any of the methods provided herein therefor; (b) admixing the solubilized Lp(a) with a solid-support reagent containing a lectin attached to a solid support under conditions suitable to allow formation of a Lp(a)-lectin complex; (c) isolating the Lp(a)-lectin complex; and (d) releasing the Lp(a) from the Lp(a)-lectin complex, thereby providing purified lipoproteins suitable for example for differential charged-particle mobility analysis.

Further to this method, the lectin may be selected from the group consisting of wheat germ agglutinin (WGA), lima bean agglutinin (LGA), phytohemaglutinin (PHA), and horseshoe crab lectin (HCL). In some embodiments, the lectin is WGA, In some embodiments, the solid support includes agarose. Methods of manipulation of such lectins, including reacting with Lp(a) to form a complex, isolating such a complex, and attaching lectin to a solid support, are well known in the art.

Further to this method, in some embodiments the releasing step includes washing the Lp(a)-lectin complex with a competitive ligand for the lectin. In some embodiments, the competitive ligand is N-acetylglucosamine (NAG). In some embodiments, the releasing step includes disulfide reduction, using a disulfide reducing agent as known in the art, to reduce the disulfide linking apo (a) and Apo B, thereby releasing LDL.

In some embodiments of the present invention contemplating further purification of lipoproteins collected by centrifugation methods provided herein, the present invention provides methods for removing Lp(a) from collected lipoproteins, which methods include the following steps: (a) solubilizing the Lp(a) containing precipitate obtained according to any of the methods provided herein therefor; (b) admixing the solubilized Lp(a) with gamma globulins and proline; (c) precipitating the admixture by addition of a precipitant; and (d) recovering Lp(a) from the precipitate, thereby providing purified lipoproteins suitable for differential charged-particle mobility analysis. As known in the art, "gamma globulin" refers to the γ-class of immunoglobulins. Exemplary precipitants include, without limitation, salts of highly charged inorganic ions, preferably ammonium sulfate. The concentration of gamma globulins useful for the present embodiment can be in the range of 0.01-0.1 µg/mL, 0.1-1.0 µg/mL, 1.0-2.0-µg/mL, 2.0-5.0 µg/mL, 5.0-10.0 µg/mL, 10.0-100 µg/mL, 100-1000 µg/mL, or even higher. The concentration of proline can be in the range of 10 µM-100 µM, 100-100-µM, 1-2 mM, 2-5 mM, 5-10 mM, or even higher.

Further to methods provided herein contemplating collected lipoprotein, in some embodiments the lipoprotein-containing solution is in contact with an inert centrifugation matrix. "Inert centrifugation matrix" and like terms in the context of centrifugal purification methods of the present invention refer to materials which do not chemically react with lipoproteins but which nonetheless enhance purification. Without wishing to be bound by any theory, it is believed that the inert centrifugation matrix acts to stabilize the contents of a centrifugation tube after centrifugation such that, for example, artifacts introduced during deceleration and/or pipetting of lipoprotein or other fraction from the tube are minimized. Exemplary inert centrifugation matrices include, without limitation, gel slurries or inert beads. In some embodiments, the gel slurry is a Sephadex® gel matrix. In some embodiments, the inert centrifugation matrix includes inert beads. Exemplary inert beads include, without limitation, glass beads, polystyrene beads, and the like, adapted to sink to the bottom of the first solution in a centrifuge tube. Inert beads can be of any convenient size, for example without limitation, about 0.1, 0.2, 0.5, 0.6, 0.7, 0.8, 0.9, 1.0, 1.1, 1.2, 1.3, 1.4, 1.5, 1.6, 1.7, 1.8, 2.0, 2.2, 2.4, 2.6, 2.8, 3.0, 3.3, 3.6, 3.9, 4.0 mm, or even smaller or larger.

In some embodiments of the aspect of the present invention directed to methods for purifying lipoproteins for differential charged-particle mobility analysis by the use of polyanionic compounds and one or more cations, the polyanionic compound is selected from the group consisting of dextran sulfate (DS), amylopectin and polyvinyl sulfate, preferably DS. In some embodiments, the cation is one or more divalent cations, such as $Mg^{2+}$ and $Ca^{2+}$. In some embodiments, the cation is preferably $Mg^{2+}$, $Ca^{2+}$, or both.

In some embodiments, the present invention provides methods for purifying lipoproteins for differential charged-particle mobility analysis, which methods do not include density gradient centrifugation. In some embodiments, a solution comprising lipoproteins and non-lipoproteins is admixed with one or more lipoprotein-capture ligands capable of binding lipoproteins to form a lipoprotein/lipoprotein-capture ligand complex. In some embodiments, after formation of a lipoprotein/lipoprotein-capture ligand complex, the complex so formed is isolated by methods known in the art including, without limitation, immunomagnetic methods. In some embodiments, after isolation of a lipoprotein/ lipoprotein-capture ligand complex, the lipoprotein is released from the lipoprotein/lipoprotein-capture ligand complex by methods known in the art and described herein.

In another aspect, the invention provides methods for analyzing the size distribution of lipoproteins by differential charged-particle mobility analysis. In some embodiments, one or more lipoproteins are obtained from a body fluid such as a plasma specimen from an individual. In some embodiments, the one or more lipoproteins are selected from the group consisting of HDL, LDL, Lp(a), IDL and VLDL. In some embodiments, the method further includes the step of using the determined lipoprotein size distribution to conduct an assessment of the individual, the assessment selected from the group consisting of lipid-related health risk, cardiovascular condition, risk of cardiovascular disease, and responsiveness to a therapeutic intervention.

"Assessment" in the context of lipid-related health risk, cardiovascular condition, and risk of cardiovascular disease, refers to a statistical correlation of the resulting lipoprotein size distribution with population mortality and risk factors, as well known in the art. Assessment in the context of responsiveness to a therapeutic intervention refers to comparison of the lipoprotein size distribution before and after a therapeutic intervention is conducted. Exemplary therapeutic interventions include, without limitation, the administration of drugs to an individual for the purpose of lowering serum cholesterol, lowering LDL, IDL, and VLDL, Lp(a) and/or raising HDL, as known in the art.

In some embodiments, the results of lipoprotein analyses are reported in an analysis report. "Analysis report", in the context of lipoprotein and other lipid analyses contemplated by the invention, refers to a report provided, for example to a clinician, other health care provider, epidemiologist, and the like, which report includes the results of analysis of a biological specimen, for example a plasma specimen, from an individual. Analysis reports can be presented in printed or electronic form, or in any form convenient for analysis, review and/or archiving of the data therein, as known in the art. An analysis report may include identifying information about the individual subject of the report, including without limitation name, address, gender, identification information (e.g., social security number, insurance numbers), and the like. An analysis report may include biochemical characterization of the lipids in the sample, for example without limitation triglycerides, total cholesterol, LDL cholesterol, and/or HDL cholesterol, and the like, as known in the art and/or described herein. An analysis report may further include characterization of lipoproteins, and references ranges therefore, conducted on samples prepared by the methods provided herein. The term "reference range" and like terms refer to concentrations of components of biological samples known in the art to reflect typical normal observed ranges in a population of individuals. Exemplary characterization of lipoproteins in an analysis report may include the concentrations of non-HDL lipoproteins and Lp(a) determined by differential charged-particle mobility. Further exemplary characterization of lipoproteins, determined for example by differential charged-particle mobility analyses conducted on samples prepared by methods of the invention, include the concentration and reference range for VLDL, IDL, Lp(a), LDL and HDL, and subclasses thereof. An analysis report may further include lipoprotein size distribution, obtaining for example by differential charged-particle mobility analysis, of a sample prepared by methods of the invention. Entries included in an exemplary analysis report are provided in Example 7.

The lipoproteins measured using ion mobility analysis according to embodiments of the present invention may be categorized based on diameter as listed in Table 2.

TABLE 2

Diameter Ranges for Lipoprotein Subfractions (in Angstroms)

| Subfraction | Diameter in Å |
| --- | --- |
| HDL small | 76.5-105.0 |
| HDL large | 105.0-145.0 |
| LDL very small | 180.0-208.2 |
| LDL small | 208.2-214.1 |
| LDL medium | 214.1-220.0 |
| LDL large | 220.0-233.3 |
| IDL small | 233.0-250.0 |
| IDL large | 250.0-296.0 |
| VLDL small | 296.0-335.0 |
| VLDL medium | 335.0-424.0 |
| VLDL large | 424.0-520.0. |

| Expanded LDL Regions | |
| --- | --- |
| Subfraction | Diameter in |
| LDL 4C (very small) | 180.0-190.0 |
| LDL 4B (very small) | 190.0-199.0 |
| LDL 4A (very small) | 199.0-204.9 |
| LDL 3B (very small) | 204.9-208.2 |
| LDL 3A (small) | 208.2-214.1 |
| LDL 2B (medium) | 214.1-220.0 |
| LDL 2A (large) | 220.0-224.6 |
| LDL 1 (large) | 224.6-233.3 |

Single-Stage Lipoprotein Separation with Dextran Sulfate and Microbeads

This invention also provides for methods of recovering high density and low density lipoproteins from a sample using a polyanionic compound and one or more cations to precipitate both HDL and LDL simultaneously, allowing the precipitate to associate with microbeads, removing the supernatant, then stripping the precipitated lipoproteins from the microbeads. The polyanionic compound used in these methods may be selected from the group consisting of dextran sulfate (DS), amylopectin and polyvinyl sulfate; preferably DS. In some embodiments, one or more cations are multivalent, such as divalent, such as $Mg^{2+}$ and $Ca^{2+}$. In some embodiments, the one or more cation is preferably $Mg^{2+}$, $Ca^{2+}$, or a combination of both. In some embodiments, the HDL and LDL recovered from the sample are then measured using ion mobility analysis. Preferably, the sample comprises plasma or serum.

In these methods where the sample comprises plasma, the sample may be treated with 10%-20% ethanol to remove fibrinogen prior to adding cations and dextran sulfate. In some embodiments the sample is treated with 16% ethanol to remove fibrinogen prior to adding cations and dextran sulfate.

As indicated above, dextran sulfate may be used to precipitate the lipoproteins. In one embodiment, the dextran sulfate is between 10 kD and 500 kD, such as between 20 kD and 100 kD, such as about 50 kD.

In some embodiments, the one or more cations comprise $Mg^{2+}$. The source of $Mg^{2+}$ may be any suitable magnesium salt, such as $MgCl_2$. In some embodiments, $Mg^{2+}$ is the only divalent cation. In these embodiments, $Mg^{2+}$ concentration may be in the range of about 25 mM to about 200 mM. More preferably, the $Mg^{2+}$ is in the concentration range of about 50 mM to about 150 mM; such as at the concentration of about 100 mM.

In some embodiments, the one or more cations comprise $Ca^{2+}$. The source of $Ca^{2+}$ may be any suitable calcium salt, such as $CaCl_2$. In some embodiments, $Ca^{2+}$ is the only divalent cation. In these embodiments, $Ca^{2+}$ concentration may be in the range of about 25 mM to about 200 mM. Preferably, the $Ca^{2+}$ is in the concentration range of about 50 mM to about 150 mM; such as at the concentration of about 150 mM.

In some embodiments, the one or more cations comprise two or more divalent cations, such as $Mg^{2+}$ and $Ca^{2+}$. In these embodiments, the total divalent cation concentration is within the concentration range of about 25 mM to about 200 mM. In some embodiments, the one or more divalent cations are $Mg^{2+}$ and $Ca^{2+}$. In these embodiments the $Mg^{2+}$ concentration is preferably about 100 mM and the $Ca^{2+}$ concentration is preferably about 25 mM.

In some embodiments, non-paramagnetic beads, such as non-paramagnetic microbeads, may be used to bind dextran sulfate-precipitated lipoproteins. In some embodiments, the non-paramagnetic beads are coated with streptavidin. In other embodiments, the non-paramagnetic beads are coated with a protein that binds specifically to dextran sulfate or lipoproteins, such as an antibody or other protein. Preferably, the non-paramagnetic beads have no specific binding agents attached to their outer layer. Preferably, the non-paramagnetic beads have an outer layer comprising carboxylate.

In some embodiments, magnetic beads (i.e., beads with a magnetic or paramagnetic core) may be used to bind dextran sulfate-precipitated lipoproteins. In some embodiments, the magnetic beads are coated with streptavidin. In other embodiments, the magnetic beads are coated with a protein that binds specifically to dextran sulfate or lipoproteins, such as an antibody or other protein. Preferably, the magnetic beads have no specific binding agents attached to their outer layer. Preferably, the magnetic beads have an outer layer comprising carboxylate or $NH_2$.

In embodiments using magnetic beads, the magnetic beads may be pelleted from a dispersed state in a container by using a magnet, such that the beads are attracted to the magnet and form a pellet where the magnet is closest to the container. Alternatively, the magnetic beads may be pelleted using centrifugation, such as low speed centrifugation. Similarly, in embodiments using non-paramagnetic beads, the non-paramagnetic beads can also be pelleted using centrifugation, such as low speed centrifugation.

Once pelleted, the supernatant may be poured off of the pelleted lipoprotein-precipitated magnetic beads, and the beads washed. The precipitated lipoproteins may then be released from the magnetic beads by using any suitable elution solution known in the art. In some embodiments, the precipitated lipoproteins are eluted from the beads at a pH within the range of about 7.4 and about 9.0. Preferably the precipitated lipoproteins are eluted from the beads at a pH of about 8.5 (within +/−0.1 pH units). In some embodiments, the elution buffer is ammonium acetate.

EXAMPLES

Example 1

Comparison of Lipoprotein Purification Using $D_2O$ and Low-Salt Solution

A serum sample (25 μL) was processed either using a low-density salt solution (1.151 g/mL) (i.e., "low-density salt sample") or $D_2O$ (200 μL each). Samples were centrifuged at 223,000×G for 3.7 hr (low-density salt sample) or 2 hr ($D_2O$). Following removal of the top 100 μL after centrifugation, the low-density salt sample was dialyzed against ammonium acetate solution and diluted to 1:200 before differential charged-particle mobility analysis. The $D_2O$ sample was diluted directly after centrifugation to 1:200 with ammonium acetate prior to differential charged-particle mobility analysis. Results of differential charged-particle mobility analysis are presented in FIG. 2.

Example 2

Effect of Purification on Apo A, Apo B, and TC Recovery

To assess whether HDL (Apo A1) was preferentially lost in procedures employing $D_2O$, three samples as shown in FIG. 3 (i.e., 749, 1043, 14: arbitrary and unique patient identification numbers) were subjected to lipoprotein isolation employing $D_2O$ together with RGD/DS solution (7.5/2.5 mg/mL, respectively) to remove albumin. Samples were each prepared in replicates of six. The isolated individual top 100 μL were each analyzed for content of Apo A1 (HDL), Apo B (LDL, IDL, VLDL) and total cholesterol (TC). Plasma or serum apolipoproteins AI and B were measured by standardized ELISA using commercially available monoclonal capture antibodies (Biodesign International, Saco, Minn.) and anti-human goat polyclonal detection antibodies, purified and biotinylated, (International Immunology Corp., Murrieta, Calif.) in a non-competitive sandwich-style immunoassay. Concentration was measured by addition of streptavidin conjugated peroxidase followed by color development using ortho-phenyline-diamine. Lipoprotein calibrators were standardized using CDC #1883 serum reference material (Center for Disease Control, Atlanta, Ga.) and pooled reference sera (Northwest Lipid Research Clinic, Seattle, Wash.). Total cholesterol was measured using commercially available assay kit reagents (Bayer Health Care, Tarrytown, N.Y.) according to manufacturers instructions and modified for analysis of 25 μl serum or plasma plus 200 μl cholesterol reagent per microtiter plate well. Standards, controls, samples and reagent background were measured after color development using a microtiter plate reader. The results (FIG. 3) show the mean recovery of each sample compared to the total present in each serum. Without wishing to be bound by any theory, the purification procedure did not result in preferential loss of HDL, as judged by equivalent recovery of Apo A1 and Apo B.

Example 3

Effect of Varying RGD on Lipoprotein Fraction Recovery

Figure 4:
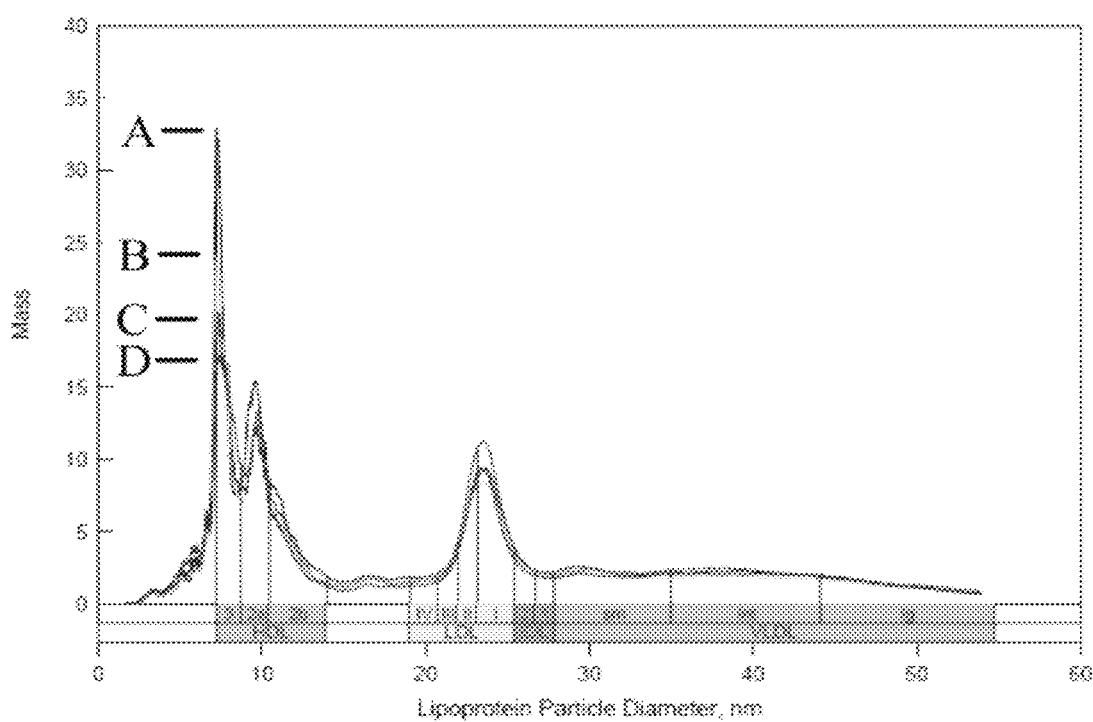
FIG. 4 shows the result of lipoprotein recovery from plasma after centrifugal purification using RGD. RGD was added to samples at various concentrations and centrifuged for 2 hr 15 min using $D_2O$ as the dense solution. Albumin Peak heights are indicated for the four different concentrations of RGD used; A, 10 mg/mL RGD; B, 15 mg/mL RGD; C, 20 mg/mL RGD; and D, 25 mg/mL RGD. The abscissa is lipoprotein diameter (nm), and the ordinate is an arbitrarily scaled mass coordinate, as discussed in the legend for FIG. 1.

A serum sample was mixed with varying amounts of RGD (10, 15, 20, 25 mg/mL) and incubated on ice for 15 min before being overlaid on a cushion of $D_2O$. After centrifuging for 120 min at 223,000×G, the top 100 μL was removed and diluted 1:200 with ammonium acetate solution. Samples were then analyzed by differential charged-particle mobility analysis. Results are shown in FIG. 4.

Example 4

Purification of Lipoproteins Employing RG 19, DS, AA

With reference to FIG. 5, in order to assess the effect of DS on the removal of albumin and recovery of lipoproteins in both the extraction/purification and diluent, a serum sample (5 μL) was extracted with 20 μL of 7.5 mg/mL RGD alone (legend "C/D" in FIG. 5) or 20 μL of a combination of 7.5 mg/mL RGD and 2.5 mg/mL DS (legend "A/B" in FIG. 5). The DS molecular weight used for both the extraction and diluent is 10K. After 15 min incubation on ice each sample was centrifuged for 2 hr 15 min at 223,000×G at 10 C. The top 100 μL was removed and diluted 1:200 with either 25 mM ammonium acetate solution (legend "B/D" in FIG. 5) or 25 mM ammonium acetate containing 5 μg/mL DS (legend "A/C" in FIG. 5).

Example 5

Result of Purification of Lipoproteins Employing DS in Diluent

With reference to FIG. 6, a lipoprotein-containing serum sample prepared by a 18 hr density separation, using methods well known in the art, was employed after dialysis to assess the effect of DS in the diluent on the recovery of LDL. An aliquot of the centrifuged serum sample was diluted 1:200 with 25 mM ammonium acetate in the absence of DS and subjected to differential charged-particle mobility analysis. Another aliquot was diluted 1:200 with 25 mM ammonium acetate in the presence of 5 μg/mL DS. Duplicate runs of each sample are shown in FIG. 6.

Example 6

Purification of Lipoproteins Employing RG 19, DS, $D_2O$

Lipoprotein-containing samples obtained from plasma were mixed briefly by vortexing. Five μL of sample, or optionally control, were mixed with 20 μL of an albumin removal reagent containing 7.5 mg/mL RGD (Sigma), 2.5 mg/mL DS (Sigma) and 0.5 mg/mL EDTA (Spectrum Chemicals) and incubated on ice for 15 min. Following incubation the sample mixture was overlaid on $D_2O$ (Medical Isotopes) 200 μL in a Ti 42.2 ultracentrifuge tube (Beckmann). The samples were then ultracentrifuged at 10° C. for 135 min at 223,000×G (42,000 rpm). Following ultracentrifugation the lipid fraction (85 μL) was removed from the top of the centrifuge tube. Prior to analysis by differential charged-particle mobility, the samples were diluted to a final dilution of 1:800 in 25 mM ammonium acetate 0.5 mM ammonium hydroxide pH 7.4 for HDL analysis. For LDL analysis samples were diluted 1:200 in the same diluent containing 5 μg/mL DS. Final dilutions were made in deep well 96 well plates and placed in an autosampler with the cool stack maintained at 6° C., prior to differential charged-particle mobility analysis.

Example 7

Result of Purification and Analysis of Lipoproteins in Serum Samples

Serum was separated from whole blood collected via venipuncture. Following separation the serum was divided into three portions, one aliquot analyzed for HDL, triglycerides, and total cholesterol content using traditional methods well known in the art. LDL was calculated from these results. In preferred embodiments, if triglycerides were greater than 400 mg/dL then LDL was measured directly. The second aliquot was analyzed for its Lp(a) content using an immunoassay, well known in the art. Differential charged-particle mobility analysis was employed for the third aliquot to fractionate the lipoproteins.

In a typical production procedure, sample(s) together with controls, one sample known to be LDL pattern A (control A) and one sample known to be pattern B (control B) as known in the art, are placed on the Perkin Elmer JANUS multiprobe. 30 μL of controls and sample(s) are transferred to a separate tube and mixed, and 120 μL of the RG19 dextran, DS, EDTA solution is added. The tubes are then transferred to ice for a 15-minute incubation. Following the 15 min incubation the tubes are returned to the multiprobe. In the meantime, centrifuge tubes have had two 4 mm beads added to them, and these are then placed on the multiprobe where 120 μL of $D_2O$ is added to each centrifuge tube. Controls and sample(s) are then overlaid on the $D_2O$ by the multiprobe before being transferred to the ultracentrifuge rotor (Ti 42.2). Samples are then spun for 135 min at 10 C at 223,000×G (42,000 rpm). Following centrifugation, the centrifuge tubes are removed carefully and placed on the multiprobe where the top 85 μL (+/−5 μL) is removed to a separate tube. Once all samples are collected the multiprobe makes two dilutions for each control and sample. One dilution is a final dilution of 1:200 with ammonium acetate solution containing 5 μg/mL DS; the second is a 1:800 dilution with just ammonium acetate solution. The two dilutions are then run on the differential charged-particle mobility instrument. Following analysis the particle numbers are converted to nmol/L using conversions well known in the art. The data from the HDL run (1:800) and the larger lipoproteins (1:200) are combined and reported together with the biochemical data from aliquots 1 and 2. The profile of the lipoproteins is also reported as well as the total LDL particle concentration and the LDL peak particle size, which is used to determine the LDL phenotype. An exemplary assessment report resulting from combining these data is provided in FIG. 7 (graphical representation of lipoprotein profile).

To obtain a more accurate lipoprotein profile using differential charged-particle mobility analysis as discussed above, one may adjust the results for any loss of lipoprotein during handling (e.g. sample centrifugation, pipetting and dilutions) prior to the differential charged-particle mobility apparatus. This may be achieved by adding one more types of labeled lipoproteins to a sample as an internal standard. By following the label during processing, the recovery of the labeled lipoprotein can be used to adjust upwards the concentration of the same but unlabeled lipoprotein present in the original sample. For example, an aliquot of the lipoprotein isolate after centrifugation is measured for fluorescent signal and compared with an aliquot directly from the starting stock sample (not centrifuged). The difference in signal represents the proportion of unknown sample recovered, and allows a more accurate calculation of lipoprotein concentration in plasma or serum.

The following method was used to conjugate a fluorescent molecule to HDL subfractions. This method may be applied to other types of lipoproteins. HDL was isolated from plasma by sequential flotation to obtain lipoproteins within density interval 1.063-1.20 g/mL. The total HDL fraction was then dialyzed to salt background density 1.184 g/mL and centrifuged for 28 hrs at 40,000 rpm, 10° C. in a fixed angle 50.3 Beckman rotor. The 6 ml centrifuge tube was then pipetted to obtain predominantly large, intermediate and small HDL subfractions, T[0-1], T[1-3] and T[3-6], respectively. The subfractions were then dialyzed against 100 mM $NaHCO_3$, pH 8.5, 4° C. overnight. Protein concentration was measured in each subfraction using the Lowry method.

HDL subfractions were then labeled with fluorescent probe AlexaFluor 488 (carboxylic acid, succinimidyl ester 'mixed isomers', Molecular Probes Cat #A-20000, Mol. Wt. 643.42, Abs @494 nm/Em 517 nm) according to manufacturer's instructions. Briefly, HDL subfractions were combined with AF488 at a suggested optimal ratio 10:1 (wt:wt) maintaining optimal concentrations of HDL and AF488, >2 mg/ml and 10 mg/ml, respectively. The protocol and quantities of the solutions used are listed below in Table 3.

TABLE 3

Incubation Mixtures

|  | Stk Co | Ligand | | Stk Co | AF488 | | Tot. Vol | Stop Soln |
|---|---|---|---|---|---|---|---|---|
|  | mg/ml | μl | mg | mg/ml | μl | mg | μl | μl |
| HDL Subfr. T [0-1] | 3.59 | 560 | 2.01 | 10 | 20.104 | 0.2010 | 580 | 40 |
| T[1-3] | 3.18 | 625 | 1.99 | 10 | 19.875 | 0.1988 | 645 | 40 |
| T[3-6] | 6.39 | 785 | 5.02 | 10 | 50.162 | 0.5016 | 835 | 100 |
|  |  |  |  | Total | 90.1405 | 0.901405 |  |  |

1—Add HDL subfr to glass vial with mag-stir bar
2—While stirring at rm. temp., add AF488 volume to ligand slowly.
3—Incubate mixture for 1 hour w/continuous stirring.
4—Add Stop Soln (1.5M Tris, pH 8.0). Incubate at rm temp 30 min.
5—Dialyze labeled HDL Subfrs to 20 mM Tris. 150 mM NaCl, 0.27 mM EDTA, pH 8 [in cold box, protect from light] vs. 1 liter overnite, and 2 × 1 L dialysate volume changes.

The AF488 labeled HDL subfractions were then tested for signal sensitivity at various dilutions in buffer from 250 to >30000. The labeled HDL subfractions were also tested for signal sensitivity when diluted in various plasma preparations before and after centrifugation for isolation of lipoproteins.

Additional dilution and sensitivity tests were performed after a second centrifugal isolation of the labeled HDL subfractions at density <1.23 g/mL to remove unconjugated fluorescent label from the HDL:AF488 conjugates.

The fluorescent probe fluorescein-5-EX, succinimidyl ester, obtained from Molecular Probes (Cat # F-6130), was used to label HDL subfractions in the same manner as described above for AF488. The above methods were also used to fluorescently label VLDL and LDL. Additional tests were conducted to fluorescence label combined high molecular weight standards (Pharmacia HMW Standard Mix) containing thyroglobulin, apoferritin, catalase, lactate dehydrogenase, and albumin.

Figure 7:
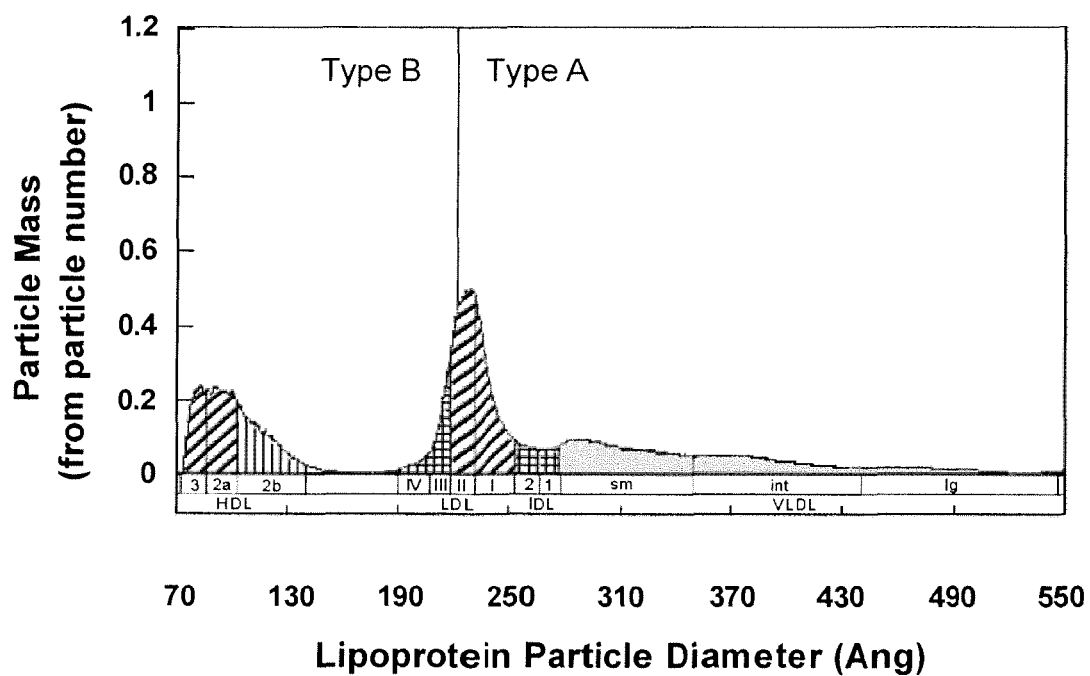
FIG. 7 shows the resulting lipoprotein profile in conjunction with a typical report on lipoprotein fractionation by differential charged-particle mobility analysis. The abscissa is lipoprotein diameter (nm), and the ordinate is a mass, calculated from differential charged-particle mobility data and parameters as known in the art. Areas shown with cross-hatching indicate relative risk, with the diagonal-lined sections representing medium risk, vertical-lined sections representing lower risk, cross-hatched sections representing higher risk, and the shaded sections representing indeterminate risk.

In embodiments of aspects of the present invention contemplating analysis and/or display of lipoprotein distributions, as exemplified without limitation by FIG. 1, FIG. 7 and the like, the differential charged-particle mobility data, obtained with an ion mobility analyzer, can be processed prior to presentation for clinical interpretation. Unless otherwise specified, "differential charged-particle mobility data" and like terms in the context of raw data from a differential charged-particle mobility analysis, or processed data for presentation for clinical interpretation, refer to differential charged-particle mobility particle size distributions having an independent variable correlated to the diameter of a particle, and an observed dependent variable correlated with particle count. In some embodiments, the independent variable is voltage or the corresponding electrical field generated by the voltage (see Eqn. 3). In some embodiments, the independent variable is particle diameter. In some embodiments, the dependent variable is particle count. In some embodiments, the dependent variable is the number of particles counted during a specified time period, for example without limitation 0.001-0.01, 0.01-0.1, 0.1-1, 1-2 s or even longer. In some embodiments, the specified time period is 0.1 s.

"Processing of the differential charged-particle mobility data" and like terms refer to manipulations of data, which manipulations, when taken in total, may provide graphical and/or numeric results which accurately and reproducibly reflect the lipoprotein distribution, and/or concentrations of individual lipoprotein classes and subclasses thereof, within a sample. Exemplary manipulations useful in the processing of differential charged-particle mobility particle size distribution data include, without limitation, multiplication by a constant, convolution with a function, addition and/or subtraction of a constant numeric value or a function including without limitation correction for the contribution of a contaminant, numeric integration, smoothing, and other arithmetic manipulations known in the art. Accordingly, processing of the differential charged-particle mobility particle size distribution data can be employed for a variety of reasons, including without limitation, correction to accurately reflect physiological concentrations of lipoproteins in a sample, scaling to correct for specific instrument and process efficiencies, removal of data representing contributions of a contaminant, and the like.

"Specific instrument and process efficiencies" and like terms refer to the detection and correction for changes in analyte (e.g., lipoprotein) concentration during processing and analysis. Exemplary specific instrument efficiencies include an apparent dilution introduced during electrospray wherein formation of the Taylor cone results in an apparent dilution of lipoprotein in the resulting particle-laden gas stream. Efficiencies are measured by methods employing instruments having quantified efficiencies well known to practitioners in the art.

"Contribution of a contaminant" and like terms in the context of differential charged-particle mobility particle size distribution data refer to data, for example without limitation particle count from an ion mobility instrument, resulting from non-lipoprotein species counted in the differential charged-particle mobility instrument and included in the differential charged-particle mobility particle size distribution data obtained therefrom. Exemplary non-lipoprotein species in this context include, without limitation, any reagent disclosed herein and albumin in monomeric and/or multimeric form.

In some embodiments, the contribution to the differential charged-particle mobility particle size distribution data due to a reagent described herein is subtracted from the differential charged-particle mobility size distribution data during processing of the data. For example, without wishing to be bound by any theory, it is believed that a contribution due to RGD in particle size distribution data from a differential charged-particle mobility analysis (i.e., differential charged-particle mobility particle size distribution data having particle count versus particle diameter) can be represented by a one or more decaying exponential functions over selected diameter regions. Accordingly, in some embodiments the differential charged-particle mobility particle size distribution data are fit in a selected region to a function having the form of Eqn 4:

$$y_1 = k_1 * e^{(-0.7*d)} \quad (4)$$

wherein $y_1$ is the best fit for the contribution to the differential charged-particle mobility as determined by methods well known in the art, $k_1$ is an empirical constant of the fit, and d is the particle diameter. The above Eqn. 4 is valid for particle diameters of greater than 2 nm. In some embodiments, the region of the fit is 3-6, 3-4, 3-5, 3-6, 4-6, or 5-6 nm (particle diameter), preferably 3-4 nm. In some embodiments, the entire set of differential charged-particle mobility data is corrected by the function resulting from a fit to Eqn. 4.

In some embodiments, the differential charged-particle mobility particle size distribution data are further processed to account for a contribution due to albumin inclusion in the sample taken for differential charged-particle mobility analysis. In some embodiments, the construction of a correction for albumin (i.e., "albumin correction curve") is initially afforded by a piecewise function having the following form:

| Region | Dependent variable region, nm | Functional correction |
|---|---|---|
| 1 | 0 <= d < 7 | 0 |
| 2 | 7 <= d < 7.1 | $y_2 = k_2 * e^{(-2.56 * 7.1)}$ Eqn. (5) |
| 3 | 7.1 <= d < 8.5 | $y_3 = k_3 * e^{(-2.56 * d)}$ Eqn. (6) |
| 4 | 8.5 <= d < 15 | Empirical (from spiked albumin data) | wherein $y_2$ and $y_3$ are the functional values in regions 2 and 3, respectively, $k_2$ and $k_3$ are empirical constants determined by methods well known in the art, and d is the particle diameter. "Empirical (from spiked albumin data)" refers to the effect on differential charged-particle mobility particle size distribution data of subtracting from the distribution an amount of albumin equivalent to the amount of albumin in the measured distribution.

In some embodiments, the albumin correction curve is further modified to account for the presence of albumin dimer. It has been found empirically that albumin dimer is typically present in samples for differential charged-particle mobility analysis in the range of 1-10%, 1-8%, 2-8%, 2-7%, 2-6%, 2-5%, preferably 2%, and that an albumin correction curve can be scaled in a particular region to account for, and to gradually suppress, the presence of albumin dimer. In some embodiments, the lower diameter limit of this particular region is 0, 1, 2, 3, 4, 5, 6, 7, 8, 9, 10, 11 or even 12 nm. In some embodiments, the upper diameter limit of this particular region is 1, 2, 3, 4, 5, 6, 7, 8, 9, 10, 11, 12, 13, 14 or even 15 nm. In some embodiments, the range of this particular region is 0-15, 5-10, 7-9, preferably 7.9-8.4 nm. Accordingly, the albumin correction curve can be modified by a function having the form of Eqn 7:

$$y' = y * ((d - \text{lowerlimit}) * 2 * \text{dimer} + (\text{upperlimit} - d) * 2) \quad (7)$$

wherein y is the albumin correction curve, y' is the albumin correction curve after gradual suppression of the presence of albumin dimer, d is the particle diameter, lowerlimit and upperlimit are the lower and upper size limits for the correction, respectively, and dimer is the selected percentage dimer concentration. In some embodiments, the region in which the presence of dimer is suppressed is between 7.9 nm (lowerlimit) and 8.4 nm (upperlimit).

In some embodiments, a theoretical curve representing albumin monomer is fit to the differential charged-particle mobility particle size distribution of a sample in a particular region, using curvefitting methods well known in the art. In some embodiments, this theoretical curve is represented by a function having the form of Eqn. 8:

$$y_m = k_m * e^{(-k_a * d)} \quad (8)$$

wherein $y_m$ is the theoretical number distribution of albumin monomer, $k_m$ and $k_a$ are empirically derived constants In some embodiments, $k_a$ is in the range of 0.1-10, 1-5, 2-4 or 2-3. In some embodiments, $k_a$ is 2.56. In some embodiments, this particular region is the range 0-15, 5-10, 6-9, 7-8, preferably 7.3-7.5 nm. In some embodiments, after determination of the contribution of albumin monomer which results in the best fit to Eqn. 8, the differential charged-particle mobility particle size distribution data are corrected by subtracting Eqn. 7 therefrom, scaled by the same contribution. In some embodiments, the correction afforded by subtracting Eqn. 7 is conducted in a particular region, for example without limitation, 0-15, 2-12, 4-10, preferably 6-10 nm. In some embodiments wherein the correction does not contemplate the range 10-11 nm, a corresponding correction in the region 10-11 nm is conducted by multiplying Eqn 7. by a factor of (11-diameter) and subtracting the result from the differential charged-particle mobility particle size distribution data.

The process described above may be implemented in a variety of electronic devices, such as desktop or laptop computers or handheld devices, for example. Such devices are well known to those skilled in the art. Additionally, the results may be displayed on a monitor, printed or stored on a memory device, such as a hard drive, CD ROM, CD R/W, flash memory or the like. Further, the results may be made available to other devices through a network, which may be a private network or a public network, such as the Internet. In this regard, the electronic device and/or the memory device may be accessible through the network.

In one embodiment, the measured values are compared to empirically determined ranges to perform a diagnosis based on a patient's serum or plasma values falling within or outside a range. The chart below illustrates one exemplary set of ranges for such a diagnosis:

| nmol/L | HDL 3 | HDL 2a | HDL 2b |
|---|---|---|---|
| Female | 475-4224 | 903-3779 | 384-1616 |
| Male | 613-3344 | 1174-3744 | 169-1153 |

| nmol/L | LDL IV | LDL III | LDL II | LDL I |
|---|---|---|---|---|
| Female | 33-129 | 82-442 | 91-574 | 51-186 |
| Male | 38-164 | 136-627 | 200-596 | 48-164 |

| LDL Total |
|---|
| 272-1189 |
| 508-1279 |

| LDL Particle Size (A) |
|---|
| Female 215.4-232.9 |
| Male 212.3-230.9 |

| nmol/L | IDL 2 | IDL 1 |
|---|---|---|
| Female | 11-48 | 10-38 |
| Male | 12-59 | 11-41 |

| nmol/L | VLDL sm | VLDL int | VLDL lg |
|---|---|---|---|
| Female | 5.8-26.6 | 1.0-5.7 | 0.2-1.8 |
| Male | 5.0-23.0 | 1.1-7.3 | 0.2-2.5 |

Differential charged-particle mobility spectrometry provides a way to measure the size distribution of nanoparticles based on gas-phase particle electrical mobility. This methodology was adapted for measuring the size distribution of lipoprotein particles. The method was automated and generated profiles of particle number and particle mass versus particle diameter in about two minutes. Lipoproteins are first enriched (plasma protein removal) by ultracentrifugation and then diluted in a volatile buffer and electrosprayed. A charge neutralization process leaves a well-characterized fraction of the particles with a single charge. The charged particles are drawn through a Differential Mobility Analyzer (DMA), which allows particles of a narrow size to pass to a particle counter as a function of a voltage applied to the DMA. By scanning the applied voltage, particle number distributions are obtained for HDL, LDL, IDL and VLDL. The measurements are based on first principles and do not need to be calibrated with respect to particle size. Particle number distributions are converted into particle mass distributions. Using this method, the intra-assay variation for LDL diameter was <0.6%, for concentration, <10% for HDL and LDL and <15% for IDL and VLDL. The inter-assay reproducibility was <1.0% for LDL particle size, and for concentration, <15% for HDL and LDL and <20% for IDL and <25% for VLDL. Table 4 below shows the summary data, expressed as mean and SD, used to generate reference ranges for the individual lipoprotein fractions. A total of 259 healthy individuals (191 F, 68 M) who met the current NCEP ATP III criteria for optimal lipid/lipoprotein levels: total cholesterol (chol)<200, LDL chol<100, HDL chol>40 (M)>50 (F), triglyceride<150 mg/dL were used in the study. The results show the expected difference between genders, males having higher concentrations of smaller LDL particles and females having increased HDL 2b.

TABLE 4

Summary Data of 259 Individuals

| Lipoprotein Fraction | Gender | Mean nmol/L | SD nmol/L | P males vs. females |
|---|---|---|---|---|
| HDL 3 | Female | 1443 | 847 | 0.071 |
|  | Male | 1646 | 602 |  |
| HDL 2b | Female | 834 | 299 | <0.003 |
|  | Male | 494 | 258 |  |
| HDL 2a | Female | 2343 | 719 | 0.850 |
|  | Male | 2325 | 655 |  |
| LDL IV | Female | 70 | 24 | <0.003 |
|  | Male | 84 | 31 |  |
| LDL III | Female | 212 | 103 | <0.003 |
|  | Male | 313 | 125 |  |
| LDL II | Female | 336 | 125 | <0.003 |
|  | Male | 407 | 119 |  |
| LDL I | Female | 112 | 35 | 0.012 |
|  | Male | 100 | 29 |  |
| Total LDL | Female | 727 | 227 | <0.003 |
|  | Male | 893 | 193 |  |
|  |  | Angstrom | Angstrom |  |
| LDL Peak Diameter | Female | 225.7 | 4.48 | <0.003 |
|  | Male | 221.7 | 4.19 |  |
| IDL 1 | Female | 16 | 9 | 0.003 |
|  | Male | 20 | 11 |  |
| IDL 2 | Female | 25 | 10 | 0.007 |
|  | Male | 29 | 12 |  |
| VLDL small | Female | 11.2 | 5.7 | 0.506 |
|  | Male | 10.7 | 4.8 |  |
| VLDL inter | Female | 3.0 | 1.3 | <0.003 |
|  | Male | 3.7 | 1.6 |  |
| VLDL large | Female | 0.9 | 0.4 | <0.003 |
|  | Male | 1.2 | 0.6 |  |

Ranges for the remainder of the population (abnormal) with one or more criterion outside the ATP III guidelines were determined. These showed expected differences with increased concentrations of smaller LDL as well as decreased size and decreased concentration of HDL 2b (B) with little change in HDL 2a and 3.

The methods described above may be carried out in a variety of apparatuses. For example, U.S. Pat. No. 7,259,018 to Benner et al. describes an apparatus by which a sample solution in a centrifuging tube is expelled through a capillary tube where it becomes ionized by the electrospray process as it exits the capillary tube. Thus, the pressure differential caused by the pressure chamber transfers the ionized sample into a gas stream, which then carries the sample to a mobility analyzer. Once the sample in the centrifuging tube is analyzed, another tube of sample is placed within the pressure chamber. In this arrangement, however, since only a small volume of the sample is provided at any time in a centrifuging tube, the flow rate of the sample through the capillary can vary substantially over time even if the pressure in the pressure chamber is maintained, thereby affecting the quantitative determinations from the ion mobility analyzer based on predicted flow rates.

Figure 8:
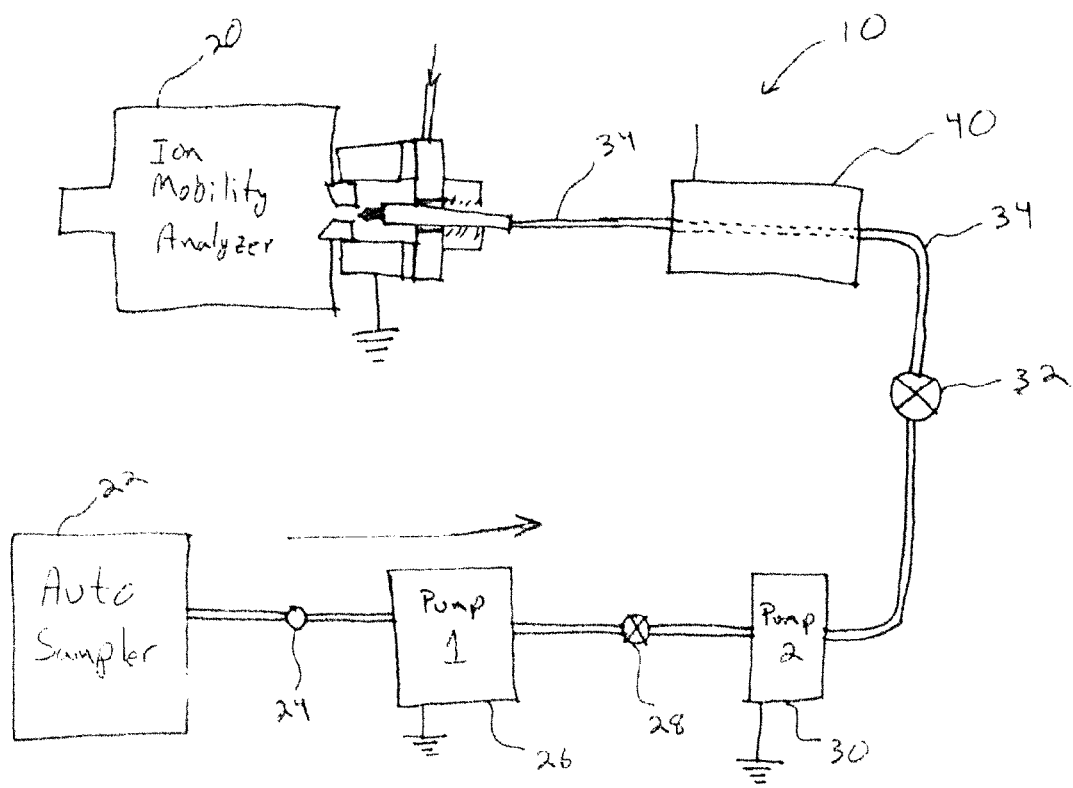
FIG. 8 illustrates an apparatus for differential charged-particle mobility analysis according to an embodiment of the present invention.

Embodiments of the present invention address these concerns. In accordance with embodiments of the invention, a constant flow rate is achieved by pumping the sample through a capillary and by ionizing (or charging) the sample within the capillary during flow to the ion mobility analyzer. FIG. 8 illustrates an exemplary apparatus for ion mobility analysis according to an embodiment of the invention. The ion mobility analysis apparatus 10 of FIG. 8 includes an ion mobility analyzer 20 similar to that illustrated in U.S. Pat. No. 7,259, 018. The ion mobility analyzer 20 is capable of counting particles flowing therethrough. The ion mobility analyzer 20 may be provided with an electronic device (not shown), such as a computer, capable of processing the data in accordance with, for example, the algorithm described above.

A charged particle stream of the sample is provided to the ion mobility analyzer 20 from an autosampler 22. The autosampler 22 may be a robotic system for automatically supplying a sample. One such autosampler is model HTC PAL, Leap Technologies of Carrboro, N.C. In one embodiment, the autosampler is a robotic device that only supplies purified sample from a rack of tubes or from a multiwell plate to the pump(s). The autosampler 22 can provide a substantially continuous supply of samples for ion mobility analysis without the need for substantial human intervention.

Sample from the autosampler 22 is supplied to a first pump 26 through an injection port 24. In this regard, the autosampler 22 may include a reservoir (not shown) in which the purified sample is contained. The injection port 24 may be a part of the first pump 26. The first pump 26 is a high flow-rate (or high-flow) pump capable of pumping the sample from the autosampler 22 at a relatively high flow rate (e.g., greater than or equal to 1.0 microliter per minute). In one embodiment, the high-flow pump pumps the sample from the autosampler 22 at a rate of approximately 5-20 microliters per minute. Most preferably, the high-flow pump pumps the sample at a rate of approximately 10 microliters per minute. Suitable high flow pumps are obtained from Eksigent Technologies, 2021 Las Positas Ct Suite 161, Livermore, Calif.

From the first pump 26, the sample is supplied to a second pump 30. The second pump 30 is a low flow-rate (or nanoflow) pump capable of pumping the sample to a capillary 34 at a relatively low rate (e.g., less than or equal to 1.0 microliters per minute) to enable proper ionization or charging of the particles of the sample, as described below. In one embodiment, the nanoflow pump pumps the sample to the capillary at a rate of approximately 100-200 nanoliters per minute. Most preferably, the nanoflow pump pumps the sample at a rate of approximately 200 nanoliters per minute. Suitable nanoflow pumps are obtained from Eksigent Technologies, 2021 Las Positas Ct Suite 161, Livermore, Calif.

In one embodiment, a combination pump assembly may be used in place of the two pumps. For example, a pump assembly may include a high-flow component and one or more nanoflow components. An exemplary combination pump assembly is NanoLC 1-D, available from Eksigent Technologies, 2021 Las Positas Ct Suite 161, Livermore, Calif.

In one embodiment, the first pump 26 may supply the sample to a plurality of nanoflow pumps through either a single valve 28 or a plurality of valves.

Flow to and through the capillary 34 may be controlled via a valve 32, which may be part of the second pump 30 or may be a separate valve positioned within the capillary 34. The valve 32 ensures a constant flow rate of the sample through the capillary 34 downstream of the valve 32. The valve 32 may be electronically controlled to maintain the constant flow rate. In this regard, the valve may be controlled in response to sensors or meters positioned downstream of the valve 32.

The sample particles are charged during their flow through the capillary 34 by an ionizer 40. As will be understood by those skilled in the art, the actual ionization or charging of the particles may occur as the particles exit the capillary into the ion mobility analyzer. In one embodiment, the ionizer 40 is a conductive union assembly positioned around a portion of the capillary 34. Conductive unions (also known as a conductive junctions) apply an electrical current around a very thin flow to provide an electrical charge to the flow. One exemplary conductive union assembly is described in U.S. Pat. No. 7,075,066, which is incorporated herein by reference in its entirety. The charged sample particles are then supplied through the capillary 34 to the ion mobility analyzer 20.

Figure 9A:
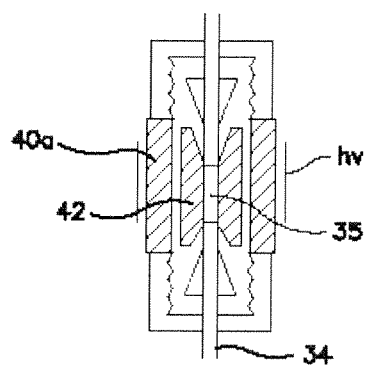
FIGS. 9A and 9B illustrate embodiments of conjunctive unions for use with the apparatus of FIG. 8.
Figure 9B:
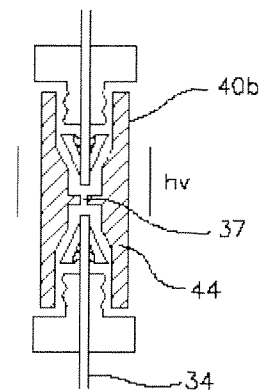

FIGS. 9A and 9B illustrate exemplary embodiments of the conductive union for use in charging the flow of the sample particles through the capillary. Referring first to FIG. 9A, a conductive union assembly 40a is formed around the capillary 34. An ionization region 35 of the capillary 34 is surrounded by a conductive union 42. A voltage applied to the conductive union 42 causes charging of the particles in the flow through the ionization region 35 of the capillary 34. For a detailed explanation of the operation of the conductive union assembly 40a, reference may be made to U.S. Pat. No. 7,075,066.

Referring now to FIG. 9B, another embodiment of a conductive union assembly is illustrated. In the embodiment of FIG. 9B, a conductive union assembly 40b forms a microtite region 37 in a portion of the capillary 34 through which the sample flows. The microtite region 37 may form a joint, or a seal, between two sections of the capillary. The microtite region 37 has a small dead volume in which the sample particles are charged. In one embodiment, the microtite region 37 has a dead volume of approximately 5-50 nanoliters. In a most preferred embodiment, the microtite region 37 has a dead volume of approximately 10-15 nanoliters. The microtite region 37 is preferably formed of stainless steel. The conductive union assembly 40b includes a conductive union 44 formed around the microtite region 37. A voltage applied to the conductive union 44 causes charging of the particles in the flow through the microtite region 37.

Thus, the ion mobility analyzer 20 is provided with a controlled nanoflow of the sample at a substantially time-invariant rate. In this regard, the flow rate preferably varies by less than five percent from a nominal rate, more preferably by less than two percent and, most preferably by less than one percent. This allows for a more consistent and reliable analysis to be performed by the ion mobility analyzer 20.

Example 8

Lipoprotein Separation: Dextran Sulfate Precipitation with Low Speed Centrifugation (DS-LSC)

Serum samples were treated with dextran sulfate (DS) (50 kD) in solution with $Mg^{2+}$ and incubated for about 3 minutes to precipitate LDL. The incubated samples were then centrifuged for about 30 minutes to pellet the precipitated LDL. The supernatant (containing HDL) was removed and set aside. The pelleted LDL was then dissolved in 25 mM ammonium acetate (pH≈9), diluted 1:200 in an ammonium acetate/dextran sulfate solution and analyzed using differential ion-mobility analysis as described in Example 7.

The HDL-containing supernatant was treated with additional dextran sulfate and $Mg^{2+}$, incubated for about 3 minutes, and then centrifuged for about 30 minutes to pellet the HDL. The supernatant was removed, and the pelleted HDL was dissolved in 25 mM ammonium acetate (pH≈9). The solubilized HDL was then treated in a desalting. The desalted HDL solution was collected and diluted 1:800 in 25 mM ammonium acetate (pH≈9) and analyzed using differential ion-mobility analysis as described in Example 7.

Figure 10:
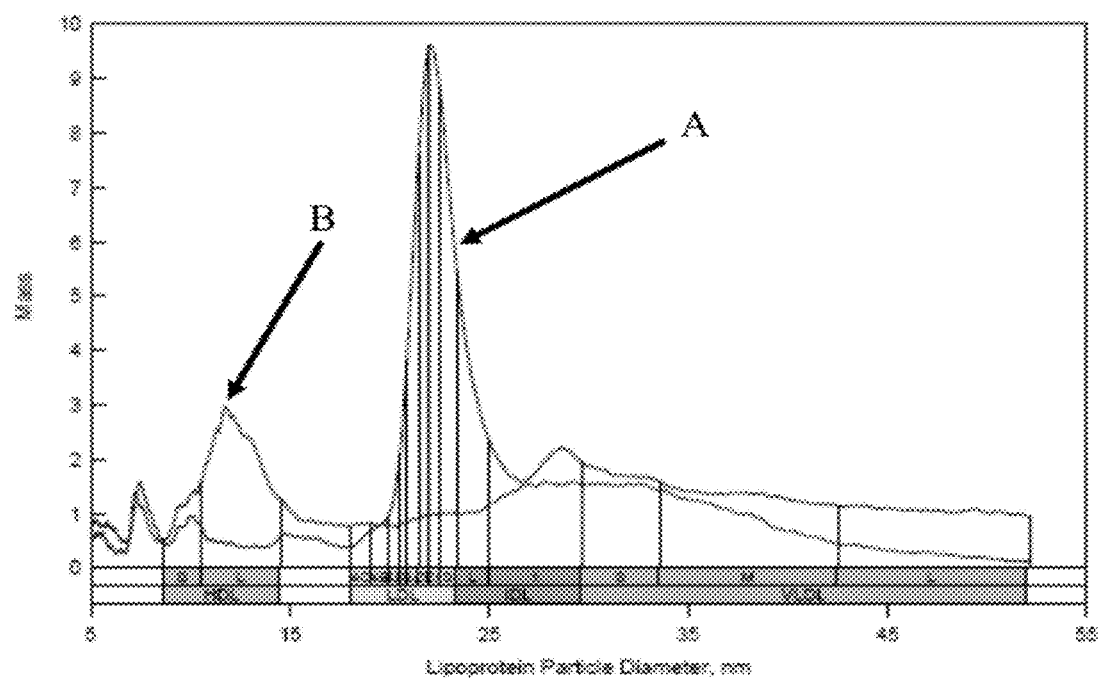
FIG. 10 shows ion mobility profiles of lipoprotein separation from serum using dextran sulfate and low speed centrifugation. HDL and LDL were precipitated in separate steps and the resulting ion mobility profiles for each were superimposed. Details are described in Example 8

FIG. 10 shows ion mobility traces obtained by differential ion mobility analysis for the LDL and HDL fractions collected above. The HDL and LDL traces are from separate runs and are overlayed on the same plot. Trace A represents the HDL fraction and Trace B represents the LDL fraction.

Example 9

Comparison of Lipoprotein Separations: Two-Stage Lipoprotein Separation with Biotinylated Dextran Sulfate (b-DS) and Streptavidin-Coated Magnetic Beads (s-MB) vs. DS-LSC Lipoprotein separation using the method of Example 8 (DS-LSC) was compared with a similar method modified with biotinylated dextran sulfate and streptavidin coated magnetic beads (b-DS/s-MB). Two serum samples were split into two aliquots apiece. One aliquot from each sample was processed using the DS-LSC lipoprotein separation method of Example 8. The remaining two aliquots were processed using the b-DS/s-MB lipoprotein separation method described below.

Dextran sulfate (50 kD) was aminated, then biotinylated on the amine group. Serum samples were diluted 1:10 in 25 mM ammonium acetate (pH≈9). The biotinylated dextran sulfate (b-DS) in solution with $Mg^{2+}$ was added to the diluted samples and incubated for about 3 minutes to precipitate LDL. Streptavidin-coated magnetic beads (s-MB) were then added to the b-DS-treated sample and incubated for about 4 minutes to bind the precipitated LDL. A magnet was then applied to the samples to pellet the magnetic beads, and the HDL-containing supernatant was removed and set aside. The pelleted magnetic beads were then washed with 25 mM ammonium acetate (pH≈9) for about 4 minutes to solubilize and remove the LDL from the b-DS. The magnetic beads were then re-pelleted using a magnet, and the LDL-containing supernatant was removed and diluted 1:1200. The LDL containing solution was then analyzed using differential ion-mobility analysis as described in Example 7.

The HDL-containing supernatant previously set aside was re-treated with b-DS in solution with $Mg^{2+}$ and streptavidin magnetic beads to isolate the HDL as described above. The magnetic beads were then re-pelleted using a magnet, and the HDL-containing supernatant was removed and diluted 1:800. The HDL containing solution was then analyzed using differential ion-mobility analysis as described in Example 7.

FIGS. 11A and 11B show ion mobility traces obtained by differential ion-mobility analysis of LDL-containing supernatant from two samples using the biotinylated dextran sulfate and streptavidin-coated magnetic beads (b-DS/s-MB). Traces A and B of FIG. 11A show LDL isolated from two samples using the b-DS/s-MB method. The b-DS/s-MB method consistently isolated LDL from serum samples.

FIG. 11B shows four ion mobility traces of HDL-containing supernatant: traces A and B show HDL isolated using the b-DS/s-MB method of this example; traces C and D show HDL isolated using the DS-LSC method set forth in Example 8. As seen in FIG. 11B, the b-DS/s-MB method isolated more than twice as much HDL as the DS-LSC method.

Example 10

Single-Stage Lipoprotein Separation with Biotinylated Dextran Sulfate and Streptavidin-Coated Magnetic Beads Serum samples were added to a solution of biotinylated 50 kD dextran sulfate (b-DS, prepared as described in Example 9) and $Mg^{2+}$ and incubated for about 3 minutes. Streptavidin-coated magnetic beads (s-MB) were then added to the b-DS-treated sample and incubated for about 4 minutes to collect the precipitated lipoproteins. A magnet was then applied to the sample to pellet the magnetic beads, and the supernatant was removed and set aside. The pelleted magnetic beads were then washed with 25 mM ammonium acetate (pH≈9) for 4 minutes to solubilize and remove both the HDL and LDL from the b-DS. The magnetic beads were then re-pelleted using a magnet, and the lipoprotein-containing supernatant was removed and diluted 1:800. The diluted supernatant was then analyzed using differential ion-mobility analysis as described in Example 7.

Figure 12:
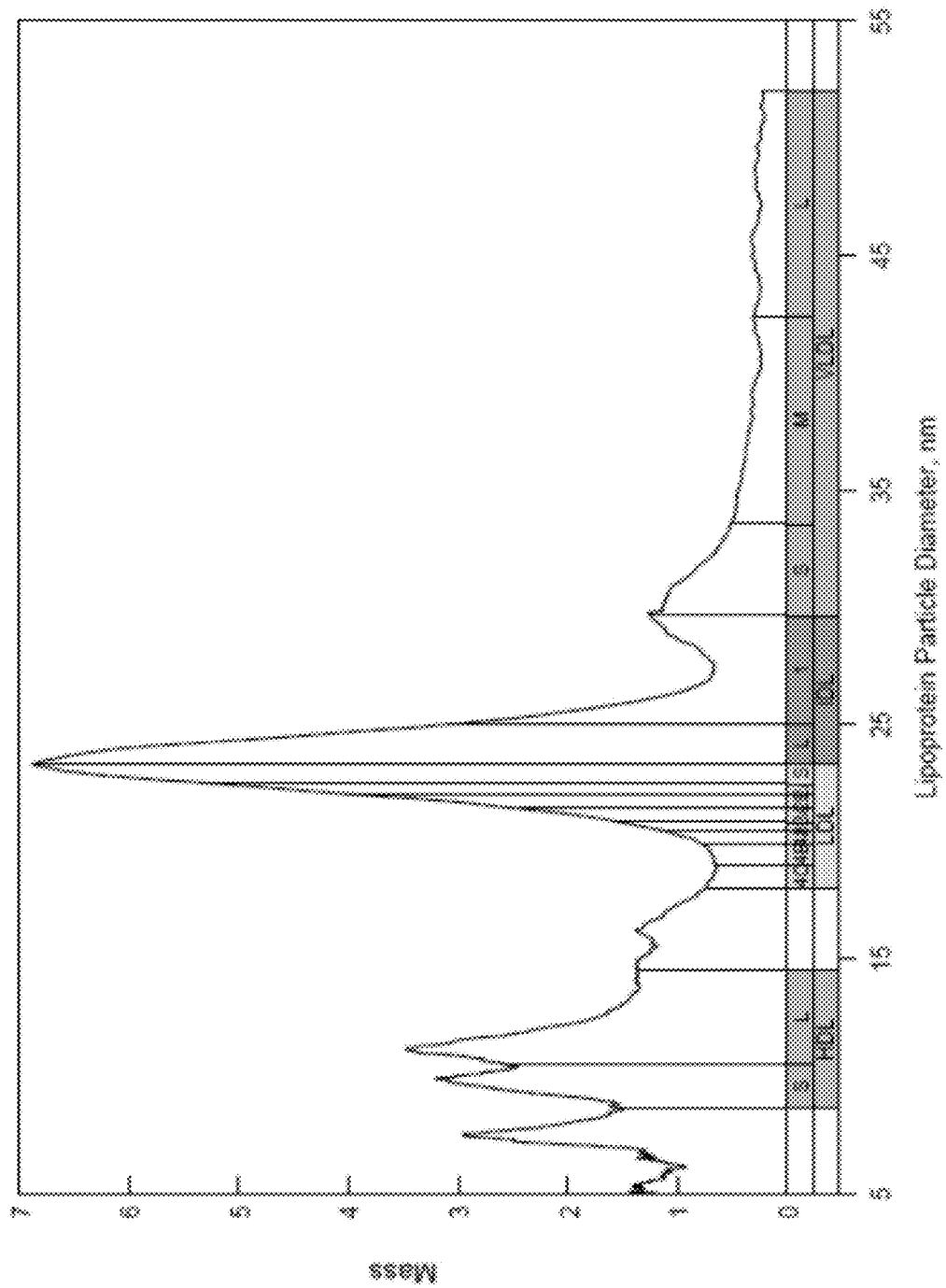
FIG. 12 shows an ion mobility profile of HDL and LDL simultaneously recovered from a serum sample using biotinylated dextran sulfate and streptavidin-coated magnetic beads. Details are described in Example 10.

As seen in FIG. 12, both HDL and LDL can be separated from a single serum sample using the single-stage separation detailed above.

Example 11

Comparison of Lipoprotein Separations: b-DS/s-MB vs. Ultracentrifugation

In order to compare the effectiveness of ultracentrifugation-based lipoprotein separation and b-DS/s-MB lipoprotein separation, two serum samples were treated using either the methods of Example 1 or Example 10, and then analyzed using differential ion-mobility analysis as described in Example 7.

Figure 13:
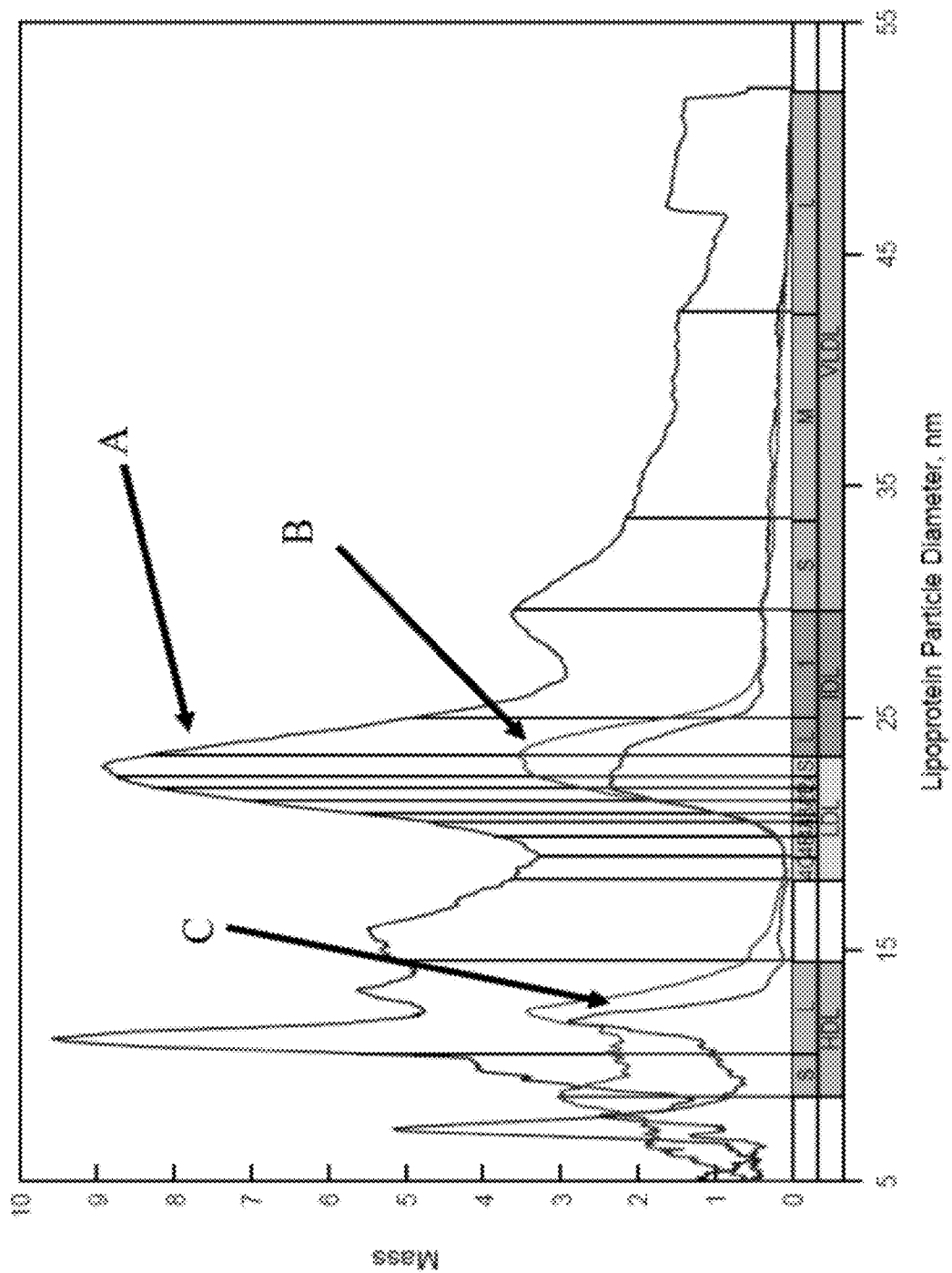
FIG. 13 shows ion mobility profiles of lipoprotein recovered from serum using two different methods: 1) recovery with biotinylated dextran sulfate and streptavidin-coated magnetic beads; or 2) ultracentrifugation. Details are described in Example 11.

Lipoprotein separation using b-DS/s-MB resulted in a more than four-fold increase in the yield of LDL and about a two-fold increase in the yield of HDL compared with ultracentrifugation. FIG. 13 shows the ion mobility traces of samples processed by the two methods. Trace A is from the sample treated using b-DS lipoprotein separation, trace B is from LDL recovered using ultracentrifugation, and trace C is from HDL recovered using ultracentrifugation.

Example 12

Comparison of Lipoprotein Separation: Unconjugated DS/MB vs. b-DS/s-MB

To determine whether the specificity of the biotin-streptavidin system was required for the dextran sulfate-magnetic bead system to work, serum samples were processed using the procedure set forth in Example 10, either using biotinylated dextran sulfate (b-DS) and streptavidin-coated magnetic beads (s-MB) or unconjugated dextran sulfate and magnetic beads (DS/MB). The processed samples were then analyzed using differential ion-mobility analysis as described in Example 7.

Figure 14:
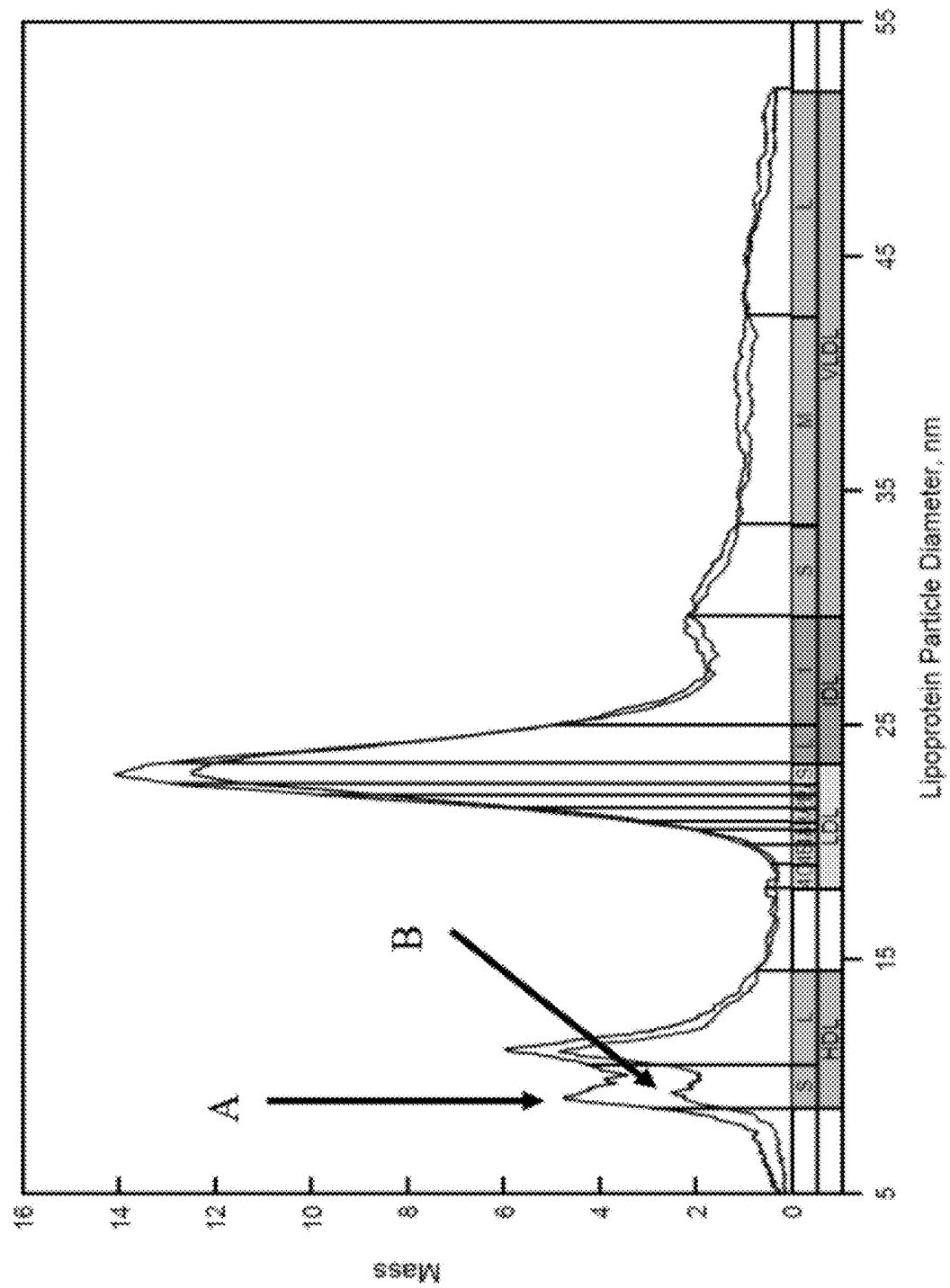
FIG. 14 shows ion mobility profiles of lipoprotein recovered from serum, using either 1) unconjugated dextran sulfate and magnetic beads, or 2) biotinylated dextran sulfate and streptavidin-coated magnetic beads. Details are described in Example 12.

As seen in FIG. 14, the amount of LDL recovered from serum was approximately the same, regardless of whether the dextran sulfate and beads were conjugated to biotin and streptavidin, respectively. Trace A shows lipoprotein recovered using b-DS/s-MB, trace B shows lipoprotein recovered using unconjugated DS/MB.

The amounts of HDL-L were also approximately the same, and the amounts of HDL-S recovered using unconjugated dextran sulfate and magnetic were about half that of the dextran sulfate and magnetic beads conjugated to biotin and streptavidin.

Example 13

Effect of Dextran Size on Lipoprotein Separation Using Dextran Sulfate and Magnetic Beads In order to determine what effect, if any, the size of dextran sulfate has on lipoprotein recovery, multiple aliquots of a serum sample were processed using the procedure as set forth in Example 10, but substituting unconjugated dextran sulfates (DS) (ranging from 10 to 500 kD) and unconjugated magnetic beads (MB) for the biotinylated dextran sulfate and streptavidin-coated magnetic beads. Individual aliquots were processed with dextran sulfates at 10, 20, 50, 100, and 500 kD (dextran sulfates at 10, 20, 50, and 100 kD were run in duplicate). Samples were then analyzed using differential ion-mobility analysis as described in Example 7. The results of these analyses are shown in FIGS. 15A and 15B.

As seen in FIG. 15A, processes using 10 and 20 kD dextran sulfate failed to recover HDL-S. Trace A of FIG. 15A is from analysis of the control 50 kD dextran sulfate, traces B and C are from the 10 kD dextran sulfate samples, and traces D and E are from the 20 kD dextran sulfate samples.

Figure 15B:
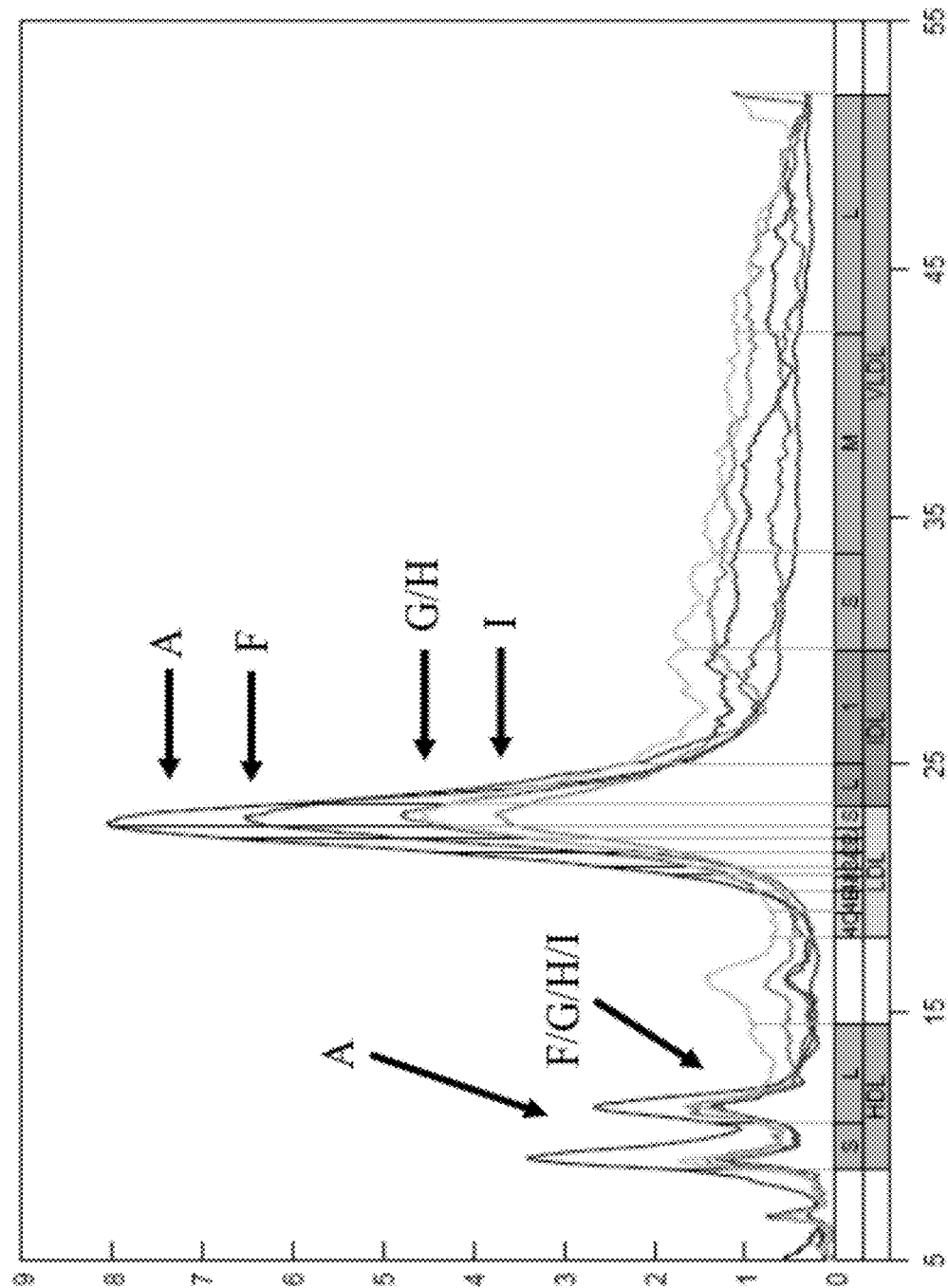

As seen in FIG. 15B, processes using 100 kD dextran sulfate resulted in approximately ¾ to ½ of the LDL recovery of the 50 kD dextran sulfate control, and 500 kD dextran sulfate resulted in approximately ½ of the LDL recovery of the 50 kD dextran sulfate control. Trace A represents the control 50 kD dextran sulfate, traces F and G represents 100 kD dextran sulfate samples, and traces H and I represent 500 kD dextran sulfate samples.

Thus, all dextran sulfates tested demonstrated an ability to precipitate at least some categories of lipoproteins, with dextran sulfates at about 50 kD being able to most effectively precipitate lipoproteins across all lipoprotein size ranges.

Example 14

Effect of Various Cations on Lipoprotein Separation Using Dextran Sulfate and Magnetic Beads Multivalent cations (other than $Mg^{2+}$) were investigated for their effectiveness in a single-stage dextran sulfate/magnetic bead lipoprotein recovery. Serum samples were processed using the procedure set forth in Example 10, but substituting 1) a multivalent cation other than $Mg^{2+}$, and 2) unconjugated dextran sulfate and magnetic beads instead of dextran sulfate and magnetic beads using the biotin-streptavidin system. The multivalent cations tested for effectiveness were $Ca^{2+}$ (from a solution of $CaCl_2$), $Mn^{2+}$ (from a solution of $MnCl_2$), $Be^{2+}$ (from a solution of $BeSO_4$), $Ba^{2+}$ (from a solution of $BaCl_2$), $Sr^{2+}$ (from a solution of $SrCl_2$), $Co^{2+}$ (from a solution of $CoCl_2$), $Zn^{2+}$ (from a solution of $ZnSO_4$), $Ni^{2+}$ (from a solution of $NiCl_2$), $Cu^{2+}$ (from a solution of $CuCl_2$), $Fe^{2+}$ (from a solution of $FeCl_2$), and $Fe^{3+}$ (from a solution of $FeCl_3$). Duplicate samples were processed for each substituted multivalent cation. The results are summarized in Table 5 below and in FIG. 16.

TABLE 5

Effect of Different Cations on Lipoprotein Precipitation

| Cation | Effect on LP | Effect on NSB with lipid-stripped serum |
|---|---|---|
| $MgCl_2$ | get high LDL, medium HDL | NSB under 2 (mass) |
| $CaCl_2$ | get high yield of LP | High NSB in HDL region, up to 10 |
| $MnCl_2$ | Get low yield of LP | High NSB in HDL region, up to 10 |
| $BaCl_2$ | get high yield of LP | High NSB in HDL and below region |
| $SrCl_2$ | get high yield of LP | High NSB in HDL and below region |
| $BeSO4$ | Do not get any LDL | Do not have any NSB |
| $CoCl_2$ | get high yield of LP | very high NSB in HDL region, up to 45 |
| $ZnSO_4$ | get LDL | very high NSB in HDL region, up to 20 |
| $NiCl_2$ | get about half amount of LDL | very high NSB in HDL region, up to 60 |
| $CuCl_2$ | get very small amount of LDL | High NSB in HDL region, up to 4 |
| $FeCl_2$ | Could not see any effect | Could not see any effect |
| $FeCl_3$ | Do not get any LDL | High NSB in HDL region, up to 10 |

*NSB: non-specific binding

Figure 16:
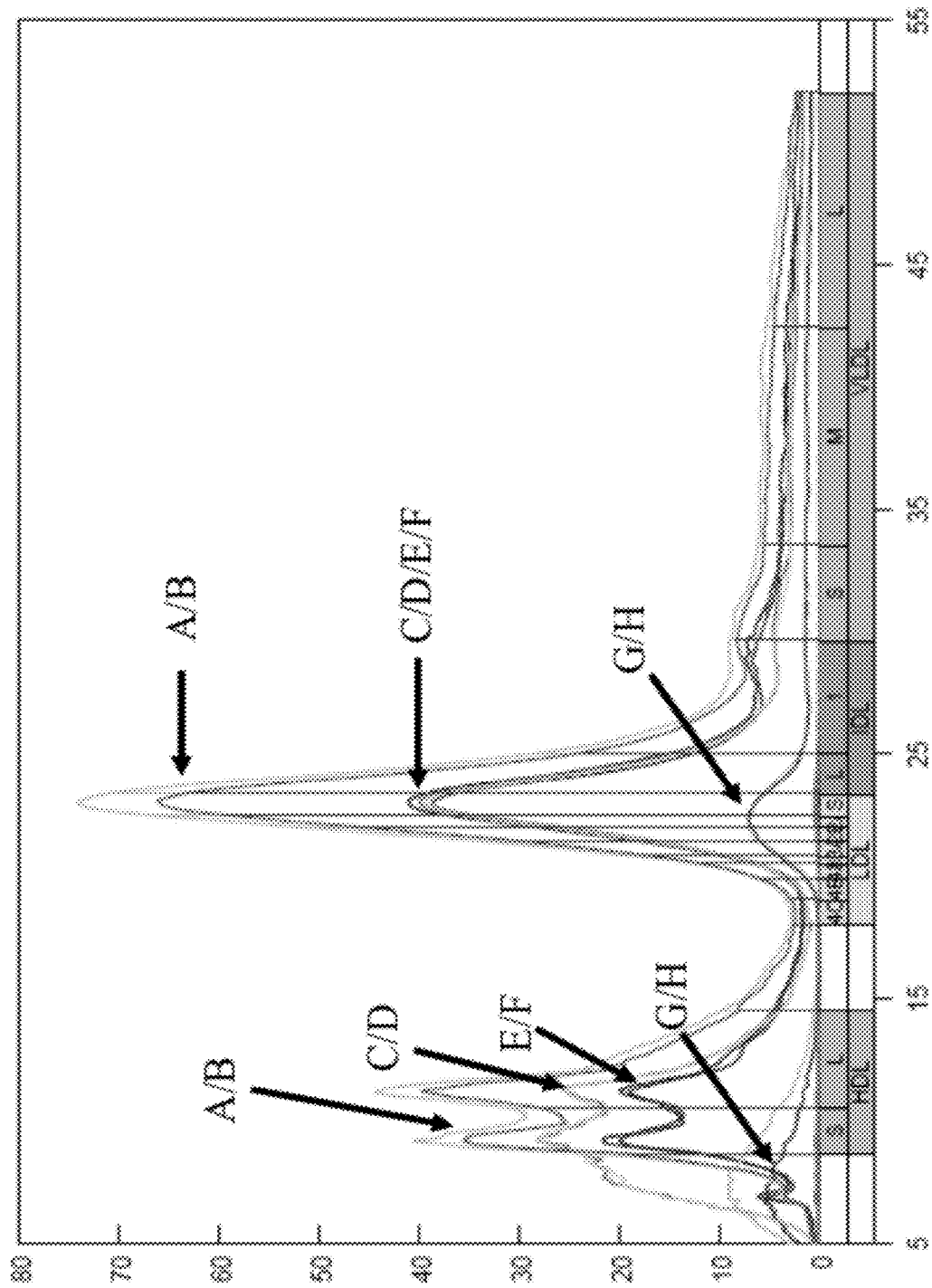
FIG. 16 shows ion mobility profiles of lipoprotein recovered from serum using different divalent cations in dextran sulfate/magnetic bead recoveries. Details are described in Example 14.

As seen in Table 5 and FIG. 16, the identity of the multivalent ion affected the overall yield of the method. Use of $Ca^{2+}$ as the cation resulted in the largest amount of LDL and HDL recovered, with an increased recovery of LDL of between 1.75-fold to 12-fold compared with the other cations tested. $Ca^{2+}$ also increased recovery of HDL to between about 1.4-fold to 2-fold compared with the other cations tested. Of the cations tested, only $Be^{2+}$ was not effective at the concentrations tested.

Exemplary results from these tests are shown in FIG. 16. Traces A and B of FIG. 16 show the amount of lipoprotein recovered using $Ca^{2+}$, traces C and D are from the $Sr^{2+}$ samples, traces E and F are from the $Mn^{2+}$ samples, and traces G and H are from the $Ba^{2+}$ samples.

Example 15

Comparison of Different Magnet Bead Types for Lipoprotein Separation

Different types of commercially available magnetic beads were investigated for their effectiveness in a single-stage dextran sulfate/magnetic bead lipoprotein recovery. Serum samples were processed using the procedure set forth in Example 10, but substituting 1) various types and sizes of magnetic beads, as summarized in Table 6 below, and 2) unconjugated dextran sulfate and magnetic beads instead of dextran sulfate and magnetic beads utilizing the biotin-streptavidin system.

TABLE 6

Effect of Different Beads on Isolation of Lipoproteins

| Bead Brand Name | Bead Surface | Size | Effect on LP precipitation |
|---|---|---|---|
| Dynabeads ™ MyOne ™ Streptavidin T1 | negative-charged, coated with streptavidin | 1 μm | good |
| Sera-Mag ™ Double Speed Magnetic Streptavidin Blocked Microparticle | negative charged, coated with streptavidin | 1.37 μm | good |

TABLE 6-continued

Effect of Different Beads on Isolation of Lipoproteins

| Bead Brand Name | Bead Surface | Size | Effect on LP precipitation |
|---|---|---|---|
| Sera-Mag ™ Magnetic Streptavidin Microparticle | negative-charged, coated with streptavidin | 0.74 μm | better |
| Sera-Mag ™ Magnetic Microparticle Carboxylate-Modified (MG-CM) | negative-charged, coated with carboxyl group | 0.7 μm | better |
| PureProteome ™ Protein G Magnetic Bead | coated with Protein G | Unknown | better |
| Protein L Magnetic Beads | coated with Protein L | 75-150 μm | better |
| NH₂ magnetic beads | Positive-charged, coated with NH2. Do not stick to this magnet. Need to centrifuge to isolate bead/LP | 0.2 μm | better |

The diameter of the magnetic beads varied from 0.2 μm to 150 μm, but the diameter did not appear to affect the yield of lipoprotein using the DS-MB method. Bead coatings such as streptavidin, protein L, and protein G did not perform significantly better than beads coated only with carboxylate or $NH_2$.

Example 16

Comparison of Various Concentrations of $Mg^{2+}$ and $Ca^{2+}$ on Lipoprotein Separation Using Dextran Sulfate and Magnetic Beads In order to compare the effects of $Mg^{2+}$ and $Ca^{2+}$ on lipoprotein recovery using magnetic bead separation, several serum samples were treated as in Example 10 above substituting 1) various concentrations of either $Mg^{2+}$ alone, $Ca^{2+}$ alone, or a combination of $Mg^{2+}$ and $Ca^{2+}$, and 2) unconjugated dextran sulfate and magnetic beads instead of dextran sulfate and magnetic beads utilizing the biotin-streptavidin system. The concentrations of the $Mg^{2+}$ and $Ca^{2+}$ alone ranged between 24 mM and 200 mM.

The optimal concentration of $Ca^{2+}$ alone was 150 mM. The optimal concentration of $Mg^{2+}$ and $Ca^{2+}$ together was 100 mM $Mg^{2+}$ and 25 mM $Ca^{2+}$.

Example 17

Comparison of $Mg^{2+}$ and $Ca^{2+}$ at a Single Concentration on Lipoprotein Separation Using Dextran Sulfate and Magnetic Beads In order to compare the effects of $Mg^{2+}$ and $Ca^{2+}$ on lipoprotein recovery using magnetic bead separation, two serum samples were treated as in Example 10 above substituting 1) 100 mM $Mg^{2+}$ or 100 mM $Ca^{2+}$, and 2) unconjugated dextran sulfate and magnetic beads instead of dextran sulfate and magnetic beads utilizing the biotin-streptavidin system. After the lipoproteins were separated, they were analyzed using the differential charged-particle mobility analysis as described in Example 7.

Figure 17:
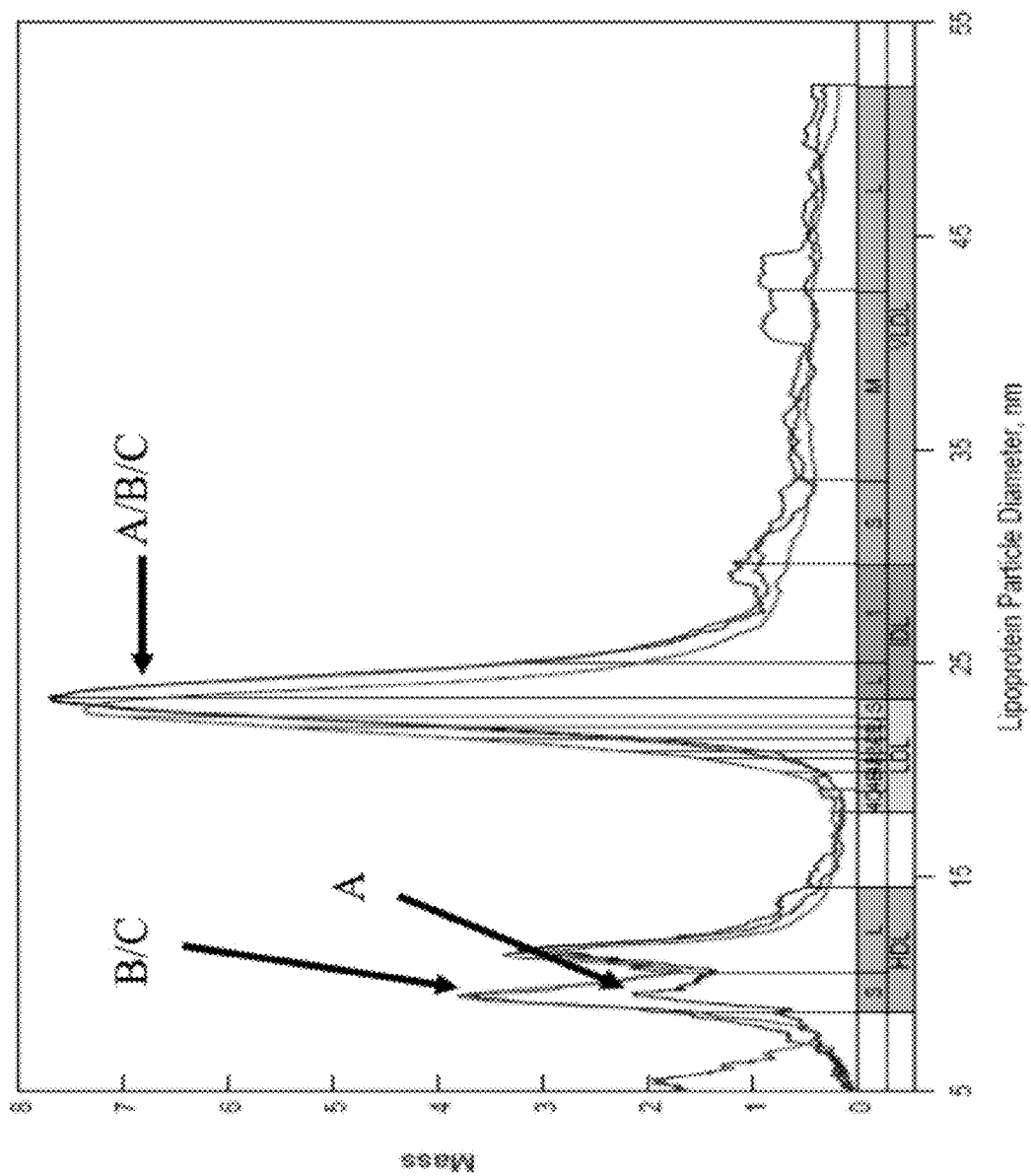
FIG. 17 shows ion mobility profiles of lipoprotein recovered from serum using either 100 mM $Mg^{2+}$ or 100 mM $Ca^{2+}$ in dextran sulfate/magnetic bead recoveries. Details are described in Example 15.

FIG. 17 shows the results of the ion mobility analysis. Trace A is the $Mg^{2+}$-treated sample, trace B is the $Ca^{2+}$-treated sample, and trace C is the control sample. Both $Ca^{2+}$- and $Mg^{2+}$-treated samples (traces A and B) demonstrated approximately 100% recovery for the LDL and HDL-L relative to the control sample (trace C). However, the $Mg^{2+}$-treated sample (trace B) recovered only 68% of the HDL-S relative to the amounts recovered in the control sample and the $Ca^{2+}$-treated sample (traces B and C).

Example 18

Comparison of the Effect of $Mg^{2+}$ and $Ca^{2+}$ on Non-Specific Binding During Lipoprotein Separation Using Dextran Sulfate and Magnetic Beads To measure whether $Ca^{2+}$ and $Mg^{2+}$ cause differing levels of non-specific binding by the dextran sulfate or magnetic beads, HDL was recovered from two aliquots of serum sample using the process outlined in Example 10. One aliquot used $Ca^{2+}$ as a divalent cation, the other aliquot used $Mg^{2+}$ as a divalent cation.

Figure 18:
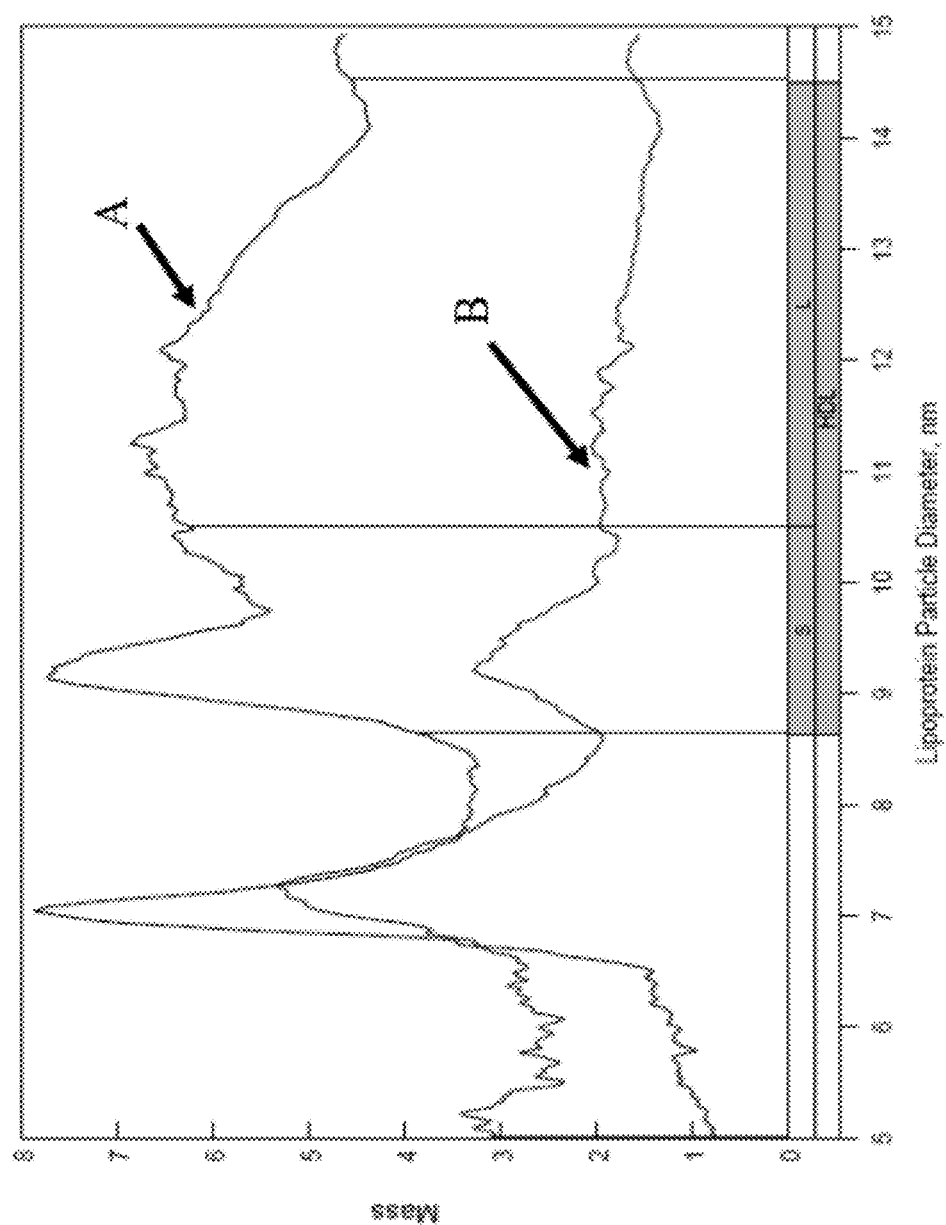
FIG. 18 shows ion mobility profiles of lipoprotein recovered from serum using either 100 mM $Mg^{2+}$ or 100 mM $Ca^{2+}$ in dextran sulfate/magnetic bead recoveries, and the higher levels of background signal when $Ca^{2+}$ is used. Details are described in Example 16.

Although $Ca^{2+}$ gave a higher yield of lipoprotein generally, there was also higher non-specific binding, resulting in a higher background signal. As seen in FIG. 18 (trace A is from the $Ca^{2+}$-treated sample and trace B is from the $Mg^{2+}$-treated sample), the background level of non-specific HDL particles was about 3-fold higher for $Ca^{2+}$ than for $Mg^{2+}$.

Example 19

Comparison of Lipoprotein Separation: Unconjugated DS/MB vs. Ultracentrifugation In order to compare the lipoprotein recovery of the single-stage dextran sulfate/magnetic bead (DS-MB) method to lipoprotein recovery using ultracentrifugation method, two aliquots of a serum sample were processed. One aliquot was processed using the ultracentrifugation methods of Example 6, and the other aliquot was processed using the single-stage DS-MB method set forth in Example 10. The DS/MB method was conducted with a mixture of cations, 100 mM $MgCl_2$ and 25 mM $CaCl_2$.

Figure 19:
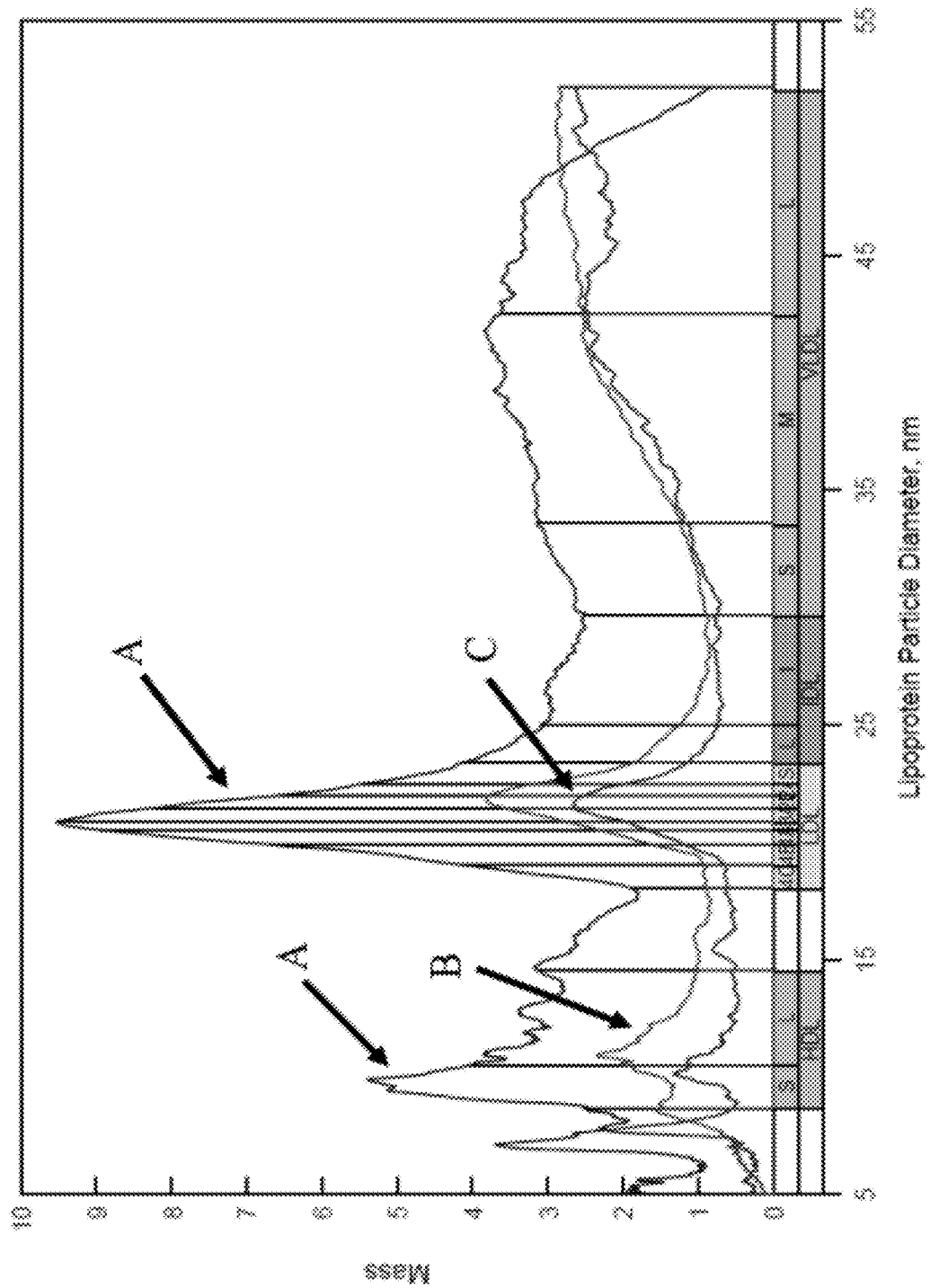
FIG. 19 shows ion mobility profiles of lipoprotein recovered from serum using either unconjugated dextran sulfate and magnetic beads or ultracentrifugation. Details are described in Example 17.

The data from these analyses are shown in FIG. 19. Trace A shows the LDL and HDL recovered using the DS-MB method, trace B shows the LDL recovered using ultracentrifugation, and Trace C shows the HDL recovered using ultracentrifugation. As seen in FIG. 19, the DS-MB method of lipoprotein recovery provided more than two-fold greater LDL recovery than the ultracentrifugation method.

Example 20

Comparison of Different Lipoprotein Precipitators

To investigate what precipitating reagents other than dextran sulfate could be used to separate lipoproteins from plasma or serum samples without biotinylation, a variety of reagents were substituted for dextran sulfate using the method set forth in Example 10. The lipoprotein precipitating reagents tested were: chondroitin sulfate sodium salt; chondroitin 6-sulfate sodium salt; chondroitin sulfate A sodium salt; phosphotungstic acid; heparin sulfate sodium; and DEAE-dextran hydrochloride. Of these potential precipitators, only phosphotungstic acid was able to precipitate lipoproteins at the concentrations investigated. However, lipoproteins precipitated with phosphotungstic acid were unable to release from the beads using a pH 8.5 ammonium acetate wash solution.

Example 21

Separation of Lipoproteins Using Unconjugated Dextran Sulfate and Carboxylated Magnetic Beads 90 μl of serum was mixed with 10 μl ethanol and incubated on ice for 15 minutes to remove fibrinogen from the sample. The mixture was centrifuged for 5 minutes at 1100×G, and 3 μl was combined with 7 μl of glycine. The glycine mixture was then added to 10 μl of 50 kD dextran sulfate and $MgCl_2$ and $CaCl_2$, such that the $MgCl_2$ and $CaCl_2$ concentrations in the glycine-dextran sulfate mixture were 100 mM and 25 mM, respectively. The glycine-dextran sulfate mixture was then incubated for 3 minutes to precipitate lipoproteins in the sample.

Next, 20 μl of magnetic beads (Sera-Mag Magnetic Carboxylated-Modified Microparticles; Thermo Fisher Scientific) were added to the glycine-dextran sulfate mixture and incubated for 3 minutes to capture the precipitated lipoproteins. A magnet was then applied to collect the magnetic beads, and the supernatant was discarded. The beads were mixed with 100 μl of 25 mM ammonium acetate (pH≈9) and allowed to incubate for 3 minutes to remove the collected lipoproteins from the beads. A magnet was then applied to the bead mixture and the supernatant containing the lipoproteins was collected. The supernatant was diluted 1:800 and analyzed using differential charged-particle mobility analysis as described in Example 7.

All lipoprotein subfractions of interest, including HDL and LDL, were successfully precipitated and quantitated.

Example 22

Lipoprotein Reference Ranges

To calculate reference ranges for lipoproteins fractionated using ion mobility analysis, lipoproteins were measured in 345 subjects using the procedure of Example 7. The subjects included 244 females and 101 males between the ages of 18-70 years. The inclusion criteria were: Cholesterol<=200, Triglycerides<=150, Direct LDL<=130 and HDL>=40 for males and HDL>=50 for females. The exclusion criteria were: Cholesterol>200 or Triglycerides>150 or Direct LDL>130 or HDL<40 for males and HDL<50 for females. The $95^{th}$ percentile ranges were used for all subtypes. The resulting reference ranges for lipoprotein subtypes are listed in Table 7 below.

TABLE 7

Ion Mobility-Lipoprotein Particle Subtypes Reference Ranges

| Lipoprotein Subtype | Female | Male |
| --- | --- | --- |
| LDL Peak Diameter | 216.0-234.3 Å | 216.0-234.3 Å |
| LDL, Total | 396-1461 nmol/L | 440-1600 nmol/L |
| LDL, Medium + Small | 105-521 nmol/L | 144-787 nmol/L |
| LDL, Very Small | 77-293 nmol/L | 75-419 nmol/L |
| Non-HDL | 571-2003 nmol/L | 582-2142 nmol/L |
| HDL, Large | 1153-7796 nmol/L | 469-5258 nmol/L |

Goals for the different lipoprotein subtypes are based on the male and female reference ranges. The cut-off for LDL Peak Diameter represents the lower end of the reference range for female data, while the cut-off for the remaining criteria represent the $50^{th}$ percentile of the combined male and female data. The goal diameters and concentrations for the lipoprotein subtypes are listed in Table 8 below.

TABLE 8

Goals: Ion Mobility-Lipoprotein Particle Subtypes

| Lipoprotein Subtype | Female & Male |
| --- | --- |
| LDL Peak Diameter | >216.0 Å |
| LDL, Total | <915 nmol/L |
| LDL, Medium + Small | <304 nmol/L |
| LDL, Very Small | <218 nmol/L |
| HDL, Large | >3017 nmol/L |

Example 23

Lipoprotein Separation of Patient Samples Using DS/MB

Patient serum samples (30 μL each) were added to 70 μL of a first precipitation solution (25 mL glycine [150 mg/ml], 12 mL ethanol [100%], 10 mL $CaCl_2$ [1 M]), mixed in a 96-well plate, and incubated on ice for about 15 minutes. The mixture was then centrifuged at 2000 RCF for about 5 minutes at 15° C., and the resulting supernatant was removed.

Equal amounts of supernatant and a second precipitation solution (20 mL dextran sulfate [20 mg/mL]; 15 mL $CaCl_2$ [1 M]; 15 mL ammonium acetate, pH 7.4 [25 mM]) were then mixed and incubated for 3 minutes at room temperature. About 20 μL of magnetic bead solution (3.5 mg/mL SeraMag Magnetic microparticles reconstituted in 25 mM ammonium acetate, pH 7.4; Thermo Fisher Scientific Cat. No. 2415-2105-0502-50) was then added to the mixture and incubated for 3 minutes at room temperature. The bead mixture was then incubated over a 96-well magnet plate (PerkinElmer Cat. No. 7002416) for 1 minute, and the resulting supernatant was removed and discarded.

The bead mixture remaining in the magnetic plate was briefly washed with 10 μL of releasing buffer (27.5 mM ammonium acetate at pH 8.4), and again placed above the 96-well magnet plate. About 200 μL of releasing buffer was then added to the bead mixture, mixed, and incubated above the magnet for another 2 minutes. The supernatant was removed, and then diluted 1:18 with sample dilution buffer (25 mM ammonium acetate, pH 7.4).

Example 24

Ion Mobility Analysis of DS/MB Lipoprotein-Separated Patient Samples

Lipoproteins separated from patient samples using DS/MB as described in Example 23 were analyzed using a TSI Model 3980 Gas-phase Electrophoretic-Mobility Molecular Analyzer (GEMMA) (TSI, Inc.; Shoreview, Minn.). The GEMMA system includes the Model 3480 Electrospray Aerosol Generator (EAG), the Model 3080 Electrostatic Classifier (EC), and the Model 3786 Ultrafine Water-based Condensation Particle Count (wCPC), and was used according to standard methods known in the art. See, e.g., Benner et al., U.S. Pat. No. 7,259,018. Two sets of two samples are run, each of the two samples having with different LDL profiles are run.

Protein interference is minimized in this procedure due to the initial purification of the lipids from the serum/plasma proteins using DS/MB. Any additional small compounds that may not removed during the DS/MB lipoprotein separation, such as bilirubin, are detected as a particle of a size less than the smallest HDL particle and thus do not interfere.

Example 25

Figure 20B:
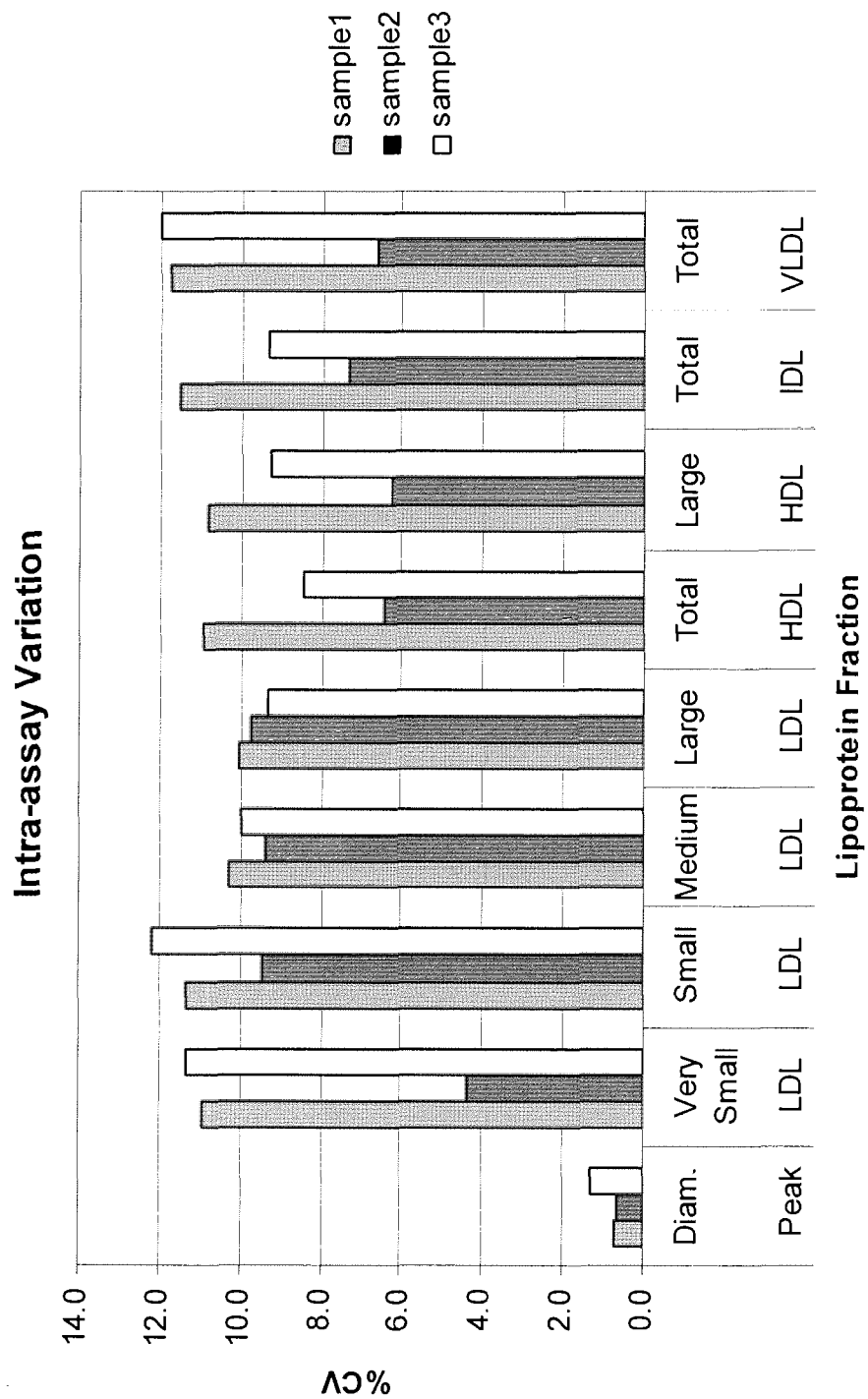
FIG. 20B shows a bar graph of % CV for individual lipoprotein fractions from a study of intra-assay precision. Details are described in Example 25.

Intra-Assay Precision Study for Ion Mobility Analysis of DS/MB Lipoprotein-Separated Patient Samples Intra-assay precision was determined by preparing ten replicates from each of 3 patient samples using the lipoprotein separation method described in Example 23, and then analyzing the 30 samples in a single run, as described in Example 24. The reproducibility of the lipoprotein factions was determined by calculating the mean, standard deviation and CV. Summary data are given in FIG. 20A. FIG. 20B shows a graph of the percent CV of individual lipoprotein fractions from replicates of the three patient samples. All of the lipoprotein fractions, including IDL and VLDL, had 15% CV. The intra-assay CV for LDL particle size was <1.5%.

Example 26

Figure 21B:
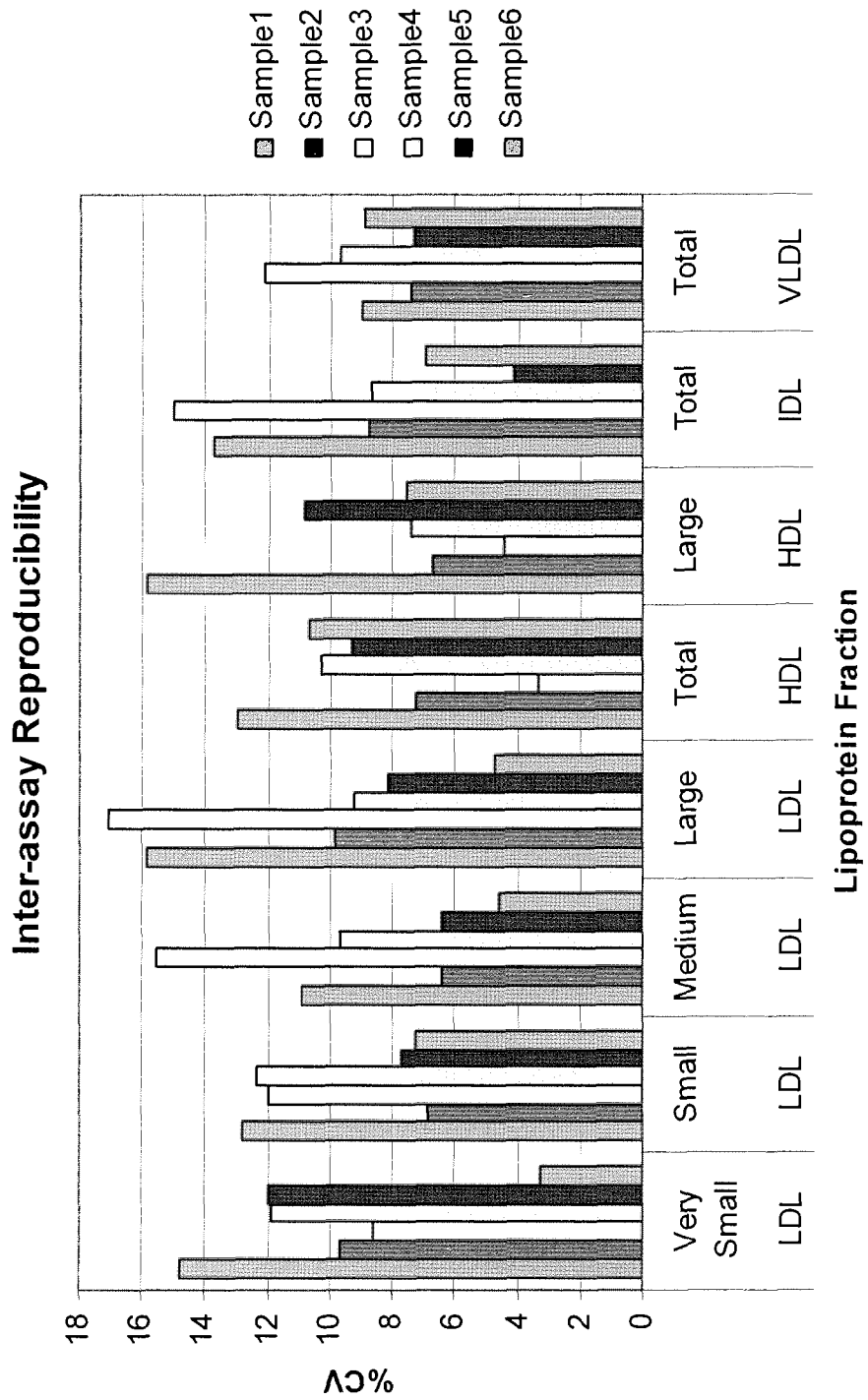
FIG. 21B shows a bar graph of % CV for the study of inter-assay variation. Details are described in Example 26.

Inter-Assay Precision Study for Ion Mobility Analysis of DS/MB Lipoprotein-Separated Patient Samples Inter-assay variation was defined as the reproducibility (CV) of a sample between assays. Six samples were prepared using the method of Example 23 and analyzed using the method of Example 24 in replicates of 11 to 13 on four different days to give a total of 47 to 51 replicates. FIG. 21A shows a summary table for mean, standard deviation, and % CV for inter-assay variation in particle size. FIG. 21B shows a bar graph of % CV for these samples. The % CV was <1.0% (0.6-0.9) for all six samples.

Example 27

Detection Limits for Ion Mobility Analysis of DS/MB Lipoprotein-Separated Patient Samples Data for 20 patient samples prepared as described in Example 23 and analyzed as described in Example 24 were analyzed for the limit of detection and the limit of quantitation. The Limit of Blank (LOB) calculation was defined as: LOB=mean of blank+2SD. The Limit of Detection (LOD) calculation was defined as: LOD=mean of blank+4SD. The Limit of Quantitation was defined as LOQ=mean of blank+10 SD. Detection limit data is summarized in FIG. 22. The LOQ for all HDL was 0.370 and the LOD was 0.179. The LOQ for HDL peak diameter was 0.293 and the LOD was 0.221. The LOQ for IDL was 0.052 and the LOD was 0.22. The LOQ for all LDL was 0.114 and the LOD was 0.050. The LOQ for all VLDL was 0.118 and the LOD was 0.053.

Example 28

HDL and Cholesterol Recovery Study for Ion Mobility Analysis of DS/MB Lipoprotein-Separated Patient Samples Five patient samples were prepared in several replicates according to the method of Example 23. Half of the replicates were treated with the first precipitation solution to remove fibrinogen and the other half were not. Some of the replicates were also treated with EDTA or heparin. The replicates were analyzed using the method of Example 24 and the percent recovery of HDL (ApoA1) and cholesterol were determined.

Recovery of HDL from the samples was >84%; data for HDL is summarized in table 9 below.

TABLE 9

Summary Data for HDL Recovery (μg/mL)

| Sample ID | Original | LP (with first precip. soln.) | LP (no first precip. soln.) | % Recovery (with first precip. soln.) | % Recovery (no first precip. soln.) |
|---|---|---|---|---|---|
| serum1 | 442 | 416 | 415 | 94 | 94 |
| EDTA1 | 437 | 489 | 389 | 112 | 89 |
| heparin1 | 337 | 405 | 343 | 120 | 102 |
| serum2 | 454 | 449 | 407 | 99 | 90 |
| EDTA2 | 428 | 367 | 331 | 86 | 77 |
| heparin2 | 428 | 514 | 365 | 120 | 85 |
| serum3 | 366 | 269 | 219 | 73 | 60 |
| heparin3 | 375 | 350 | 291 | 93 | 78 |
| serum4 | 381 | 297 | 345 | 78 | 90 |
| serum5 | 455 | 387 | 406 | 85 | 89 |
| | | | Avg. | 96 | 85 |

Figure 23:
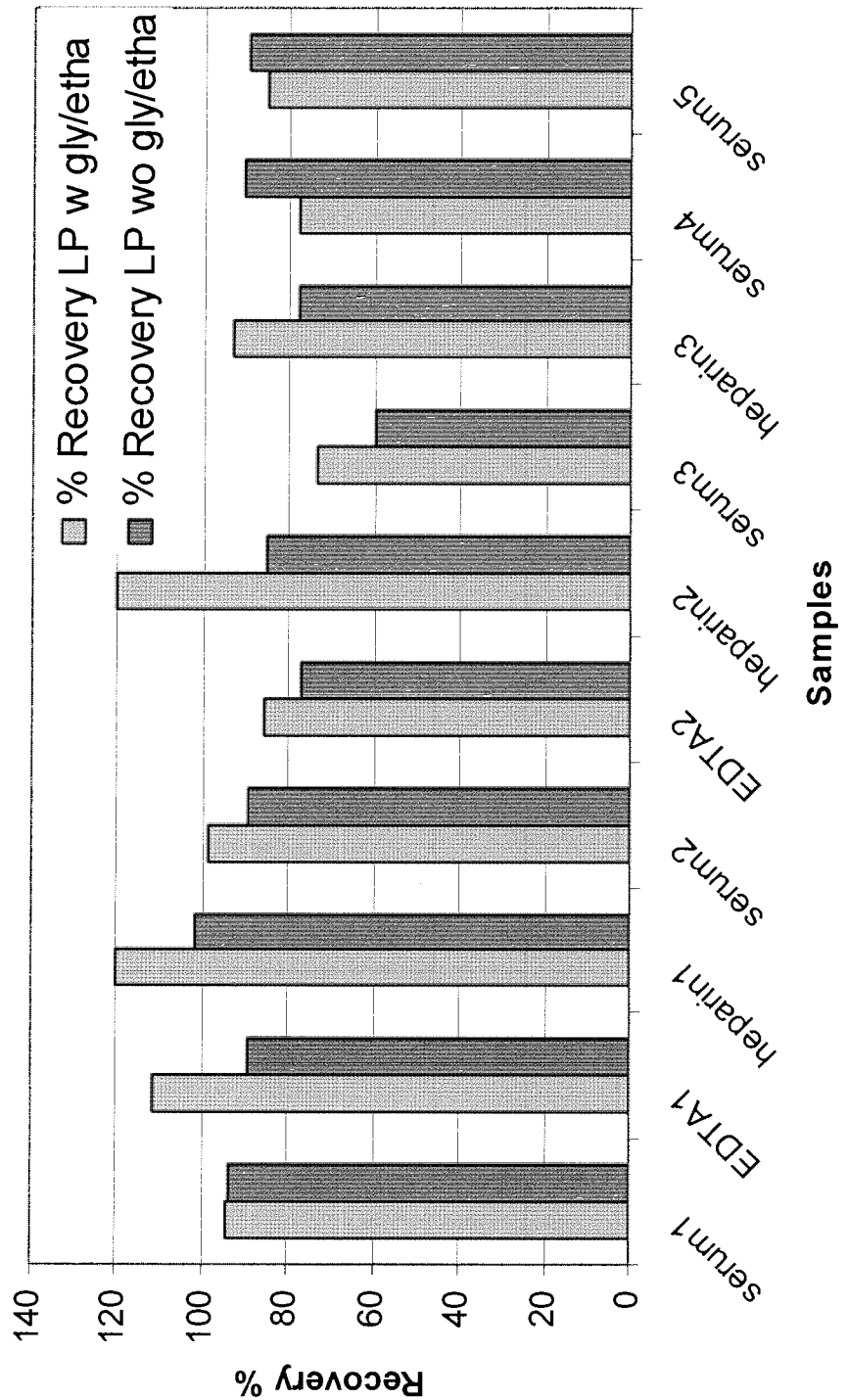
FIG. 23 shows a bar graph of cholesterol recovery using dextran sulfate and magnetic beads. Details are described in Example 28.

Recovery of cholesterol was >90%. Data for cholesterol is summarized in table 10 below and in a bar graph shown in FIG. 23.

TABLE 10

Summary Data for Cholesterol Recovery in mM

| Sample ID | Original (no first precip. soln.) | LP Extract (no first precip. soln.) | LP Extract (with first precip. soln.) | % Recovery (no first precip. soln.) | % Recovery (with first precip. soln.) |
|---|---|---|---|---|---|
| serum1 | 3.62 | 3.80 | NA | 105.1 | NA |
| EDTA1 | 2.85 | 3.59 | NA | 126.2 | NA |
| heparin1 | 3.13 | 4.23 | NA | 135.1 | NA |
| serum2 | 4.00 | 3.61 | NA | 90.4 | NA |
| EDTA2 | 3.77 | 3.59 | NA | 95.4 | NA |
| heparin2 | 3.71 | 3.56 | NA | 96.1 | NA |
| serum3 | 5.36 | 4.24 | 4.62 | 79.1 | 86.3 |
| EDTA3 | 4.83 | 4.42 | 4.24 | 91.7 | 87.9 |
| heparin3 | 4.76 | 4.77 | 3.99 | 100.2 | 83.8 |
| serum4 | 3.70 | 3.83 | 3.76 | 103.5 | 101.7 |
| serum5 | 3.42 | 4.48 | 3.12 | 131.2 | 91.5 |
| serum6 | 5.26 | 5.40 | 5.18 | 102.6 | 98.4 |
| serum7 | 4.35 | 3.48 | 3.59 | 80.1 | 82.6 |
| | | | Avg. | 102.8 | 90.3 |

Example 29

Fibrinogen Removal Study for Ion Mobility Analysis of DS/MB Lipoprotein-Separated Patient Samples Six patient serum samples were each split into 3 replicates: one replicate without additives, one replicate with EDTA added, and one replicate with heparin added (for a total of 18 replicates). The replicates were then prepared according to the lipoprotein separation method of Example 23 and the level of fibrinogen in each replicate was analyzed before and after lipoprotein separation. Fibrinogen removal from non-additive serum samples, EDTA serum samples, and heparin serum samples is between about 95-99%. The data are summarized in FIG. 24.

Example 30

Figure 25:
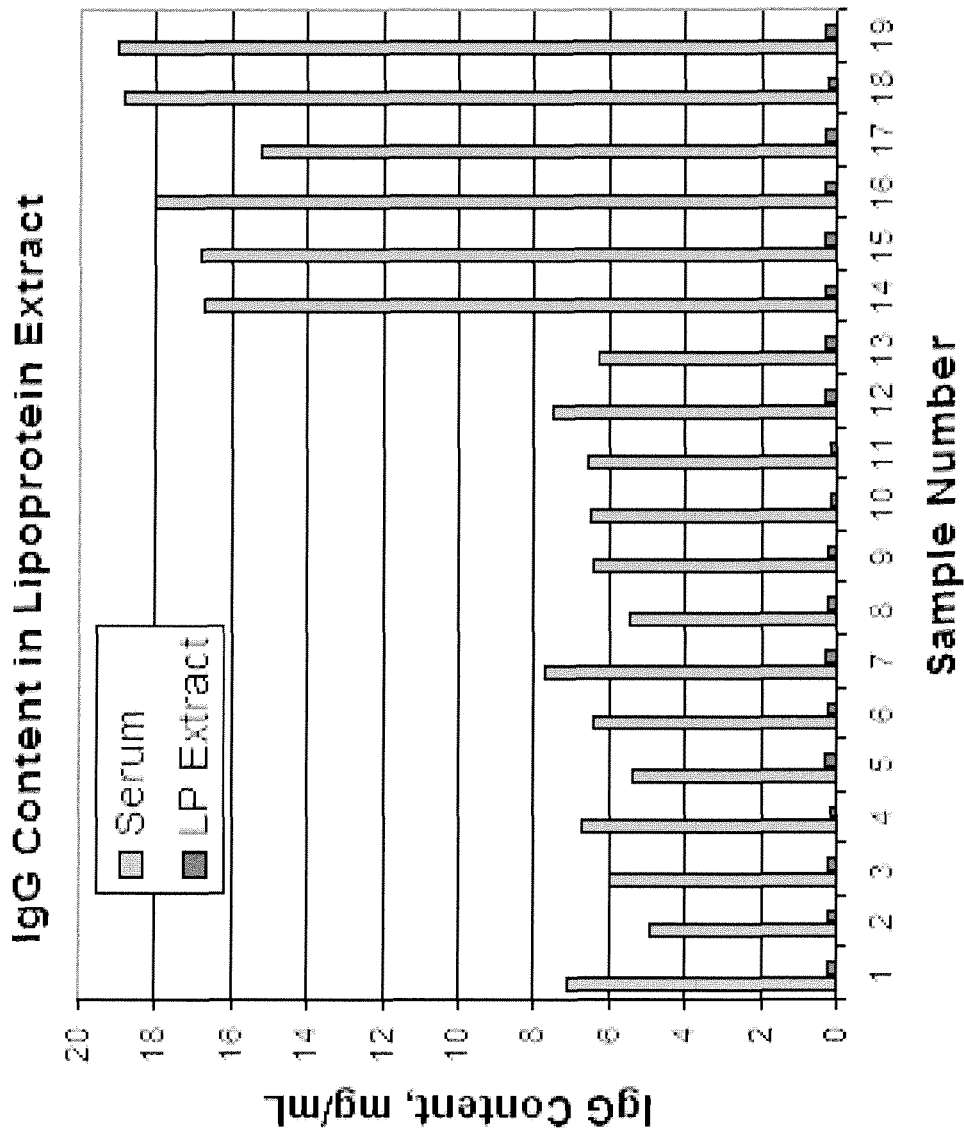
FIG. 25 shows a bar graph of data on IgG removal from serum samples using dextran sulfate and magnetic beads. Details are described in Example 30.

IgG Removal Study for Ion Mobility Analysis of DS/MB Lipoprotein-Separated Patient Samples Nineteen patient serum samples were prepared according to the lipoprotein separation method of Example 23 and the level of IgG in each sample was analyzed before and after lipoprotein separation. Removal of IgG from serum samples was between about 94-98.7%. The data are summarized in Table 11 below and in FIG. 25.

TABLE 11

Summary Data for IgG Removal Study

| Sample ID | Serum (mg/mL) | LP Extract (mg/mL) | % removed |
|---|---|---|---|
| 1 | 7.11 | 0.25 | 96.55 |
| 2 | 4.92 | 0.19 | 96.05 |
| 3 | 6.00 | 0.21 | 96.42 |
| 4 | 6.74 | 0.19 | 97.23 |
| 5 | 5.41 | 0.27 | 94.99 |
| 6 | 6.47 | 0.21 | 96.80 |
| 7 | 7.73 | 0.29 | 96.24 |
| 8 | 5.49 | 0.22 | 95.94 |
| 9 | 6.46 | 0.20 | 96.89 |
| 10 | 6.55 | 0.19 | 97.15 |
| 11 | 6.59 | 0.18 | 97.24 |
| 12 | 7.48 | 0.28 | 96.23 |
| 13 | 6.29 | 0.29 | 95.35 |
| 14 | 16.73 | 0.30 | 98.22 |
| 15 | 16.78 | 0.31 | 98.15 |
| 16 | 18.07 | 0.30 | 98.33 |
| 17 | 15.19 | 0.30 | 98.03 |
| 18 | 18.85 | 0.24 | 98.70 |
| 19 | 19.02 | 0.32 | 98.32 |
| | | Avg: | 96.99 |

Example 31

Figure 26:
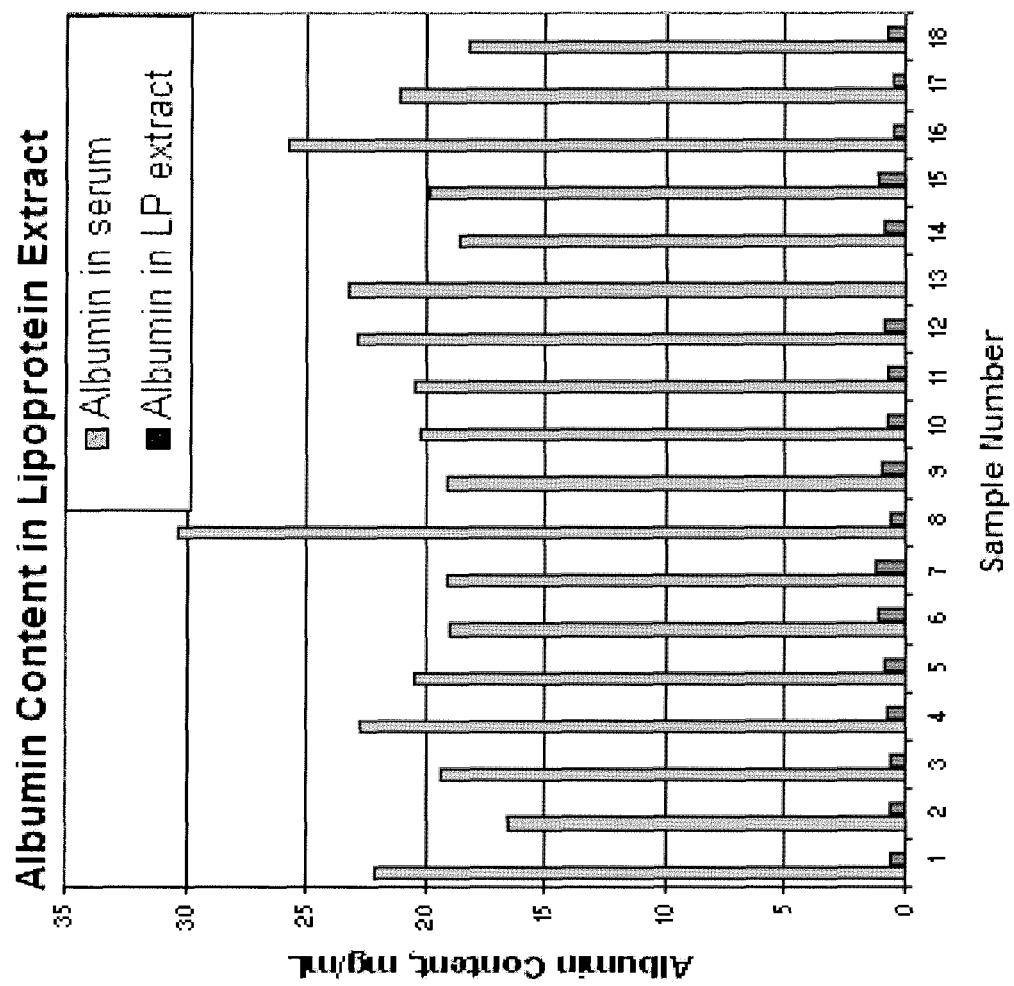
FIG. 26 shows a bar graph of data on transferrin removal from serum samples using dextran sulfate and magnetic beads. Details are described in Example 32.

Albumin Removal Study for Ion Mobility Analysis of DS/MB Lipoprotein-Separated Patient Samples Eighteen patient serum samples were prepared according to the lipoprotein separation method of Example 23 and the level of albumin in each sample was analyzed before and after lipoprotein separation. Removal of albumin from serum samples was between about 97.9-99.8%. The data are summarized in Table 12 below and in FIG. 26.

TABLE 12

Summary Data for Albumin Removal Study

| Sample ID | Serum (mg/mL) | LP extract (mg/mL) | % Removed |
|---|---|---|---|
| 1 | 22.09 | 0.65 | 2.9 |
| 2 | 16.60 | 0.57 | 3.4 |
| 3 | 19.38 | 0.67 | 3.4 |
| 4 | 22.80 | 0.70 | 3.1 |
| 5 | 20.43 | 0.89 | 4.4 |
| 6 | 18.91 | 1.18 | 6.3 |
| 7 | 19.05 | 1.28 | 6.7 |
| 8 | 30.36 | 0.65 | 2.1 |
| 9 | 19.03 | 1.00 | 5.2 |
| 10 | 20.18 | 0.76 | 3.8 |
| 11 | 20.52 | 0.75 | 3.7 |
| 12 | 22.91 | 0.91 | 4.0 |
| 13 | 23.20 | 0.04 | 0.2 |
| 14 | 18.56 | 0.86 | 4.6 |
| 15 | 19.79 | 1.12 | 5.7 |
| 16 | 25.83 | 0.56 | 2.2 |
| 17 | 21.16 | 0.54 | 2.5 |
| 18 | 18.22 | 0.79 | 4.4 |
| | | Avg. | 3.8 |

Example 32

Transferrin Removal Study for Ion Mobility Analysis of DS/MB Lipoprotein-Separated Patient Samples Six patient serum samples were each split into 3 replicates: one replicate without additives, one replicate with EDTA added, and one replicate with heparin added (18 replicates plus 2 extra serum samples for a total of 20 samples). The replicates and extra samples were then prepared according to the lipoprotein separation method of Example 23 and the level of transferrin in each replicate was analyzed before and after lipoprotein separation. Transferrin removal from non-additive serum samples, EDTA serum samples, and heparin serum samples was determined to be more than about 99.5%. The data are summarized in Table 13 as follows.

TABLE 13

Summary Data for Transferrin Removal Study

| Sample ID | Serum (mg/mL) | LP extract (mg/mL) | % Recovered |
|---|---|---|---|
| serum 1 | 21.43 | 0.1 | 0.5 |
| Heparin 1 | 19.52 | 0.1 | 0.5 |
| EDTA 1 | 29.79 | 0.1 | 0.3 |
| serum 2 | 19.88 | 0.11 | 0.6 |
| serum 3 | 14.93 | 0.08 | 0.5 |
| Heparin 3 | 19.76 | 0.08 | 0.4 |
| EDTA 3 | 24.72 | 0.1 | 0.4 |
| serum 4 | 31.99 | 0.12 | 0.4 |
| Heparin 4 | 31.13 | 0.12 | 0.4 |
| EDTA 4 | 47.88 | 0.12 | 0.2 |
| serum 5 | 21.73 | 0.09 | 0.4 |
| Heparin 5 | 17.8 | 0.08 | 0.4 |
| EDTA 5 | 54.22 | 0.07 | 0.1 |
| serum 6 | 22.39 | 0.1 | 0.5 |
| Heparin 6 | 21.76 | 0.11 | 0.5 |
| EDTA 6 | 35.11 | 0.11 | 0.3 |
| serum 7 | 22.17 | 0.09 | 0.4 |
| Heparin 7 | 24.5 | 0.1 | 0.4 |
| EDTA 7 | 45.58 | 0.1 | 0.2 |
| serum 8 | 27.89 | 0.11 | 0.4 |
| Avg. | 27.71 | 0.1 | 0.39 |

All patents and other references cited in the specification are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses which will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

Thus, additional embodiments are within the scope of the invention and within the following claims.

What is claimed is:

1. A method for purifying lipoproteins suitable for differential charged-particle mobility analysis of lipoprotein class and subclass, said method comprising:
    (a) adding one or more cations and dextran sulfate to a sample comprising lipoproteins to form a precipitation mixture;
    (b) contacting the precipitation mixture with a microbead under conditions for one or more classes or subclasses of lipoproteins in said mixture to bind to an inert outer layer of the microbead, wherein said inert outer layer comprises carboxylate or $NH_2$, but does not include a lipoprotein binding lipoprotein-capture ligand;
    (c) separating lipoproteins bound to the microbead from said mixture to obtain a microbead with bound lipoproteins; and
    (d) removing said bound lipoproteins from the microbead; wherein said lipoproteins bound to the microbead comprise HDL and one or more selected from the group consisting of LDL, Lp(a), IDL and VLDL.

2. The method of claim 1, comprising a step of adding glycine.

3. The method of claim 1, wherein said cations comprise one or more divalent cations.

4. The method of claim 3, wherein said one or more divalent cations are selected from the group consisting of $Mg^{2+}$, $Ca^{2+}$, $Mn^{2+}$, and $Sr^{2+}$.

5. The method of claim 3, wherein said one or more divalent cations comprise $Ca^{2+}$.

6. The method of claim 5, wherein said precipitation mixture comprises $Ca^{2+}$ at a concentration within the range of about 25 mM to about 200 mM.

7. The method of claim 5, wherein said precipitation mixture comprises $Ca^{2+}$ at a concentration of about 150 mM.

8. The method of claim 3, wherein said one or more divalent cations comprise $Mg^{2+}$.

9. The method of claim 8, wherein said precipitation mixture comprises $Mg^{2+}$ at a concentration within the range of about 25 mM to about 200 mM.

10. The method of claim 8, wherein said precipitation mixture comprises $Mg^{2+}$ at a concentration of about 100 mM.

11. The method of claim 3, wherein said one or more divalent cations comprise $Ca^{2+}$ and $Mg^{2+}$.

12. The method of claim 11, wherein said precipitation mixture comprises $Ca^{2+}$ at a concentration within the range of about 25 mM to about 200 mM and $Mg^{2+}$ at a concentration within the range of about 25 mM to about 200 mM.

13. The method of claim 11, wherein said precipitation mixture comprises $Ca^{2+}$ at a concentration of about 25 mM and $Mg^{2+}$ at a concentration of about 100 mM.

14. The method of claim 1, wherein said dextran sulfate is in the size range of about 10 to about 500 kDa.

15. The method of claim 1, wherein said dextran sulfate is in the size range of about 50 to about 100 kDa.

16. The method of claim 1, wherein said dextran sulfate has a size of about 50 kDa.

17. The method of claim 1, wherein said microbeads are in the size range of about 0.2 μm to about 150 μm.

18. The method of claim 1, wherein said microbeads comprise a magnetic or paramagnetic core.

19. The method of claim 1, wherein said lipoproteins comprise HDL and LDL.

20. The method of claim 1, wherein said sample is plasma or serum.

21. The method of claim 1, wherein said sample is exposed to ethanol prior to step (a) under conditions suitable to precipitate fibrinogen in the sample.

22. A method for analyzing the size distribution of lipoproteins, said method comprising:
    (a) adding one or more cations and dextran sulfate to a sample comprising lipoproteins to form a precipitation mixture;
    (b) contacting the precipitation mixture with a microbead under conditions for one or more classes or subclasses of lipoproteins in said mixture to bind to an inert outer layer of the microbead, wherein said inert outer layer comprises carboxylate or $NH_2$, but does not include a lipoprotein binding lipoprotein-capture ligand;
    (c) separating lipoproteins bound to the microbead from said mixture to obtain a microbead with bound lipoproteins;
    (d) removing said bound lipoproteins from the microbead; wherein said lipoproteins bound to the microbead comprise HDL and one or more selected from the group consisting of LDL, Lp(a), IDL and VLDL; and (e) subjecting said lipoproteins to differential charged-particle mobility analysis, thereby determining the size distribution of said lipoproteins.

23. The method of claim 22, further comprising:

(f) determining said lipoproteins size distribution to conduct an assessment of said individual, said assessment selected from the group consisting of lipid-related health risk, cardiovascular condition, risk of cardiovascular disease, and responsiveness to a therapeutic intervention.

24. A method for purifying lipoproteins for differential charged-particle mobility analysis, said method not including immunopurification, said method comprising:

(a) admixing a solution comprising lipoproteins and non-lipoproteins with one or more polyanionic compounds and one or more divalent cations;

(b) allowing a precipitate containing lipoproteins to form in said admixed solution; and (c) after step (b), collecting the precipitated lipoproteins by contacting with a microbead under conditions for one or more classes or subclasses of the precipitated lipoproteins to bind to an inert outer layer of the microbead, wherein said inert outer layer comprises carboxylate or $NH_2$, but does not include a lipoprotein-capture ligand;

wherein said lipoproteins bound to the microbead comprise HDL and one or more selected from the group consisting of LDL, Lp(a), IDL and VLDL.

25. The method of claim 24, wherein said polyanionic compounds are not biotinylated and said precipitated lipoproteins are not bound to said solid support by streptavidin.

26. The method of claim 24, wherein said polyanionic compound is dextran sulfate, and wherein said one or more divalent cations are selected from the group consisting of $Mg^{2+}$ and $Ca^{2+}$.

27. The method of claim 24, wherein said solution is exposed to ethanol prior to step (a) under conditions suitable to precipitate fibrinogen in the sample.

28. The method of claim 24, wherein said microbeads are in the size range of about 0.2 µm to about 150 µm.

29. The method of claim 24, wherein said microbeads comprise a magnetic or paramagnetic core.

* * * * *